(12) United States Patent
Ohtake et al.

(10) Patent No.: US 6,407,096 B1
(45) Date of Patent: Jun. 18, 2002

(54) BENZENE FUSED HETEROCYCLIC DERIVATIVES HAVING THROMBOXANE $A_2$ RECEPTOR ANTAGONISTIC ACTIVITY AND PROSTAGLANDIN $I_2$ AGONISTIC ACTIVITY AND APPLICATION THEREOF

(75) Inventors: Atsushi Ohtake; Michihiro Ohno; Kazuhiro Hoshi; Takahiro Takeda; Naohiro Yamada, all of Kanagawa (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/509,909

(22) PCT Filed: Aug. 4, 1999

(86) PCT No.: PCT/JP99/04215

§ 371 (c)(1),
(2), (4) Date: May 4, 2000

(87) PCT Pub. No.: WO00/07992

PCT Pub. Date: Feb. 17, 2000

(30) Foreign Application Priority Data

Aug. 4, 1998 (JP) ............................................. 10-220899

(51) Int. Cl.[7] .................... A61K 31/5415; A61K 31/536
(52) U.S. Cl. ................................ 514/222.2; 514/227.5; 514/231.2
(58) Field of Search ........................... 514/222.2, 231.2, 514/227.5

(56) References Cited

FOREIGN PATENT DOCUMENTS

| EP | 548949 | * | 6/1993 |
| JP | 06025074 | * | 2/1994 |

* cited by examiner

Primary Examiner—Mukund J. Shah
Assistant Examiner—Sudhaker B. Patel
(74) Attorney, Agent, or Firm—Schnader Harrison Segal & Lewis LLP

(57) ABSTRACT

Benzene fused derivatives represented by the following formula:

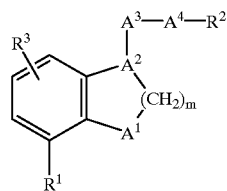

having strong $TXA_2$ receptor antagonistic action and $PGI_2$ receptor agonistic action, and effective for treating or preventing diseases concerning $TXA_2$.

17 Claims, No Drawings

BENZENE FUSED HETEROCYCLIC DERIVATIVES HAVING THROMBOXANE $A_2$ RECEPTOR ANTAGONISTIC ACTIVITY AND PROSTAGLANDIN $I_2$ AGONISTIC ACTIVITY AND APPLICATION THEREOF

TECHNICAL FIELD

The present invention relates to novel benzene fused ring derivatives, and a thromboxane $A_2$ (referred to as "$TXA_2$" hereinafter) receptor antagonist comprising one of the compounds as an active component.

BACKGROUND ART $TXA_2$ discovered by Samuelsson et al in 1975 has strong platelet aggregating action, vascular smooth muscle contracting action and bronchial smooth muscle contracting action (Proc. Natl. Acad. Sci. U.S.A., 72, 2994 (1975)). On the other hand, as a compound having reverse actions, i.e., strong platelet aggregation inhibiting action and vascular relaxing action, prostaglandin $I_2$ ($PGI_2$) is known (Nature, 263, 663 (1976)). Both compounds are synthesized from arachidonic acid in vivo, and it is said that a balance between $TXA_2$ and $PGI_2$ greatly concerns maintenance of the homeostasis of the circulatory system because of the strong actions thereof. Therefore, with the balance shifted to the $TXA_2$ side, phenomena such as activation of the platelets and subsequent thrombogenesis and vascular contraction occur. This is possibly a factor that causes ischemic heart diseases such as angina pectoris, myocardial infarction, etc., and circulatory diseases such as celebrovascular disorder, nephropathy, etc. It is also thought that $TXA_2$ concerns bronchial asthma because of its strong bronchial smooth muscle contracting action. Therefore, in order to treat ischemic heart diseases such as angina pectoris, myocardial infarction, etc., circulatory diseases such as celebrovascular disorder, nephropathy, etc., or bronchial asthma or the like, it is thought to be important to return the off-balance state of $TXA_2$ and $PGI_2$ to the normal state, and a medicine for inhibiting the action of $TXA_2$ or a medicine having the action as a $PGI_2$ receptor agonist is thought to be effective to treat these diseases. As medicines for inhibiting the actions of $TXA_2$ concerning the occurrence of the above-described diseases, $TXA_2$ receptor antagonists have been reported so far (Circulation, 81, Suppl I, I-69 (1990), Medicinal Research Reviews, 11, 503 (1991)). However, conventional $TXA_2$ receptor antagonists exhibit unsatisfactory clinical effects.

An object of the present invention is to provide an excellent $TXA_2$ receptor antagonist having the action as a $PGI_2$ receptor agonist.

DISCLOSURE OF INVENTION

The present invention provides benzene fused heterocyclic derivatives represented by the following formula (I):

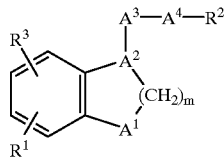

wherein $A^1$ is —$CH_2$—, —O—, —S—, or —$NR^4$—, wherein $R^4$ is hydrogen or alkyl having 1 to 5 carbon atoms;

$A^2$ is —(N—)—$CH_2$, —(N—)—CO—, —(CH—)—, or —(C—)=CH—;

$A^3$ is alkylene having 1 to 4 carbon atoms, alkenylene having 2 to 4 carbon atoms, or alkynylene having 2 to 4 carbon atoms;

$A^4$ is —S(O)$_p$—, —O—, —$CH_2$—, —$NR^5$—, —$NR^5$CO—, or —$CONR^5$—, wherein $R^5$ is hydrogen, alkyl having 1 to 5 carbon atoms, or phenyl (which may be substituted by a group or groups selected from alkyl having 1 to 5 carbon atoms, phenyl, hydroxyl, alkoxy having 1 to 5 carbon atoms, phenoxy, halogen, trifluoromethyl, cyano, nitro, amino, and alkylamino having 1 to 5 carbon atoms), and p is an integer of 0 to 2;

m is an integer of 1 to 3;

$R^1$ is —X—$(CH_2)_n$$COOR^6$ wherein X is —O—, —S—, or —$CH_2$—, $R^6$ is hydrogen, alkyl having 1 to 5 carbon atoms, or an atom or group which gives a pharmacologically acceptable salt, and n is an integer of 1 to 3;

$R^2$ is the following:

(1) —Ar (wherein Ar is phenyl, naphthyl, furyl, or thienyl (wherein phenyl, naphthyl, furyl, or thienyl may be substituted by a group or groups selected from alkyl having 1 to 5 carbon atoms, phenyl, hydroxyl, alkoxy having 1 to 5 carbon atoms, phenoxy, halogen, trifluoromethyl, cyano, nitro, amino, and alkylamino having 1 to 5 carbon atoms); or (2) alkyl having 1 to 5 carbon atoms, alkenyl having 2 to 5 carbon atoms, or alkynyl having 2 to 5 carbon atoms, wherein alkyl, alkenyl, or alkynyl is substituted by one or two Ar (wherein Ar is defined as the same as the above), and may be further substituted by a group or groups selected from —OH, —$CF_3$, and cycloallyl having 3 to 8 carbon atoms);

$R^3$ is hydrogen, halogen, alkyl having 1 to 5 carbon atoms, or alkoxy having 1 to 5 carbon atoms: and either or both of $A^1$ and $A^2$ contain a hetero atom other than carbon. The present invention also provides a $TXA_2$ receptor antagonist containing one of the above compounds of the present invention as an active ingredient.

The compounds of the present invention have strong $TXA_2$ receptor antagonistic action and $PGI_2$ receptor agonistic action, and are effective as medicines for treating or preventing diseases concerning $TXA_2$.

BEST MODE FOR CARRYING OUT THE INVENTION

Of the compounds represented by the above formula (I), compounds represented by the following formula (II) are preferred.

(II)

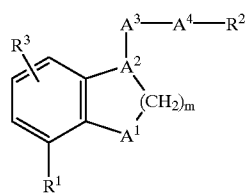

[wherein $R^1$, $R^2$, $R^3$, $A_1$, $A^2$, $A^3$, $A^4$ and m are defined as the same as the above].

Although $R^1$, $R^2$, $R^3$, $R^4$, $R^5$, $R^6$, $A^1$, $A^2$, $A^3$, $A^4$, X, m, n, and Ar in formula (I) or (II) are defined as described above, these groups are described in further detail below.

$R^1$ is —X—$(CH_2)_n$—$COOR^6$ (wherein X is —O—, —S—, or —$CH_2$—, $R^6$ is hydrogen, alkyl having 1 to 5 carbon atoms, or an atom or group which gives a pharmacologically acceptable salt, and n is an integer of 1 to 3). X is particularly preferably —O—, and n is preferably 1 or 2, more preferably 1.

Examples of alkyl $R^6$ having 1 to 5 carbon atoms include methyl, ethyl, propyl, butyl, pentyl, isopropyl, sec-butyl, t-butyl, isobutyl, 1-methylbutyl, 3-methylbutyl, 2,2-dimethylpropyl, and the like.

Examples of pharmacologically acceptable cations of $R^6$ include metal cations, ammonium, amine cations, and quaternary ammonium cations. Preferred examples of metal cations include cations derived from alkali metals, for example, such as lithium, sodium, and potassium, alkali earth metals, for example, such as magnesium and calcium. Of course, the present invention include cations of other metals, for example, such as aluminum, zinc, and iron.

Pharmacologically acceptable amine cations are derived from primary, secondary or tertiary amines. Examples of suitable amines include methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, similar aliphatic, alicyclic or heterocyclic amines having up to 18 carbon atoms, for example, such as 1-methylpiperidine, 4-ethylmorpholine, 1-isopropylpyrolidine, 2-methylpyrolidine, 4-dimethylpiperazine, 2-methylpiperidine, and the like, amines containing water-soluble or hydrophilic groups, for example, such as mono-, di-, or tri-ethanolamine, N-butylethanolamine, 2-amino-1-butanol, 2-amino-2-ethyl-1,3-propanediol, tris(hydroxymethyl)aminomethane, N-phenylethanolamine, N-(p-aminophenyl)diethanolamine, galactamine, N-methylglucamine, N-methylglucosamine, ephedrine, phenylephedrine, epinephrine, procaine, and the like, basic amino acids such as lysine, alginine, and the like.

$R^2$ is preferably alkyl having 1 to 5 carbon atoms, alkenyl having 2 to 5 carbon atoms, or alkynyl having 2 to 5 carbon atoms (alkyl, alkenyl, or alkynyl is substituted by an one or two Ar (Ar is phenyl, naphthyl, furyl, or thienyl (phenyl, naphthyl, furyl, or thienyl may be substituted by a group selected from alkyl having 1 to 5 carbon atoms, phenyl, hydroxyl, alkoxy having 1 to 5 carbon atoms, phenoxy, halogen, trifluoromethyl, cyano, nitro, amino, and alkylamino having 1 to 5 carbon atoms)), and may be further substituted by a group selected from —OH, —$CF_3$, and cycloalkyl having 3 to 8 carbon atoms), more preferably alkyl having 1 to 5 carbon atoms, which is substituted by one or two Ar (Ar is defined as the same as the above). Particularly, alkyl having 1 to 5 carbon atoms, which is substituted by one or two phenyl groups (which may be substituted by a group selected from alkyl having 1 to 5 carbon atoms, phenyl, hydroxyl, alkoxy having 1 to 5 carbon atoms, phenoxy, halogen, trifluoromethyl, cyano, nitro, amino, and alkylamino having 1 to 5 carbon atoms) is preferred, and alkyl having 1 to 5 carbon atoms, which is substituted by two phenyl groups (which may be substituted by a group selected from alkyl having 1 to 5 carbon atoms, phenyl, hydroxyl, alkoxy having 1 to 5 carbon atoms, phenoxy, halogen, trifluoromethyl, cyano, nitro, amino, and alkylamino having 1 to 5 carbon atoms) is more preferred.

Where $R^2$ is alkyl having 1 to 5 carbon atoms, alkenyl having 2 to 5 carbon atoms, or alkynyl having 2 to 5 carbon atoms, which is substituted by two Ar, the two Ar groups may be the same or different.

Of Ar groups, thienyl is 2-thienyl or 3-thienyl, furyl is 2-furyl or 3-furyl, and naphthyl is 1-naphthyl or 2-naphthyl.

Examples of alkyl $R^2$ having 1 to 5 carbon atoms which is substituted by one or two Ar include benzyl, phenethyl, phenylpropyl, phenylbutyl, phenylpentyl, diphenylmethyl, 1,1-diphenylethyl, 2,2-diphenylethyl, 1,3-diphenylpropyl, 3,3-diphenylpropyl, 3,3-diphenyl-2-methylpropyl, 3,3-diphenylbutyl, 1,4-diphenylbutyl, 2,4-diphenylbutyl, 3,4-diphenylbutyl, 4,4-diphenylbutyl, 4,4-diphenyl-2-methylbutyl, 4,4-diphenyl-3-methylbutyl, 4,4-diphenylpentyl, 1,5-diphenylpentyl, 4,5-diphenylpentyl, 5,5-diphenylpentyl, 2-thienylmethyl, 3-thienylmethyl, 2-furylmethyl, 3-furylmethyl, 1-naphthylmethyl, 2-naphthylmethyl, phenyl(2-thienyl)methyl, phenyl(2-furyl)methyl, bis(2-thienyl)methyl, bis(2-furyl)methyl, and the like.

Examples of alkenyl $R^2$ having 2 to 5 carbon atoms which is substituted by one or two Ar include 2-phenylvinyl, 3-phenyl-2-propenyl, 2-phenyl-1-methylvinyl, 4-phenyl-3-butenyl, 5-phenyl-4-pentenyl, 2,2-diphenylvinyl, 3,3-diphenyl-2-propenyl, 3,3-diphenyl-1-propenyl, 4,4-diphenyl-3-butenyl, 1,4-diphenyl-3-butenyl, 2,4-diphenyl-3-butenyl, 3,4-diphenyl-2-butenyl, 4,4-diphenyl-2-butenyl, 4,4-diphenyl-2-methyl-3-butenyl, 4,4-diphenyl-3-methyl-3-butenyl, 5,5-diphenyl-4-pentenyl, 1,5-diphenyl-4-pentenyl, 4,5-diphenyl-3-pentenyl, 4,4-diphenyl-2-pentenyl, 3,3-bis(2-thienyl)-2-propynyl, 3,3-bis(2-furyl)-2-propynyl, 3,3-bis(1-naphthyl)-2-propynyl, and the like.

Examples of alkynyl $R^2$ having 1 to 5 carbon atoms which is substituted by one or two Ar include 3-phenyl-2-propynyl, 4-phenyl-2-butynyl, 5-phenyl-3-pentynyl, 3,3-diphenyl-1-propynyl, 3,3-diphenyl-1-butynyl, 4,4-diphenyl-2-butynyl, 5,5-diphenyl-3-pentynyl, 4,4-bis(2-thienyl)-2-butynyl, 4,4-bis(2-furyl)-2-butynyl, 4,4-bis(1-naphthyl)-2-butynyl, and the like.

A phenyl group, a naphthyl group, a furyl group, or a thienyl group represented by Ar may be substituted by a group selected from alkyl having 1 to 5 carbon atoms, phenyl, hydroxyl, alkoxy having 1 to 5 carbon atoms, phenoxy, halogen, trifluoromethyl, cyano, nitro, amino, and alkylamino having 1 to 5 carbon atoms. Preferred examples of alkyl having 1 to 5 carbon atoms include methyl, ethyl, propyl, isopropyl, butyl, isobutyl, sec-butyl, t-butyl, pentyl, and the like. Preferred examples of alkoxy having 1 to 5 carbon atoms include methoxy, ethoxy, propyloxy, isopropyloxy, butyloxy, isobutyloxy, sec-butyloxy, t-butyloxy, pentyloxy, and the like. Preferred examples of halogen include fluorine, chlorine, bromine, and iodine. Preferred examples of alkylamino having 1 to 5 carbon atoms include methylamino, dimethylamino, ethylamino, diethylamino, diisopropylamino, di-t-butylamino, and the like.

Examples of alkyl $R^3$ having 1 to 5 carbon atoms include methyl, ethyl, propyl, butyl, pentyl, isopropyl, sec-butyl, t-butyl, isobutyl, 1-methylbutyl, 3-methylbutyl, 2,2-dimethylpropyl, and the like. Examples of alkoxy having 1 to 5 carbon atoms include methoxy, ethoxy, propyloxy, isopropyloxy, butyloxy, isobutyloxy, sec-butyloxy, t-butyloxy, pentyloxy, and the like. Examples of halogen include fluorine, chlorine, bromine, and iodine.

$A^1$ is —$CH_2$—, —O—, —S—, or —$NR^4$— (wherein $R^4$ is hydrogen or alkyl having 1 to 5 carbon atoms). Examples of alkyl $R^4$ having 1 to 5 carbon atoms include methyl, ethyl, propyl, butyl, pentyl, isopropyl, sec-butyl, t-butyl, isobutyl, 1-methylbutyl, 3-methylbutyl, 2,2-dimethylpropyl, and the like. $A^1$ is more preferably —$CH_2$— or —O—.

Examples of $A^2$ include —(N—)—CH$_2$—, —(N—)—CO—, —(CH—)—, and —(CH—)=CH— which are respectively represented by the following:

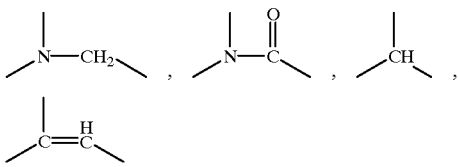

$A^2$ is more preferably —(N—)—CH$_2$— or —(CH—)—.

Examples of alkylene $A^3$ having 1 to 4 carbon atoms include methylene, ethylene, trimethylene, tetramethylene, and the like. Examples of alkenylene $A^3$ having 2 to 4 carbon atoms include vinylene, propenylene, butenylene, and the like. Examples of alkynylene $A^3$ having 2 to 4 carbon atoms include ethynylene, propynylene, butynylene, and the like. Particularly, alkylene having 1 to 4 carbon atoms such as methylene, ethylene, trimethylene, tetramethylene or the like is preferred.

$A^4$ is —S(O)$_p$—, —O—, —CH$_2$—, —NR$^5$—, —NR$^5$CO—, or —CONR$^5$— (wherein R$^5$ is hydrogen, alkyl having 1 to 5 carbon atoms, or phenyl (which may be substituted by a group selected from alkyl having 1 to 5 carbon atoms, phenyl, hydroxyl, alkoxy having 1 to 5 carbon atoms, phenoxy, halogen, trifluoromethyl, cyano, nitro, amino, and alkylamino having 1 to 5 carbon atoms), and p is an integer of 0 to 2). Examples of alkyl R$^5$ having 1 to 5 carbon atoms include methyl, ethyl, propyl, butyl, pentyl, isopropyl, sec-butyl, t-butyl, isobutyl, 1-methylbutyl, 3-methylbutyl, 2,2-dimethylpropyl, and the like.

Of substituents of a phenyl group R$^5_1$ preferred examples of alkyl having 1 to 5 carbon atoms include methyl, ethyl, propyl, isopropyl, butyl, isobutyl, sec-butyl, t-butyl, pentyl, and the like. Preferred examples of alkoxy having 1 to 5 carbon atoms include methoxy, ethoxy, propyloxy, isopropyloxy, butyloxy, isobutyloxy, sec-butyloxy, t-butyloxy, pentyloxy, and the like. Preferred examples of halogen include fluorine, chlorine, bromine, and iodine. Preferred examples of alkylamino having 1 to 5 carbon atoms include methylamino, dimethylamino, ethylamino, diethylamino, diisopropylamino, di-t-butylamino, and the like.

$A^1$ is preferably —S(O)$_p$— (p represents an integer of 0 to 2) or —O—, more preferably —S(O)$_p$— (p represents an integer of 0 to 2).

m is an integer of 1 to 3, preferably 1 or 2, more preferably 1.

Although some compounds represented by the above formula (I) have asymmetric carbon and geometric isomers, the formula (I) of the present invention includes all possible stereo isomers and geometric isomers.

Although some examples of the compounds of the present invention are listed below, the present invention is not limited to these examples.

(1-(4,4-diphenylbutyl)-1,2,3,4-tetrahydroquinolin-5-yloxy)acetic acid
(1-(4,4-diphenylpentyl)-1,2,3,4-tetrahydroquinolin-5-yloxy)acetic acid
(1-(2-(diphenylmethoxy)ethyl)-1,2,3,4-tetrahydroquinolin-5-yloxy)acetic acid
(1-(2-(1,1-diphenylethoxy)ethyl)-1,2,3,4-tetrahydroquinolin-5-yloxy)acetic acid
(1-(2-(benzylthio)ethyl)-1,2,3,4-tetrahydroquinolin-5-yloxy)acetic acid
(1-(2-(1-phenyl-1-methylethylthio)ethyl)-1,2,3,4-tetrahydroquinolin-5-yloxy)acetic acid
(1-(2-(diphenylmethylthio)ethyl)-1,2,3,4-tetrahydroquinolin-5-yloxy)acetic acid
(1-(2-(1,1-diphenylethylthio)ethyl)-1,2,3,4-tetrahydroquinolin-5-yloxy)acetic acid
(1-(3-(diphenylmethylthio)propyl)-1,2,3,4-tetrahydroquinolin-5-yloxy)acetic acid
(1-(3-(1,1-diphenylethylthio)propyl)-1,2,3,4-tetrahydroquinolin-5-yloxy)acetic acid
(1-(2-(2,2-diphenylethylthio)ethyl)-1,2,3,4-tetrahydroquinolin-5-yloxy)acetic acid
(1-(2-(2,2-diphenylpropylthio)ethyl)-1,2,3,4-tetrahydroquinolin-5-yloxy)acetic acid
(1-(2-(2,2,2-trifluoro-1,1-diphenylethylthio)ethyl)-1,2,3,4-tetrahydroquinolin-5-yloxy)acetic acid
(1-(2-(diphenylmethylsulfinyl)ethyl)-1,2,3,4-tetrahydroquinolin-5-yloxy)acetic acid
(1-(2-(1,1-diphenylethylsulfinyl)ethyl)-1,2,3,4-tetrahydroquinolin-5-yloxy)acetic acid
(1-(2-(diphenylmethylsulfonyl)ethyl)-1,2,3,4-tetrahydroquinolin-5-yloxy)acetic acid
(1-(2-(1,1-diphenylethylsulfonyl)ethyl)-1,2,3,4-tetrahydroquinolin-5-yloxy)acetic acid
(1-(3-diphenylamino-3-oxopropyl)-1,2,3,4-tetrahydroquinolin-5-yloxy)acetic acid
(1-(4-diphenylamino-3-oxobutyl)-1,2,3,4-tetrahydroquinolin-5-yloxy)acetic acid
(1-(2-((diphenylmethyl)amino)ethyl)-1,2,3,4-tetrahydroquinolin-5-yloxy)acetic acid
(1-(2-((1,1-diphenylethyl)amino)ethyl)-1,2,3,4-tetrahydroquinolin-5-yloxy)acetic acid
(1-(2-(diphenylamino)ethyl)-1,2,3,4-tetrahydroquinolin-5-yloxy)acetic acid
(1-(3-(diphenylamino)propyl)-1,2,3,4-tetrahydroquinolin-5-yloxy)acetic acid
(1-(4-(diphenylamino)butyl)-1,2,3,4-tetrahydroquinolin-5-yloxy)acetic acid
3-(1-(2-(diphenylmethylthio)ethyl)-1,2,3,4-tetrahydroquinolin-5-yl)propionic acid
4-(1-(2-(diphenylmethylthio)ethyl)-1,2,3,4-tetrahydroquinolin-5-yl)butyric acid
3-(1-(2-(1,1-diphenylethylthio)ethyl)-1,2,3,4-tetrahydroquinolin-5-yl)propionic acid
4-(1-(2-(1,1-diphenylethylthio)ethyl)-1,2,3,4-tetrahydroquinolin-5-yl)butyric acid
(1-(2-(diphenylmethylthio)ethyl)-2,3,4,5-tetrahydro-1H-1-benzazepin-6-yloxy)acetic acid
(1-(2-(1,1-diphenylethylthio)ethyl)-2,3,4,5-tetrahydro-1H-1-benzazepin-6-yloxy)acetic acid
(2-oxo-1-(2-(diphenylmethylthio)ethyl)-1,2,3,4-tetrahydroquinolin-5-yloxy)acetic acid
(2-oxo-1-(2-(1,1-diphenylethylthio)ethyl)-1,2,3,4-tetrahydroquinolin-5-yloxy)acetic acid
(2-oxo-1-(2-(diphenylmethylthio)ethyl)-2,3,4,5-tetrahydro-1H-1-benzazepin-6-yloxy)acetic acid
(2-oxo-1-(2-(1,1-diphenylethylthio)ethyl)-2,3,4,5-tetrahydro-1H-1-benzazepin-6-yloxy)acetic acid
(4-(4,4-diphenylbutyl)-3,4-dihydro-2H-1,4-benzoxazin-8-yloxy)acetic acid
(4-(4,4-diphenylpentyl)-3,4-dihydro-2H-1,4-benzoxazin-8-yloxy)acetic acid
(4-(2-(diphenylmethoxy)ethyl)-3,4-dihydro-2H-1,4-benzoxazin-8-yloxy)acetic acid
(4-(2-(1,1-diphenylethoxy)ethyl)-3,4-dihydro-2H-1,4-benzoxazin-8-yloxy)acetic acid
(4-(2-(benzylthio)ethyl)-3,4-dihydro-2H-1,4-benzoxazin-8-yloxy)acetic acid
(4-(2-(1-phenyl-1-methylethylthio)ethyl)-3,4-dihydro-2H-1,4-benzoxazin-8-yloxy)acetic acid (4-(2-(diphenylmethylthio)ethyl)-3,4-dihydro-2H-1,4-benzoxazin-8-yloxy)acetic acid
(4-(2-(1,1-diphenylethylthio)ethyl)-3,4-dihydro-2H-1,4-benzoxazin-8-yloxy)acetic acid
(4-(3-(diphenylmethylthio)propyl)-3,4-dihydro-2H-1,4-benzoxazin-8-yloxy)acetic acid
(4-(3-(1,1-diphenylethylthio)propyl)-3,4-dihydro-2H-1,4-benzoxazin-8-yloxy)acetic acid
(4-(2-(2,2-diphenylethylthio)ethyl)-3,4-dihydro-2H-1,4-benzoxazin-8-yloxy)acetic acid
(4-(2-(2,2-diphenylpropylthio)ethyl)-3,4-dihydro-2H-1,4-benzoxazin-8-yloxy)acetic acid
(4-(2-(2,2,2,-trifluoro-1,1-diphenylethylthio)ethyl)-3,4-dihydro-2H-1,4-benzoxazin-8-yloxy)acetic acid
(4-(2-(diphenylmethylsulfinyl)ethyl)-3,4-dihydro-2H-1,4-benzoxazin-8-yloxy)acetic acid
(4-(2-(1,1-diphenylethylsulfinyl)ethyl)-3,4-dihydro-2H-1,4-benzoxazin-8-yloxy)acetic acid
(4-(2-(diphenylmethylsulfonyl)ethyl)-3,4-dihydro-2H-1,4-benzoxazin-8-yloxy)acetic acid
(4-(2-(1,1-diphenylethylsulfonyl)ethyl)-3,4-dihydro-2H-1,4-benzoxazin-8-yloxy)acetic acid
(4-(3-diphenylamino-3-oxopropyl)-3,4-dihydro-2H-1,4-benzoxazin-8-yloxy)acetic acid
(4-(4-diphenylamino-3-oxobutyl)-3,4-dihydro-2H-1,4-benzoxazin-8-yloxy)acetic acid
(4-(2-((diphenylmethyl)amino)ethyl)-3,4-dihydro-2H-1,4-benzoxazin-8-yloxy)acetic acid
(4-(2-((1,1-diphenylethyl)amino)ethyl)-3,4-dihydro-2H-1,4-benzoxazin-8-yloxy)acetic acid
(4-(2-(diphenylamino)ethyl)-3,4-dihydro-2H-1,4-benzoxazin-8-yloxy)acetic acid
(4-(3-(diphenylamino)propyl)-3,4-dihydro-2H-1,4-benzoxazin-8-yloxy)acetic acid
(4-(4-(diphenylamino)butyl)-3,4-dihydro-2H-1,4-benzoxazin-8-yloxy)acetic acid
3-(4-(2-(diphenylmethylthio)ethyl)-3,4-dihydro-2H-1,4-benzoxazin-5-yl)propionic acid
4-(4-(2-(diphenylmethylthio)ethyl)-3,4-dihydro-2H-1,4-benzoxazin-5-yl)butyric acid
3-(4-(2-(1,1-diphenylethylthio)ethyl)-3,4-dihydro-2H-1,4-benzoxazin-5-yl)propionic acid
4-(4-(2-(1,1-diphenylethylthio)ethyl)-3,4-dihydro-2H-1,4-benzoxazin-5-yl)butyric acid
(5-(2-(diphenylmethylthio)ethyl)-2,3,4,5-tetrahydro-1,5-benzoxazepin-9-yloxy)acetic acid
(5-(2-(1,1-diphenylethylthio)ethyl)-2,3,4,5-tetrahydro-1H-1-benzoxazepin-9-yloxy)acetic acid
(3-oxo-4-(2-(diphenylmethylthio)ethyl)-3,4-dihydro-2H-1,4-benzoxazin-8-yloxy)acetic acid
(3-oxo-4-(2-(1,1-diphenylethylthio)ethyl)-3,4-dihydro-2H-1,4-benzoxazin-8-yloxy)acetic acid
(4-oxo-5-(2-(diphenylmethylthio)ethyl)-2,3,4,5-tetrahydro-1,5-benzoxazepin-9-yloxy)acetic acid
(4-oxo-5-(2-(1,1-diphenylethylthio)ethyl)-2,3,4,5-tetrahydro-1H-1-benzoxazepin-9-yloxy)acetic acid
(4-(2-(diphenylmethylthio)ethyl)-3,4-dihydro-2H-1,4-benzothiazin-8-yloxy)acetic acid
(4-(2-(1,1-diphenylethylthio)ethyl)-3,4-dihydro-2H-1,4-benzothiazin-8-yloxy)acetic acid
(1-(2-(diphenylmethylthio)ethyl)-1,2,3,4-tetrahydro-1,4-diazin-5-yloxy)acetic acid
(1-(2-(1,1-diphenylethylthio)ethyl)-1,2,3,4-tetrahydro-1,4-diazin-8-yloxy)acetic acid
(3-(4,4-diphenylbutyl)-2,3-dihydrobenzofuran-7-yloxy) acetic acid
(3-(4,4-diphenylpentyl)-2,3-dihydrobenzofuran-7-yloxy) acetic acid
(3-(2-(diphenylmethoxy)ethyl)-2,3-dihydrobenzofuran-7-yloxy) acetic acid
(3-(2-(1,1-diphenylethoxy)ethyl)-2,3-dihydrobenzofuran-7-yloxy)acetic acid
(3-(2-(benzylthio)ethyl)-2,3-dihydrobenzofuran-7-yloxy) acetic acid
(3-(2-(1-diphenyl-1-methylethylthio)ethyl)-2,3-dihydrobenzofuran-7-yloxy)acetic acid
(3-(2-(diphenylmethylthio)ethyl)-2,3-dihydrobenzofuran-7-yloxy)acetic acid
(3-(2-(1,1-diphenylethylthio)ethyl)-2,3-dihydrobenzofuran-7-yloxy)acetic acid
(3-(3-(diphenylmethylthio)propyl)-2,3-dihydrobenzofuran-7-yloxy)acetic acid
(3-(3-(1,1-diphenylethylthio)propyl)-2,3-dihydrobenzofuran-7-yloxy)acetic acid
(3-(2-(2,2-diphenylethylthio)ethyl)-2,3-dihydrobenzofuran-7-yloxy)acetic acid
(3-(2-(2,2-diphenylpropylthio)ethyl)-2,3-dihydrobenzofuran-7-yloxy)acetic acid
(3-(2-(2,2,2-trifluoro-1,1-diphenylethylthio)ethyl)-2,3-dihydrobenzofuran-7-yloxy)acetic acid
(3-(2-(diphenylmethylsulfinyl)ethyl)-2,3-dihydrobenzofuran-7-yloxy)acetic acid
(3-(2-(1,1-diphenylethylsulfinyl)ethyl)-2,3-dihydrobenzofuran-7-yloxy)acetic acid
(3-(2-(diphenylmethylsulfonyl)ethyl)-2,3-dihydrobenzofuran-7-yloxy)acetic acid
(3-(2-(1,1-diphenylethylsulfonyl)ethyl)-2,3-dihydrobenzofuran-7-yloxy)acetic acid
(3-(3-diphenylamino-3-oxopropyl)-2,3-dihydrobenzofuran-7-yloxy)acetic acid
(3-(4-diphenylamino-3-oxobutyl)-2,3-dihydrobenzofuran-7-yloxy)acetic acid
(3-(2-((diphenylmethyl)amino)ethyl)-2,3-dihydrobenzofuran-7-yloxy)acetic acid
(3-(2-((1,1-diphenylethyl)amino)ethyl)-2,3-dihydrobenzofuran-7-yloxy)acetic acid
(3-(2-(diphenylamino)ethyl)-2,3-dihydrobenzofuran-7-yloxy)acetic acid
(3-(3-(diphenylamino)propyl)-2,3-dihydrobenzofuran-7-yloxy)acetic acid
(3-(4-(diphenylamino)butyl)-2,3-dihydrobenzofuran-7-yloxy)acetic acid
3-(3-(2-(diphenylmethylthio)ethyl)-2,3-dihydrobenzofuran-7-yl)propionic acid
4-(3-(2-(diphenylmethylthio)ethyl)-2,3-dihydrobenzofuran-7-yl)butyric acid
3-(3-(2-(1,1-diphenylethylthio)ethyl)-2,3-dihydrobenzofuran-7-yl)propionic acid
4-(3-(2-(1,1-diphenylethylthio)ethyl)-2,3-dihydrobenzofuran-7-yl)butyric acid
(4-(2-(diphenylmethylthio)ethyl)-chroman-8-yloxy)acetic acid
(4-(2-(1,1-diphenylethylthio)ethyl)-chroman-8-yloxy)acetic acid
(4-(2-(diphenylmethylthio)ethyl)-2H-chromen-8-yloxy) acetic acid
(4-(2-(1,1-diphenylethylthio)ethyl)-2H-chromen-8-yloxy) acetic acid The present invention includes methyl esters, ethyl esters, propyl esters, isopropyl esters, butyl esters, t-butyl esters, pentyl esters, and the like of the above compounds.

Although examples of methods of producing the compounds included in the present invention will be described below, the present invention is not limited to these examples.

Of the compounds of the present invention, compounds in which $A^4$ is —S— and X is —O— can be synthesized by production method A.

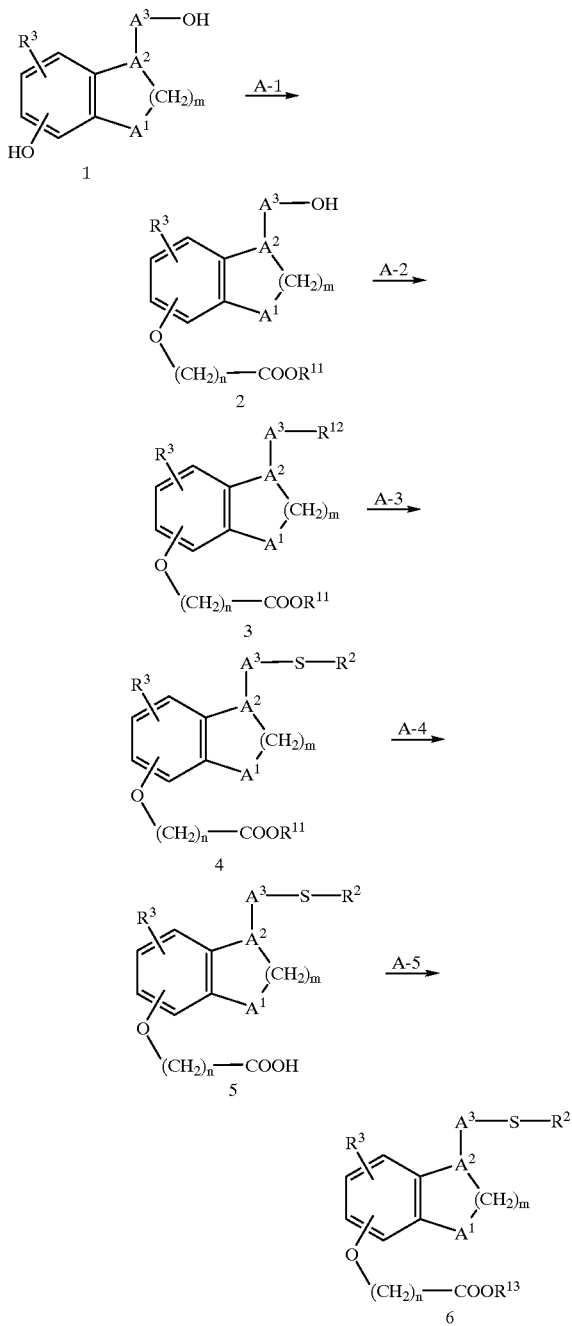

Production method A (wherein $A^1$, $A^2$, $A^3$, $R^2$, $R^3$, and m are defined as the same as the above, $R^{11}$ represents alkyl having 1 to 5 carbon atoms, $R^{12}$ represents p-toluenesulfonyloxy, methanesulfonyloxy, chlorine, bromine, or iodine, $R^{13}$ represents a metal cation such as lithium, sodium, potassium, or the like, or an amine cation such as an ammonium ion, a monoethanolammonium ion, a diethanolammonium ion, triethanolammonium ion, a N-methylgulcamium ion, an ephedrium ion, or the like, and n represents an integer of 1 to 3).

Step A-1 is the step of introducing an ester unit. This step is carried out by removing a proton of a phenolic hydroxyl group by using a base, and then reacting the product with the following compound:

$Br(CH_2)_n COOR^{11}$ or $Cl(CH_2)_n COOR^{11}$ (wherein $R^{11}$ and n are defined as the same as the above). As the base, potassium carbonate, potassium t-butoxide, potassium hydroxide, sodium hydroxide, sodium hydride, or the like is used. As a solvent, methanol, ethanol, DMF, DMSO, THF, DME, or the like is used. The reaction temperature is selected from −50 to 150° C., and is preferably 0 to 50° C. The reaction time is 1 minute to 120 hours, and is usually 5 minutes to 50 hours.

Step A-2 is the step of converting a hydroxyl group into a leaving group such as p-toluenesulfonyloxy, methanesulfonyloxy, bromine, or the like. Where $R^{12}$ is p-toluenesulfonyloxy or methanesulfonyloxy, the conversion can be performed by conventional tosylation or mesylation. Namely, the step can be carried out by reaction with p-toluenesulfonyl chloride or methanesulfonyl chloride in coexistence with a base such as triethylamine, diisopropylamine, pyridine, or the like. As a solvent, THF, DME, dioxane, benzene, toluene, dichloromethane, DMF, or the like is preferably used, and a base such as pyridine or the like may be used as the solvent. The reaction temperature is selected from −80 to 150° C., and is preferably −20 to 50° C. The reaction time is 1 minute to 80 hours, and is usually 5 minutes to 30 hours. Where $R^{12}$ is bromine, the conversion is carried out by reaction with a brominating agent such as triphenylphosphine+carbon tetrabromide, triphenylphosphine+N-bromosuccimide, or the like. As a solvent, THF, DME, dichloromethane, or the like is used. The reaction temperature is selected from −80 to 150° C., and is preferably −20 to 50° C. The reaction time is 1 minute to 80 hours, and is usually 5 minutes to 30 hours.

Step A-3 is the step of thioetherifying compound 3. This step is carried out by reacting compound 3 with a sodium or potassium salt of $R^2$—SH ($R^2$ is defined as the same as the above) which has previously been prepared. A sodium or potassium salt of $R^2$—SH can be obtained by reacting $R^2$—SH with a base such as sodium hydride, sodium carbonate, sodium t-butoxide, potassium hydride, potassium carbonate, potassium t-butoxide, or the like. As a solvent, THF, DME, DMF, or the like is used. The reaction temperature is selected from −80 to 150° C., and is preferably −20 to 50° C. The reaction time is 1 minute to 80 hours, and is usually 5 minutes to 30 hours. The step can also be carried out by adding a base such as potassium carbonate or the like to a solution mixture containing compound 3 and $R^2$—SH.

Step A-4 is the step of ester hydrolysis of compound 4. Hydrolysis reaction is carried out by reacting ester 4 with a base in a solvent such as aqueous methanol, aqueous ethanol, aqueous tetrahydrofuran, or the like. As the base, a base such as sodium hydroxide, potassium hydroxide, potassium carbonate, or the like is preferably used. The reaction temperature is selected from −20 to 150° C., but a preferred reaction rate can be obtained at 0 to 50° C. The reaction time is 1 minute to 120 hours, and is usually 5 minutes to 50 hours. The hydrolysis reaction can also be carried out by reacting compound 4 with a metal salt of a thiol in DMF or DMSO.

Step A-5 is the step of forming a salt of compound 5. Reaction forming salt is carried out by reacting carboxylic acid 5 with a hydroxide of a metal cation or an amine. As a solvent, water, methanol, ethanol, tetrahydrofuran, ethyl acetate, or the like can be used. The reaction temperature is selected from −50 to 150° C., and is preferably 0 to 80° C. The reaction time is 1 minute to 120 hours, and is usually 1 minute to 30 hours.

Of the compounds of the present invention, compounds in which $A^4$ is —S(O)$_p$— wherein p is 1, and X is —O— can be synthesized by production method B.

Production method B

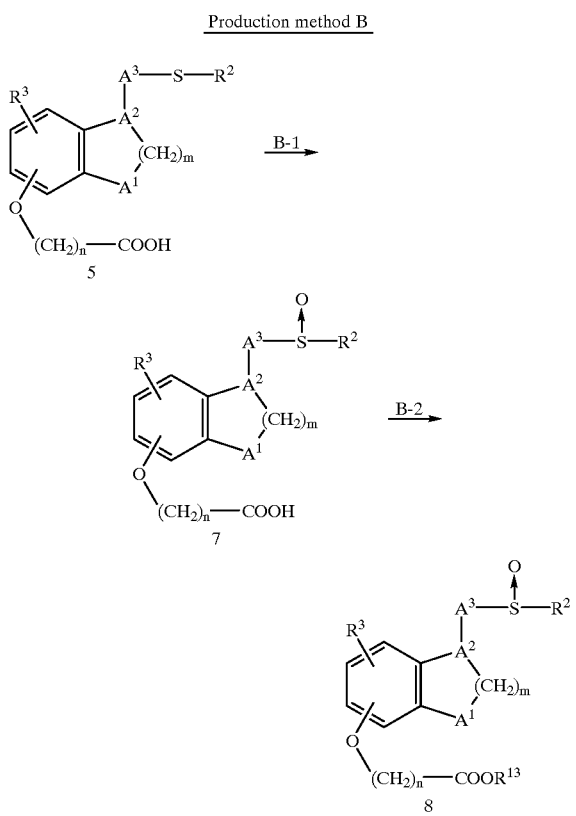

(wherein $A^1$ $A^2$, $A^3$, $R^2$, $R^3$, m, n, and $R^{13}$ are defined as the same as the above).

Of Step B-1 is the step of oxidizing compound 5. Oxidation step is carried out by reacting sulfide 5 with an oxidizing agent. As the oxidizing agent, m-chloroperbenzoic acid, perbenzoic acid, peracetic acid, hydrogen peroxide solution, or the like is preferably used. As a solvent, carbon tetrachloride, chloroform, dichloromethane, water, acetic acid, methanol, ethanol, or the like is used. The reaction temperature is selected from −50 to 150° C., and is preferably 0 to 100° C. The reaction time is 1 minute to 120 hours, and is usually 1 minute to 30 hours.

Step B-2 is the step of forming a salt of compound 7. This step is carried out by the same method as step A-5.

Of the compounds of the present invention, compounds in which $A^1$ is —O—, $A^2$ is —(N—)—CH$_2$—, $A^3$ is straight chain alkyl having 2 to 4 carbon atoms, $A^4$ is —S—, and X is —O— can be produced by production method C.

Step C-1 is the step of nitrating compound 9. Nitration reaction is carried out by reacting phenol 9 with a nitrating agent. As the nitrating agent, nitric acid, acetic anhydride-nitric acid mixture, a nitric acid-sulfuric acid mixture, a trifluoroacetic anhydride -nitric acid mixture, potassium nitrate-trifluoroacetic acid, fuming nitric acid, or the like is preferably used. As a solvent, ethyl acetate, nitromethane, dimethoxyethane, acetic acid, trifluoroacetic acid, methanol, ethanol, water, or the like is used. The reaction temperature is selected from −50 to 150° C., and is preferably −10 to 50° C. The reaction time is 1 minute to 120 hours, and is usually 1 minute to 30 hours.

Step C-2 is the step of introducing an ester unit in compound 10. This step is carried out by removing a proton of a phenolic hydroxyl group by using a base, and then reacting the product with the following compound:

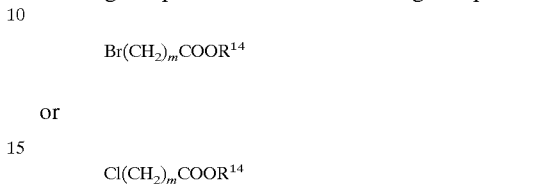

(wherein $R^{14}$ and m are defined as the same as the above). As the base, potassium carbonate, potassium t-butoxide, potassium hydroxide, sodium hydroxide, sodium hydride, or the like is used. As a solvent, methanol, ethanol, DMF, DMSO, THF, DME, or the like is used. The reaction temperature is selected from −50 to 150° C., and is preferably to 50° C. The reaction time is 1 minute to 120 hours, and usually 5 minutes to 50 hours.

Production method C

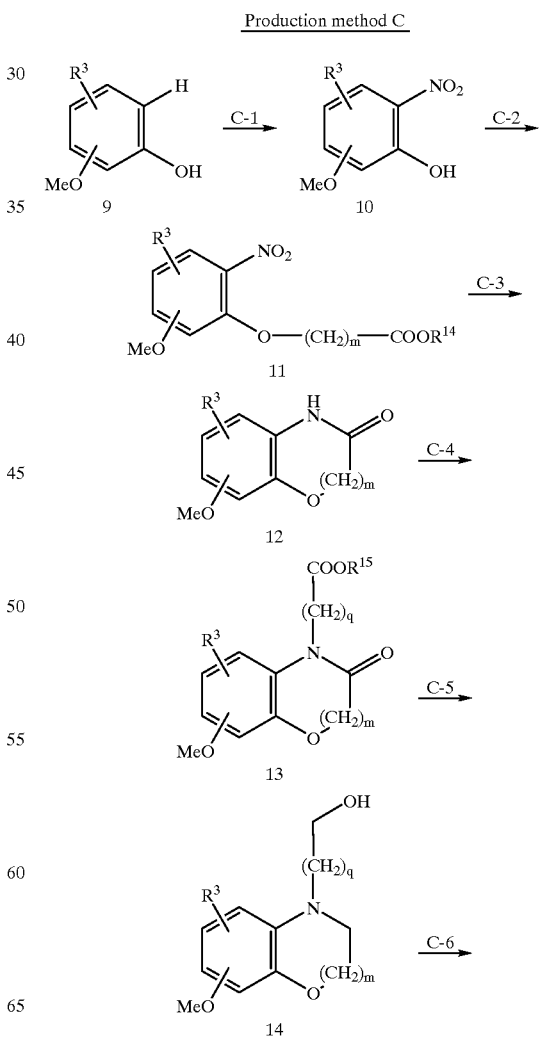

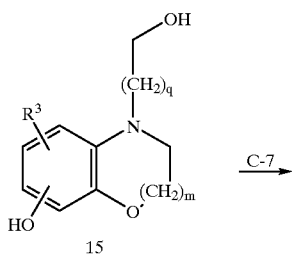

15

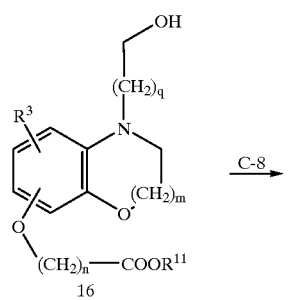

16

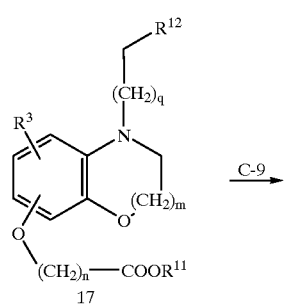

17

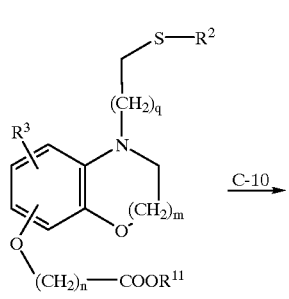

18

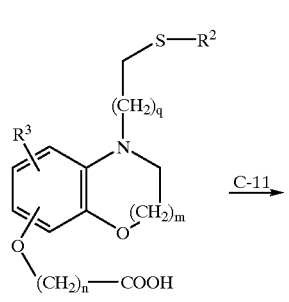

19

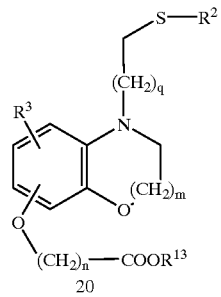

20

(wherein $R^2$, $R^3$, m, n, $R^{11}$, $R^{12}$, and $R^{13}$ are defined as the same as the above, $R^{14}$ represents alkyl having 1 to 5 carbon atoms, $R^{15}$ represents alkyl having 1 to 5 carbon atoms, and q represents an integer of 1 to 3).

Step C-3 is the step of reducing and cyclizing compound 11. This step is carried out by the method of catalytically hydrogenating nitro compound 11 or the method of reducing it with a metal reducing agent. The catalytic hydrogenation preferably uses hydrogen gas, formic acid, ammonium formate, sodium formate, or the like as a hydrogen source, and palladium carbon, platinum, platinum oxide, platinum carbon, palladium acetate, a tetrakistriphenylphosphine palladium complex, or the like as a catalyst. As a reaction additive, hydrochloric acid, sulfuric acid, ammonium chloride, activated carbon, iron powder, zinc powder, or the like may be used. The reduction method using the metal reducing agent preferably uses iron, zinc, tin, or the like as the reducing agent. As a solvent, ethyl acetate, acetic acid, trifluoroacetic acid, methanol, ethanol, water, tetrahydrofuran, dimethoxyethane, or the like is preferably used. As a reaction additive, hydrochloric acid, sulfuric acid, ammonium chloride, activated carbon, an iron powder, a zinc powder, or the like may be further used. The reaction temperature is selected from −50 to 150° C., and is preferably 0 to 120° C. The reaction time is 1 minute to 120 hours, and is usually 1 minute to 30 hours. Where $R^3$ is bromine, in some cases, the use of the catalytic hydrogenation method as the reduction method occurs conversion of bromine in $R^3$ into hydrogen.

Step C-4 is the step of introducing an ester unit in compound 12. This step is carried out by removing a proton of amido by using a base, and then reacting the product with the following compound:

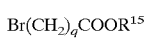

or

(wherein $R^{15}$ and q are defined as the same as the above). As the base, potassium carbonate, potassium t-butoxide, potassium hydroxide, sodium hydroxide, sodium hydride, or the like is used. As a solvent, methanol, ethanol, DMF, DMSO, THF, DME, or the like is used. The reaction temperature is selected from −50 to 150° C., and is preferably 0 to 50° C. The reaction time is 1 minute to 120 hours, and is usually 5 minutes to 50 hours.

Step C-5 is the step of reducing ester and amido of compound 13. The reduction is carried out by reacting compound 13 with a reducing agent. As the reducing agent, borane, a borane-tetrahydrofuran complex, a borane-dimethylsulfide complex, a sodium borohydride-boron trifluoride ether complex, a sodium borohydride-boron trifluoride tetrahydrofuran complex, or the like is preferably used. As a solvent, tetrahydrofuran, dimethoxyethane, or the like is preferably used. The reaction temperature is selected from −50 to 150° C., and is preferably 0 to 120° C. The reaction time is 1 minute to 120 hours, and is usually 1 minute to 30 hours.

Step C-6 is the step of demethylating compound 14. This step is carried out by reacting methyl ether 14 with a Lewis acid or protonic acid. As a Lewis acid, boron tribromide, boron trifluoride, boron trichloride, aluminum chloride, aluminum bromide, iron chloride, iron bromide, zinc chloride, phosphorus tribromide, or the like is preferably used. As a protonic acid, hydrochloric acid, sulfuric acid, hydrobromic acid, hydroiodic acid, methanesulfonic acid, trifluoromethansulfonic acid, benzenesulfonic acid, p-toluenesulfonic acid, hydrobromic acid-lithium chloride, hydrobromic acid-lithium bromide, or the like is preferably used. As a solvent, dichloromethane, chloroform, carbon tetrachloride, water, or the like is preferably used. The reaction temperature is selected from −50 to 150° C., and is preferably −10 to 120° C. The reaction time is 1 minute to 120 hours, and is usually 1 minute to 30 hours.

Step C-7 is the step of introducing an ester unit into compound 15. This step is carried out by the same method as step A-1.

Step C-8 is the step of converting a hydroxyl group of compound 16 to a leaving group. This step is carried out by the same method as step A-2.

Step C-9 is the step of thioetherifying compound 17. This step is carried out by the same method as step A-3.

Step C-10 is the step of ester hydrolysis of compound 18. This step is carried out by the same method as step A-4.

Step C-11 is the step of forming a salt of compound 19. This step is carried out by the same method as step A-5.

If Of the compounds of the present invention, compounds in which $A^2$ is —(N—)—$CH_2$— and X is —O— can be produced by production method D.

Production method D

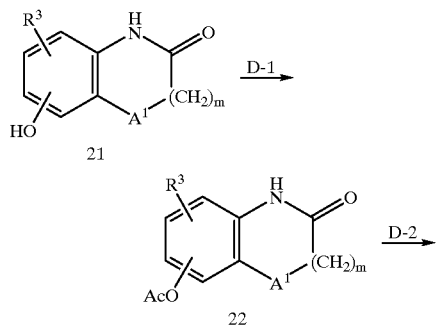

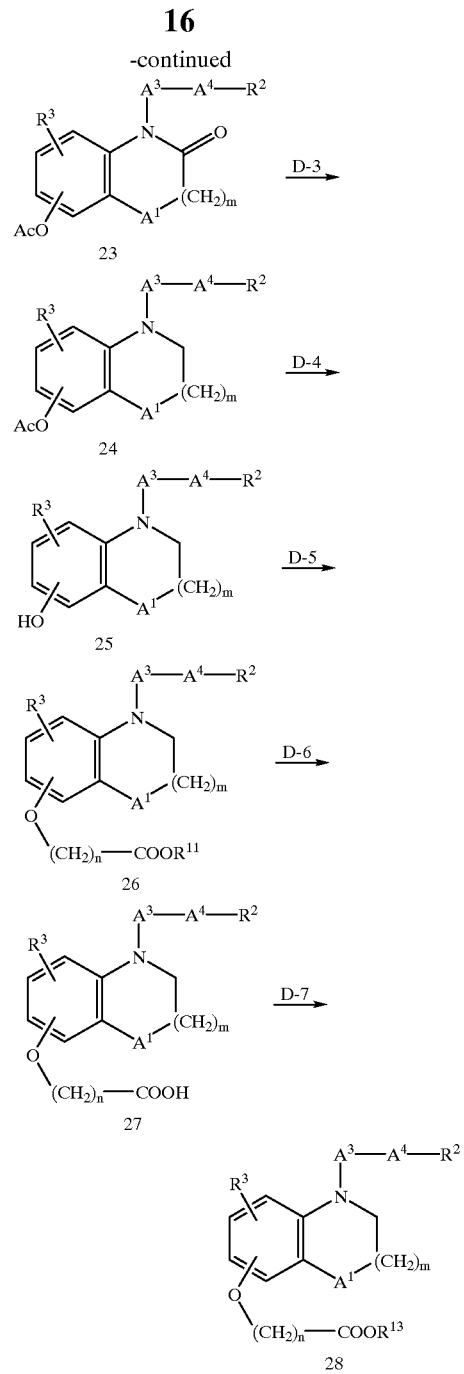

(wherein $A^1$, $A^3$, $A^4$, $R^2$, $R^3$, m, n, $R^{11}$, $R^{12}$ and $R^{13}$ are defined as the same as the above).

Step D-1 is the step of protecting a phenolic hydroxyl group by an acetyl group. This step is carried out by reacting phenol 21 with acetic anhydride or acetyl chloride in the presence of an appropriate base. As the base, pyridine, triethylamine, or the like is used. As a solvent, THF, DME, benzene, toluene, or the like is used, and pyridine may be used as the solvent. The reaction temperature is selected from −50 to 150° C., and is preferably 0 to 50° C. The reaction time is 1 minute to 120 hours, and is usually 5 minutes to 50 hours.

Step D-2 is the step of alkylating amido. Alkylation is carried out by reacting compound 22 with a base, and then reacting the product with the following compound:

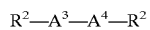

(wherein $R^2$, $R^{12}$, $A^3$ and $A^4$ are defined as the same as the above). As the base, sodium hydride, potassium hydride, sodium carbonate, potassium carbonate, potassium t-butoxide, sodium t-butoxide, or the like is used. As a solvent, methanol, ethanol, DMF, DMSO, THF, DME, or the like is used. The reaction temperature is selected from −50 to 150° C., and is preferably 0 to 50° C. The reaction time is 1 minute to 120 hours, and is usually 5 minutes to 50 hours.

Step D-3 is the step of reducing amido. This step is carried out by bubbling diborane through a solution of compound 23, or adding a borane-THF solution thereto. As a solvent, THF, DME, or the like is used. The reaction temperature is selected from −50 to 150° C., and is preferably −20 to 50° C. The reaction time is 1 minute to 120 hours, and is usually 5 minutes to 50 hours.

Step D-4 is the step of removing an acetyl group. This step is carried out by dissolving compound 24 in methanol, ethanol, or the like, and then adding an appropriate base to the resultant solution. As the base, potassium carbonate, sodium methoxide, potassium methoxide, sodium hydroxide, potassium hydroxide, or the like is preferably used. The reaction temperature is selected from −50 to 150° C., and is preferably 0 to 50° C. The reaction time is 1 minute to 80 hours, and is usually 5 minutes to 30 hours.

Step D-5 is the step of introducing an ester unit into compound 25. This step is carried out by the same method as step A-1.

Step D-6 is the step of ester hydrolysis of compound 26. This step is carried out by the same method as step A-4.

Step D-7 is the step of forming a salt of compound 27. This step is carried out by the same method as step A-5.

Of the compounds of the present invention, compounds in which $A^2$ is —(N—)—CH$_2$—, $A^3$ is straight chain alkylene having 2 to 4 carbon atoms, $A^4$ is —S—, and X is —O— can be synthesized by production method E.

Production method E

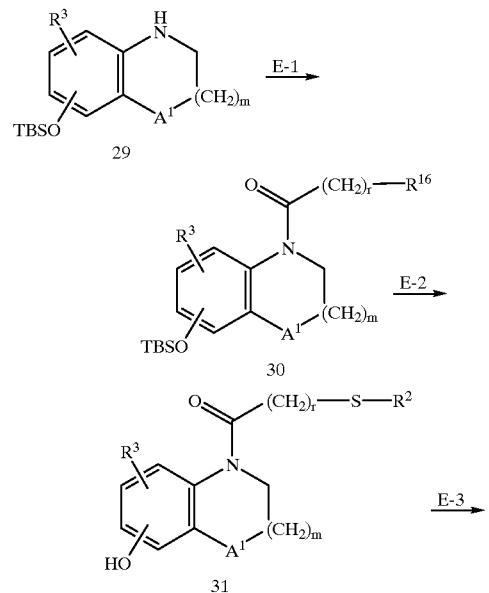

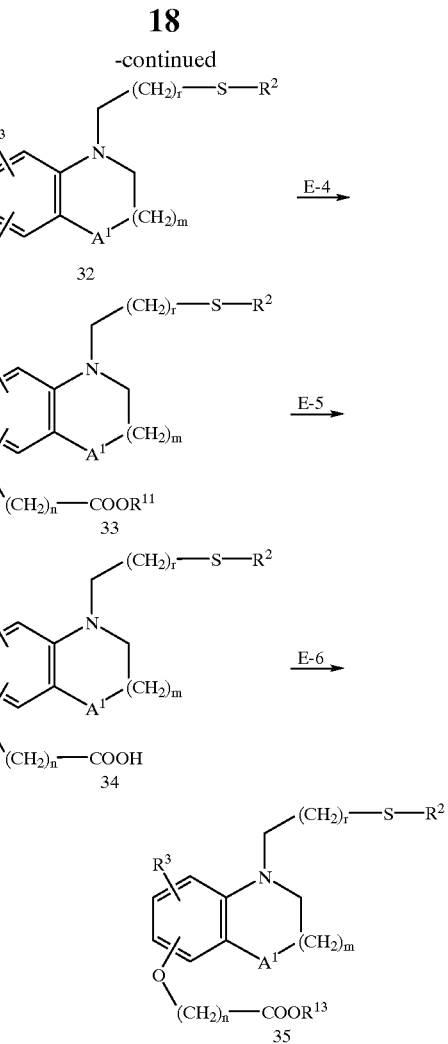

(wherein $A^1$, $R^2$, $R^3$, m, $R^{11}$, and $R^{13}$ are defined as the same as the above, $R^{16}$ represents chlorine, bromine, or iodine, r represents an integer of 1 to 3, and TBS represents a t-butyldimethylsilyl group).

Step E-1 is the step of acylating compound 29. This step is carried out by reacting compound 29 with the following acid chloride in the presence of an appropriate base:

$$R^{16}(CH_2)_rCOCl$$

(wherein $R^{16}$ and r are defined as the same as the above). As the base, pyridine, triethylamine, or the like is used. As a solvent, methylene chloride, THF, DME, or the like is used. The reaction temperature is selected from −80 to 150° C., and is preferably −20 to 50° C. The reaction time is 1 minute to 80 hours, and is usually 5 minutes to 30 hours. This step can also be carried out by reacting compound 29 with the following acid anhydride in the presence of an appropriate base:

$$(R^{16}(CH_2)_rCO)_2O$$

(wherein $R^{16}$ and r are defined as the same as the above). As a solvent, methylene chloride, THF, DME, or the like is used. The reaction temperature is selected from −50 to 150° C., and is preferably 0 to 50° C. The reaction time is 1 minute to 120 hours, and is usually 5 minutes to 50 hours.

Step E-2 is the step of thioetherifying compound 30. This step is carried out by reacting compound 30 with a sodium or potassium salt of $R^2$—SH ($R^2$ is defined as the same as the above) which has previously been prepared. The sodium or potassium salt of $R^2$—SH can be obtained by reacting $R^2$—SH with a base such as sodium hydride, sodium carbonate, sodium t-butoxide, potassium hydride, potassium carbonate, potassium t-butoxide, or the like. As a solvent, THF, DME, DMF, or the like is used. The reaction temperature is selected from −50 to 150° C., and is preferably −20 to 100° C. The reaction time is 1 minute to 120 hours, and is usually 5 minutes to 50 hours. The step can also be carried out by adding a base such as potassium carbonate or the like to a solution of a mixture containing compound 30 and $R^2$—SH. In this step, a t-butyldimethylsilyl group is simultaneously removed.

Step E-3 is the step of reducing amido of compound 31. This step is carried out by the same method as step D-3.

Step E-4 is the step of introducing an ester unit into compound 32. This step is carried out by the same method as step A-1.

Step E-5 is the step of ester hydrolysis of compound 33. This step is carried out by the same method as step A-4.

Step E-6 is the step of forming a salt of compound 34. This step is carried out by the same method as step A-5.

Of the compounds of the present invention, compounds in which $A^1$ is —O—, $A^2$ is —(N—)—CH$_2$—, $A^3$ is straight chain alkylene having 1 to 4 carbon atoms, $R^3$ is hydrogen, and X is —O— can be produced by production method F.

Production method F

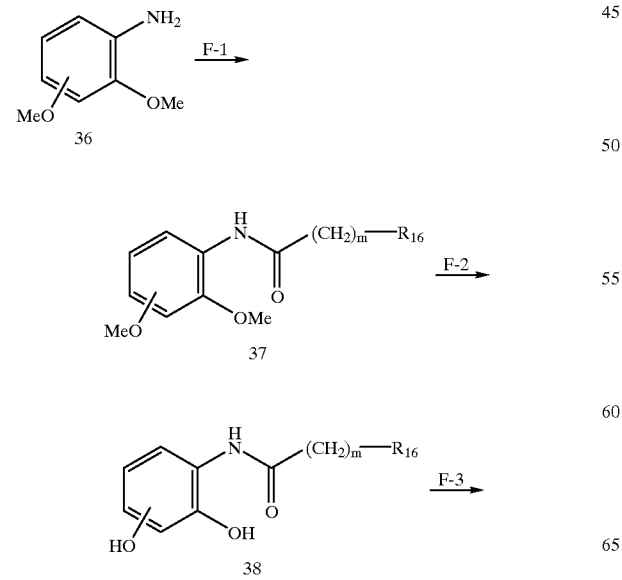

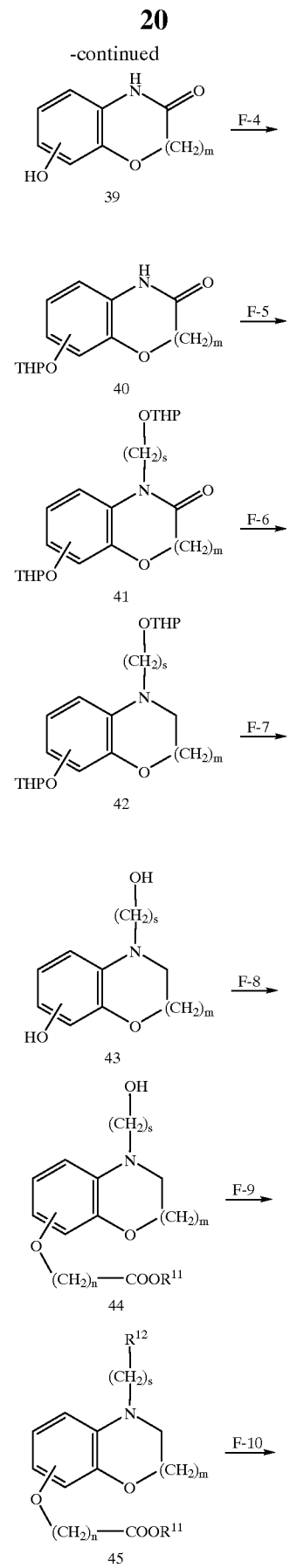

-continued

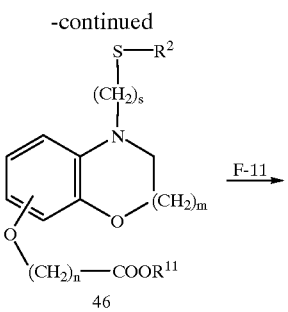

46

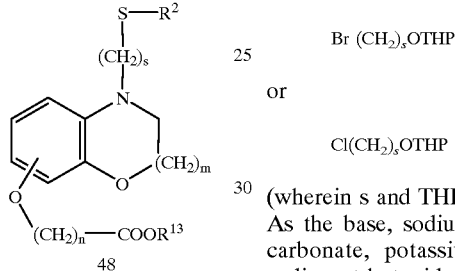

(wherein $R^2$, m, n, $R^{11}$, $R^{12}$, $R^{13}$ and $R^{16}$ are defined as the same as the above, s represents an integer of 1 to 4, and THP represents a tetrahydropyranyl group).

Step F-1 is the step of acylating methoxyaniline. This step is carried out by reacting compound 36 with the following acid chloride in the presence of an appropriate base:

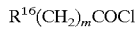

(wherein $R^{16}$ and m are defined as the same as the above). As the base, pyridine, triethylamine, or the like is used. As a solvent, methylene chloride, THF, DME, or the like is used. The reaction temperature is selected from −80 to 150° C., and is preferably −20 to 50° C. The reaction time is 1 minute to 80 hours, and is usually 5 minutes to 30 hours. This step can also be carried out by reacting compound 36 with the following acid anhydride in the presence of an appropriate base:

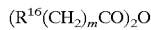

(wherein $R^{16}$ and m are defined as the same as the above). As a solvent, methylene chloride, THF, DME, or the like is used. The reaction temperature is selected from −50 to 150° C., and is preferably 0 to 50° C. The reaction time is 1 minute to 120 hours, and is usually 5 minutes to 50 hours.

Step F-2 is the step of demethylating compound 37. This step is carried out by reacting compound 37 with boron tribromide or boron tribromide-dimethylsulfide complex. As a solvent, methylene chloride, chloroform, carbon tetrachloride, or the like is used. The reaction temperature is selected from −100 to 100° C., and is preferably −80° C. to the reflux temperature of the solvent. The reaction time is 1 minute to 120 hours, and is usually 5 minutes to 50 hours.

Step F-3 is the step of cyclizing compound 38. This step is carried out by reacting compound 38 with an appropriate base. As the base, potassium carbonate, potassium t-butoxide, or the like is used. As a solvent, THF, DME, DMF, or the like is used. The reaction temperature is selected from −50 to 150° C., and is preferably 0 to 50° C. The reaction time is 1 minute to 120 hours, and is usually 5 minutes to 50 hours.

Step F-4 is the step of protecting a phenol compound by tetrahydropyranyl ether. This step is carried out by reacting compound 39 with dihydropyrane in the presence of an appropriate acid catalyst. As an acid catalyst, p-toluenesulfonic acid, pyridinium p-toluenesulfonate, or the like is used. As a solvent, THF, DME, DMF, methylene chloride, or the like is used. The reaction temperature is selected from −50 to 150° C., and is preferably 0 to 50° C. The reaction time is 1 minute to 120 hours, and is usually 5 minutes to 50 hours.

Step F-5 is the step of alkylating amide. This step is carried out by reacting compound 40 with a base, and then reacting the product with the following compound:

Br(CH$_2$)$_s$OTHP or

Cl(CH$_2$)$_s$OTHP (wherein s and THP are defined as the same as the above). As the base, sodium hydride, potassium hydride, sodium carbonate, potassium carbonate, potassium t-butoxide, sodium t-butoxide, or the like is used. As a solvent, methanol, ethanol, DMF, DMSO, THF, DME, or the like is used. The reaction temperature is selected from −50 to 150° C., and is preferably 0 to 50° C. The reaction time is 1 minute to 120 hours, and is usually 5 minutes to 50 hours.

Step F-6 is the step of reducing amide of compound 41. This step is carried out by the same method as step D-3.

Step F-7 is the step of removing a tetrahydropyranyl group of compound 42. This step is carried out by treating compound 42 with an appropriate acid catalyst. As the acid catalyst, p-toluenesulfonic acid, pyridinium p-toluenesulfonate, hydrochloric acid, or the like is used. As a solvent, methanol, ethanol, or the like is used. The reaction temperature is selected from −50 to 150° C., and is preferably 0 to 50° C. The reaction time is 1 minute to 120 hours, and is usually 5 minutes to 50 hours.

Step F-8 is the step of introducing an ester unit into compound 43. This step is carried out by the same method as step A-1.

Step F-9 is the step of converting a hydroxyl group of compound 44 to a leaving group. This step is carried out by the same method as step A-2.

Step F-10 is the step of thioetherifying compound 45. This step is carried out by the same method as step A-3.

Step F-11 is the step of ester hydrolysis of compound This step is carried out by the same method as step A-4.

Step F-12 is the step of forming a salt of compound 47. This step is carried out by the same method as step A-5.

Of the compounds of the present invention, compounds in a which $A^1$ is —O—, $A^2$ is —(N—)—CO—, $A^3$ is straight chain alkylene having 1 to 4 carbon atoms, $A^4$ is —S—, $R^3$ is hydrogen, and X is —O— can be produced by production method G.

Production method G

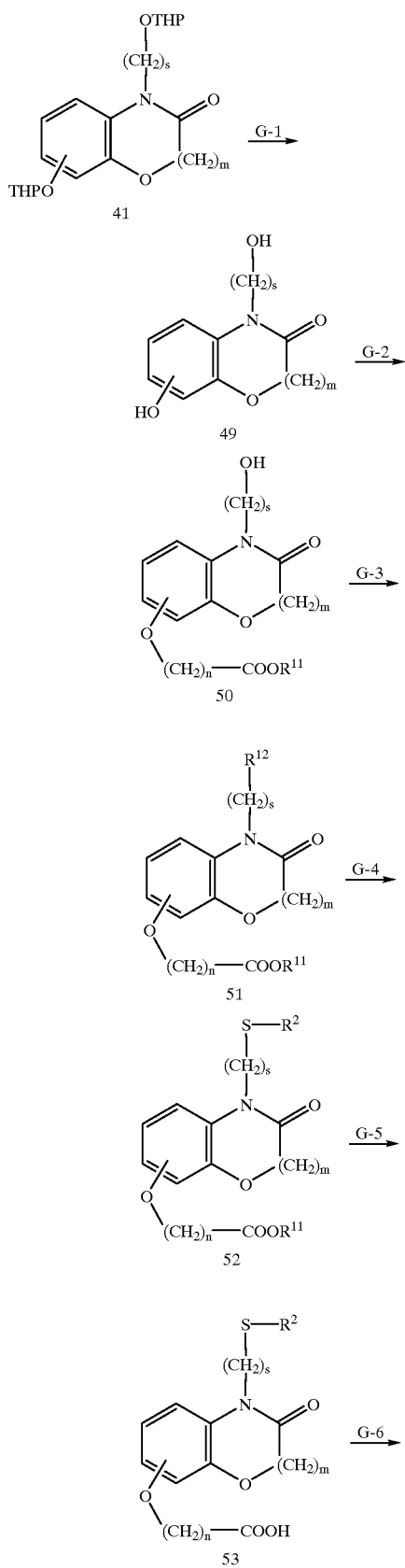

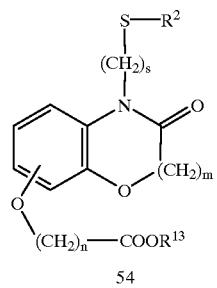

(wherein $R^2$, m, n, S, $R^{11}$, $R^{12}$, and $R^{13}$ are defined as the same as the above, and THP represents a tetrahydropyranyl group).

Step G-1 is the step of removing a tetrahydropyranyl group of compound 41. This step is carried out by the same method as step F-7.

Step G-2 is the step of introducing an ester unit into compound 49. This step is carried out by the same method as step A-1.

Step G-3 is the step of converting a hydroxyl group of compound 50 to a leaving group. This step is carried out by the same method as step A-2.

Step G-4 is the step of thioetherifying compound 51. This step is carried out by the same method as step A-3.

Step G-5 is the step of ester hydrolysis of compound 52. This step is carried out by the same method as step A-4.

Step G-6 is the step of forming a salt of compound 53. This step is carried out by the same method as step A-5.

Of the compounds of the present invention, compounds in which $A^1$ is —O—, $A^2$ is —(N—)—CO—, $A^3$ is straight chain alkylene having 1 to 4 carbon atoms, $R^3$ is hydrogen, and X is —O— can be produced by production method H.

Production method H

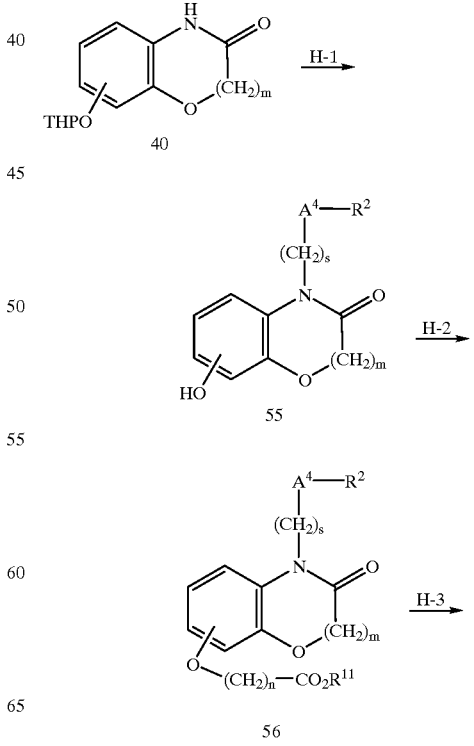

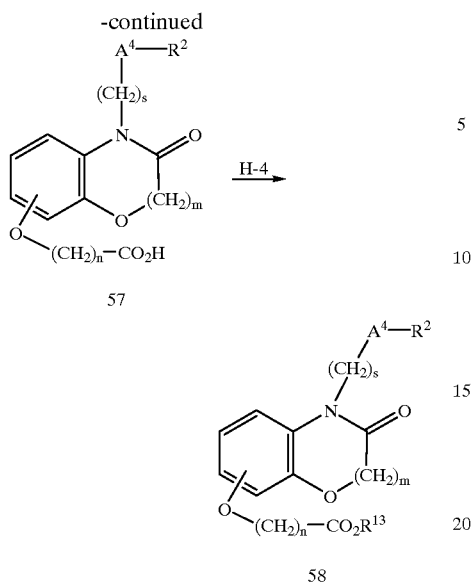

57

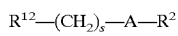

58

(wherein $R^2$, m, n, s, $R^{11}$, and $R^{13}$ are defined as the same as the above, and THP represents a tetrahydropyranyl group).

Step H-1 comprises the step of alkylating amide of compound 40, and the step of removing a tetrahydropyranyl group. The step of alkylating amide is carried out by reacting compound 40 with a base, and then reacting the product with the following compound:

$$R^{12}-(CH_2)_s-A-R^2$$

(wherein $R^2$, $R^{12}$, $A^4$, s are defined as the same as the above) As the base, sodium hydride, potassium hydride, sodium carbonate, potassium carbonate, potassium t-butoxide, sodium t-butoxide, or the like is used. As a solvent, methanol, ethanol, DMF, DMSO, THF, DME, or the like is used. The reaction temperature is selected from –50 to 150° C., and is preferably 0 to 50° C. The reaction time is 1 minute to 120 hours, and is usually 5 minutes to 50 hours. The step of removing a tetrahydropyranyl group is carried out by the same method as step F-7.

Step H-2 is the step of introducing an ester unit into compound 55. This step is carried out by the same method as step A-1.

Step H-3 is the step of ester hydrolysis of compound 56. This step is carried out by the same method as step A-4.

Step H-4 is the step of forming a salt of compound 57. This step is carried out by the same method as step A-5.

Of the compounds of the present invention, compounds in which $A^1$ is —O—, $A^2$ is —(N—)—CO—, $A^3$ is straight chain alkylene having 1 to 4 carbon atoms, $A^4$ is —S—, $R^3$ is hydrogen, X is —CH$_2$—, and n is 1 can be produced by production method I.

Production method I

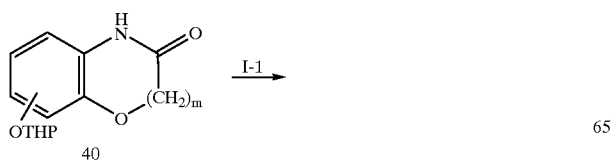

40

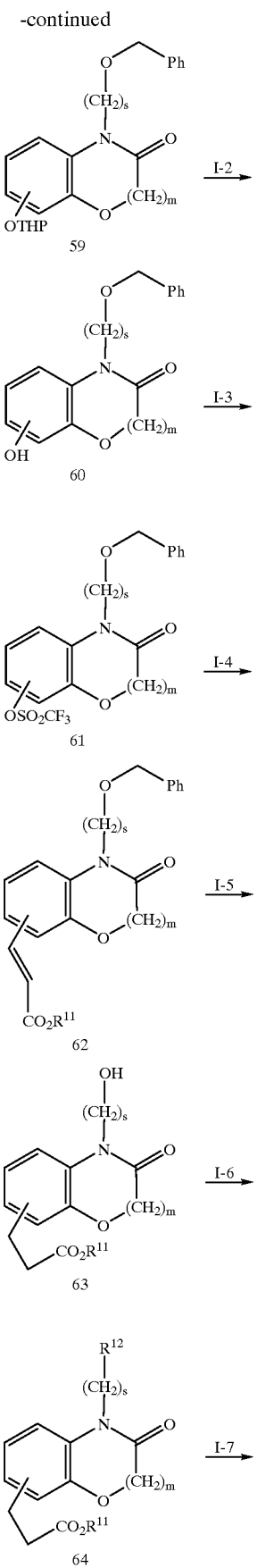

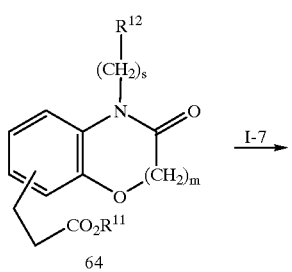

-continued

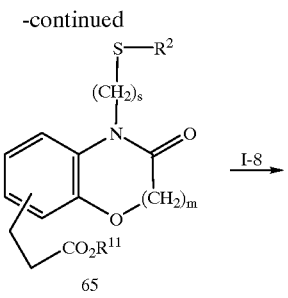

65

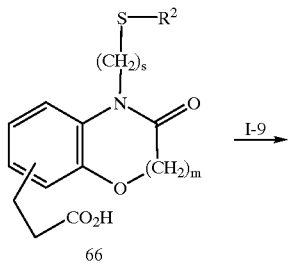

66

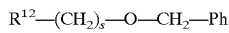

67

(wherein $R^2$, m, s, $R^{11}$, $R^{12}$, and $R^{13}$ are defined as the same as the above, and THP represents a tetrahydropyranyl group).

Step I-1 is the step of alkylating amide of compound 40. This step of alkylating amide is carried out by reacting compound 40 with a base, and then reacting the product with the following compound:

$$R^{12}-(CH_2)_s-O-CH_2-Ph$$

(wherein $R^{12}$ and s are defined as the same as the above). As the base, sodium hydride, potassium hydride, sodium carbonate, potassium carbonate, potassium t-butoxide, sodium t-butoxide, or the like is used. As a solvent, methanol, ethanol, DMF, DMSO, THF, DME, or the like is used. The reaction temperature is selected from −50 to 150° C., and is preferably 0 to 50° C. The reaction time is 1 minute to 120 hours, and is usually 5 minutes to 50 hours.

Step I-2 is the step of removing a tetrahydropyranyl group of compound 59. This step is carried out by the same method as step F-7.

Step I-3 is the step of trifluoromethanesulfonylating a hydroxyl group of compound 60. This step is carried out by reacting compound 60 with a trifluoromethanesulfonylating agent in the presence of a base. As the base, 2,6-lutidine, pyridine, triethylamine, diisopropylamine, diisopropylethylamine, or the like is preferably used. As the trifluoromethanesulfonylating agent, trifluoromethane-sulfonic anhydride, trifluoromethanesulfonyl chloride, or the like is preferably used. As a solvent, THF, DME, dioxane, benzene, toluene, methylene chloride, DMF, or the like is used, and a base such as 2,6-lutidine, or the like may be used as the solvent. The reaction temperature is selected from −80 to 150° C., and is preferably −20 to 50° C. The reaction time is 1 minute to 80 hours, and is usually 5 minutes to 30 hours.

Step I-4 is the step of introducing an ester unit into an aromatic ring of compound 61. This step is carried out by Heck reaction of compound 61 and an acrylate. As a catalyst, palladium acetate, tetrakistriphenylphosphine palladium complex, or the like is preferably used. As a reaction additive, triphenylphosphine, tris(2-methylphenyl) phosphine, lithium chloride, or the like is preferably used. As the base, 2,6-lutidine, pyridine, triethylamine, diisopropylamine, diisopropylethylamine, or the like is preferably used. As a solvent, THF, DME, dioxane, benzene, toluene, methylene chloride, DMF, or the like is used, and a base such as pyridine or the like may be used as the solvent. The reaction temperature is selected from −80 to 150° C., and is preferably 0 to 120° C. The reaction time is 1 minute to 80 hours, and is usually 5 minutes to 30 hours.

Step I-5 is the step of reducing compound 62, comprising simultaneously reducing a double bond and reductively removing a benzyl group. This step is carried out by reducing compound 62 by a catalytic hydrogenation method. As a hydrogen source, hydrogen gas, formic acid, ammonium formate, sodium formate, or the like is preferably used. As a catalyst, palladium carbon, platinum, platinum oxide, platinum carbon, palladium acetate, a tetrakistriphenylphosphine palladium complex, or the like is preferably used. As a solvent, methanol, ethanol, ethyl acetate, acetic acid, trifluoroacetic acid, water, tetrahydrofuran, dimethoxyethane, or the like is preferably used. As a reaction additive, hydrochloric acid, sulfuric acid, activated carbon, iron powder, zinc powder, or the like is preferably further used. The reaction temperature is selected from −50 to 150° C., and is preferably 0 to 120° C. The reaction time is 1 minute to 120 hours, and is usually 1 minute to 30 hours.

Step I-6 is the step of converting a hydroxyl group of compound 63 to a leaving group. This step is carried out by the same method as step A-2.

Step I-7 is the step of thioetherifying compound 64. This step is carried out by the same method as step A-3.

Step I-6 is the step of ester hydrolysis of compound 65. This step is carried out by the same method as step A-4.

Step I-7 is the step of forming a salt of compound 66. This step is carried out by the same method as step A-5.

Of the compounds of the present invention, compounds in which $A^1$ is —O—, $A^2$ is —(N—)—$CH_2$—, $A^3$ is straight chain alkylene having 1 to 4 carbon atoms, $A^4$ is —NH—, $R^3$ is hydrogen, X is —O—, and $R^2$ is —$CH_2$—$R^{17}$ can be produced by production method J.

Production method J

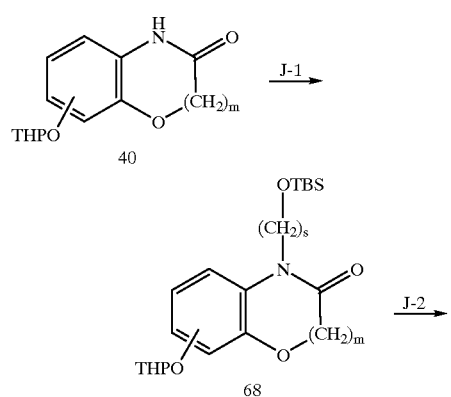

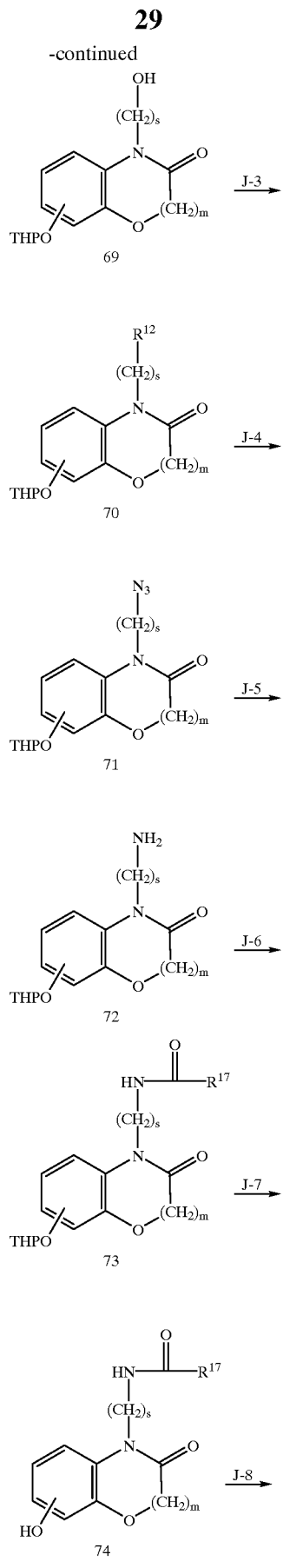

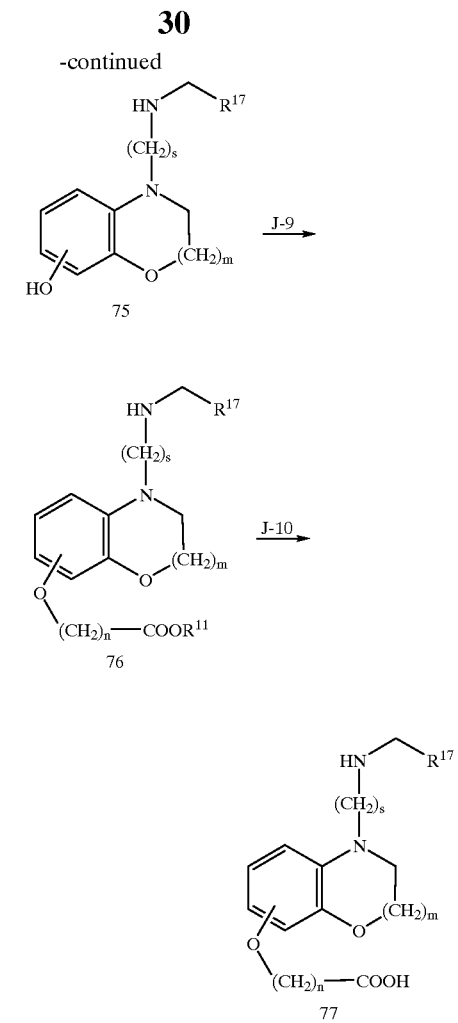

(wherein m, s, $R^{11}$, and $R^{12}$ are defined as the same as the above, THP represents a tetrahydropyranyl group, and TBS represents a t-butyldimethylsilyl. $R^{17}$ represents the following:

(1) -Ar (wherein Ar is phenyl, naphthyl, furyl, or thienyl (wherein phenyl, naphthyl, furyl, or thienyl may be substituted by a group selected from alkyl having 1 to 5 carbon atoms, phenyl, hydroxyl, alkoxy having 1 to 5 carbon atoms, phenoxy, halogen, trifluoromethyl, cyano, nitro, amino, and alkylamino having 1 to 5 carbon atoms); or (2) alkyl having 1 to 4 carbon atoms, alkenyl having 2 to 4 carbon atoms, or alkynyl having 2 to 4 carbon atoms (wherein alkyl, alkenyl, or alkynyl is substituted by one or two Ar (wherein Ar is defined as the same as the above), and may be further substituted by a group selected from —OH, —CF$_3$, and cycloalkyl having 3 to 8 carbon atoms)).

Step J-1 is the step of alkylating amide. This step is carried out by reacting compound 40 with a base, and then reacting the product with the following compound:

Br(CH$_2$)$_s$OTBS or

Cl(CH$_2$)$_s$OTBS (wherein s and TBS are defined as the same as the above). As the base, sodium hydride, potassium hydride, sodium carbonate, potassium carbonate, potassium t-butoxide, sodium t-butoxide, or the like is used. As a solvent, methanol, ethanol, DMF, DMSO, THF, DME, or the like is used. The reaction temperature is selected from −50 to 150° C., and is preferably 0 to 50° C. The reaction time is 1 minute to 120 hours, and is usually 5 minutes to 50 hours.

Step J-2 is the step of removing a TBS group of compound 68. This step is carried out by treating compound 68 with fluorine ion. As a fluorine ion source, tetrabutylammonium fluoride, potassium fluoride, hydrofluoric acid, or the like is used. As a solvent, tetrahydrofuran, dimethoxyethane, or the like is used. The reaction temperature is selected from −50 to 150° C., and is preferably 0 to 50° C. The reaction time is 1 minute to 120 hours, and is usually 5 minutes to 50 hours.

Step J-3 is the step of converting a hydroxyl group of compound 69 to a leaving group. This step is carried out by the same method as step A-2.

Step J-4 is the step of converting a hydroxyl group of compound 70 to azide. This step is carried out by treating compound 70 with sodium azide. As a solvent, DMF, tetrahydrofuran, dimethoxyethane, or the like is used. The reaction temperature is selected from −50 to 150° C., and is preferably 0 to 50° C. The reaction time is 1 minute to 120 hours, and is usually 5 minutes to 50 hours.

Step J-5 is the step of reducing compound 71. This step is carried out by the same method as step I-5.

Step J-6 is the step of acylating compound 72. This step is carried out by reacting compound 72 with a corresponding carboxylic acid in the presence of a condensing agent. As the condensing agent, dicyclohexylcarbodiimide, 1-ethyl-3-(3-dimethylaminopropyl)carbodiimide, 1-cyclohexyl-3-(2-morpholynoethyl)carbodiimide metho-p-toluenesufonate, or the like is preferably used. As a solvent, acetonitrile, DMF, tetrahydrofuran, dimethoxyethane, or the like is used. The reaction temperature is selected from −50 to 150° C., and is preferably 0 to 50° C. The reaction time is 1 minute to 120 hours, and is usually 5 minutes to 50 hours. Similarly to step E-1, this step can also be carried out by reacting compound 72 with an acid chloride or acid anhydride in the presence of an appropriate base.

Step J-7 is the step of removing a tetrahydropyranyl group of compound 73. This step is carried out by the same method as step F-7.

Step J-8 is the step of reducing amide of compound 74. This step is carried out by the same method as step C-5.

Step J-9 is the step of introducing an ester unit into compound 75. This step is carried out by the same method as step A-1.

Step J-10 is the step of ester hydrolysis of compound 76. This step is carried out by the same method as step A-4.

Of the compounds of the present invention, compounds in which $A^1$ is —$CH_2$—, $A^2$ is —(N—)—$CH_2$—, $A^3$ is straight chain alkylene having 1 to 4 carbon atoms, $R^3$ is hydrogen, and X is —O— can be produced by production method K.

Production method K

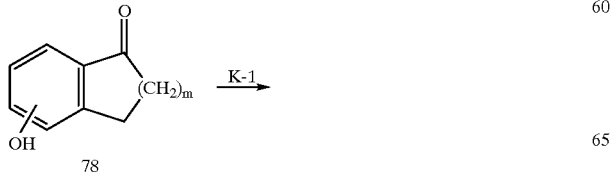
78

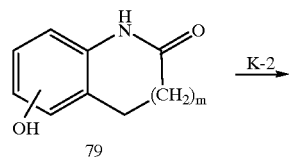
79 K-2

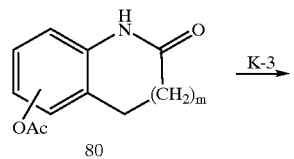
80 K-3

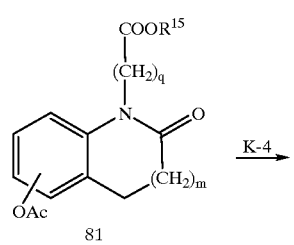
81 K-4

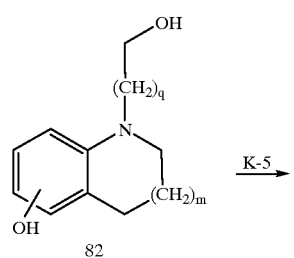
82 K-5

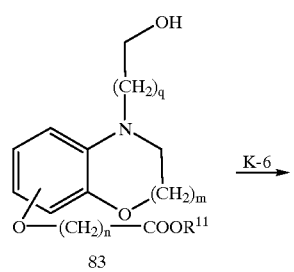
83 K-6

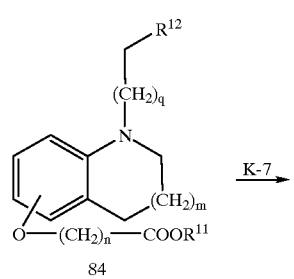
84 K-7

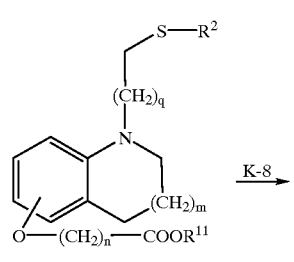
85 K-8

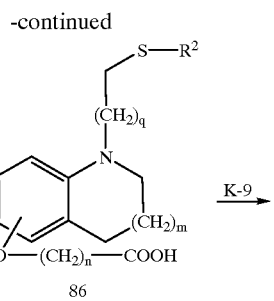

86

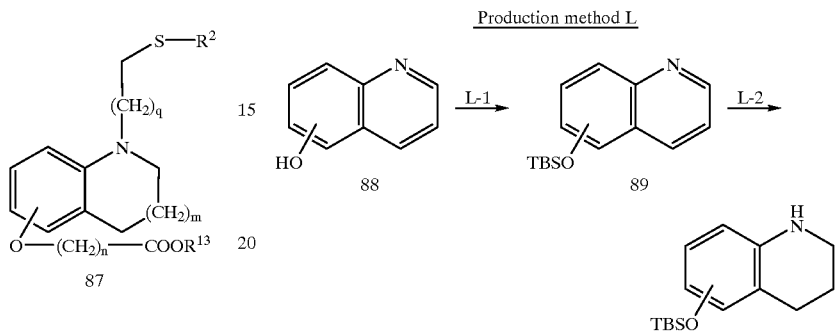

87

(wherein $R^2$, m, n, $R^{11}$, $R^{12}$, $R^{13}$, $R^{15}$, and q are defined as the same as the above).

Step K-1 is the step of producing amide by rearrangement reaction of tetralone. This step is carried. out by reacting compound 78 with sodium azide in trifluoroacetic acid. The reaction temperature is −20° C. to the reflux temperature of a solvent. The reaction time is 1 minute to 120 hours, and is usually 5 minutes to 50 hours.

Step K-2 is the step of protecting a phenolic hydroxyl group by an acetyl group. This step is carried out by reacting with acetic anhydride or acetyl chloride in the presence of an appropriate base. As the base, pyridine, triethylamine, or the like is used. As a solvent, THF, DME, methylene chloride, or the like is used, and pyridine may be used as the solvent. The reaction temperature is selected from −50 to 150° C., and is preferably 0 to 50° C. The reaction time is 1 minute to 120 hours, and is usually 5 minutes to 50 hours.

Step K-3 is the step of introducing an ester unit into amide. This step is carried out by reacting compound 80 with the following compound in the presence of an appropriate base:

$Br(CH_2)_qCOOR^{15}$ (wherein $R^{15}$ and q are defined as the same as the above). As the base, potassium carbonate, potassium t-butoxide, potassium hydroxide, sodium hydroxide, sodium hydride, or the like is used. As a solvent, methanol, ethanol, DMF, DMSO, THF, DME, or the like is used. The reaction temperature is selected from −50 to 150° C., and is preferably 0 to 50° C. The reaction time is 1 minute to 120 hours, and is usually 5 minutes to 50 hours.

Step K-4 is the step of reducing ester and amidoe and removing an acetyl group at the same time. This step is carried out by reacting compound 81 with lithium aluminum hydride. As a solvent, THF, DME, ether, or the like is used. The reaction temperature is −40° C. to the reflux temperature of the solvent. The reaction time is 1 minute to 120 hours, and is usually 5 minutes to 50 hours.

Step K-5 is the step of introducing an ester unit into compound 82. This step is carried out by the same method as step A-1.

Step K-6 is the step of converting a hydroxyl group of compound 83 to a leaving group. This step is carried out by the same method as step A-2.

Step K-7 is the step of thioetherifying compound 84. This step is carried out by the same method as step A-3.

Step K-8 is the step of ester hydrolysis of compound 85. This step is carried out by the same method as step A-4.

Step K-9 is the step of forming a salt of compound 86. This step is carried out by the same method as step A-5.

Of the starting raw materials of the production method E, compounds in which $A^1$ is —$CH_2$—, m is 1, and $R^3$ is hydrogen can be produced by production method L.

Production method L

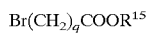

(wherein TBS represents a t-butyldimethylsilyl group).

Step L-1 is the step of protecting a hydroxyl group of quinoline by a t-butyldimethylsilyl group. This step is carried out by reacting compound 88 with t-butyldimethylsilylchloride in the presence of an appropriate base. As the base, imidazole is preferably used. As a solvent, DMF, THF, or the like is used. The reaction temperature is selected from −50 to 150° C., and is preferably 0 to 50° C. The reaction time is 1 minute to 80 hours, and is usually 5 minutes to 30 hours.

Step L-2 is the step of reducing quinoline to tetrahydroquinoline, and performed under conventional conditions for hydrogenation. This step is carried out by using a catalyst such as palladium-carbon, Raney nickel, or the like under a hydrogen atmosphere at a pressure of 1 to 10 atm. As a solvent, methanol, ethanol, THF, ethyl acetate, benzene, or the like is used. The reaction temperature is selected from −50 to 150° C., and is preferably 0 to 50° C. The reaction time is 1 minute to 120 hours, and is usually 5 minutes to 50 hours.

Of the compounds of the present invention, compounds in which $A^1$ is —O—, $A^2$ is —(CH—)—, $A^3$ is —$CH_2CH_2$—, $A^4$ is —S—, $R^3$ is hydrogen, X is —O—, and m is 1 can be produced by production method M.

Step M-1 is the step of reducing benzofuran to dihydrobenzofuran. This step is carried out by using a catalyst such as palladium-carbon, Raney nickel, or the like under a hydrogen atmosphere at a pressure of 1 to 10 atm., and reaction is accelerated by adding an acid such as acetic acid, hydrochloric acid, or the like. As a solvent, methanol, ethanol, THF, ethyl acetate, benzene, or the like is used. The reaction temperature is selected from −50 to 150° C., and is preferably 0 to 50° C. The reaction time is 1 minute to 120 hours, and is usually 5 minutes to 50 hours.

Step M-2 is the step of thioetherifying compound 92. This step is carried out by the same method as step A-3.

Step M-3 is the step of ester hydrolysis of compound 93. This step is carried out by the same method as step A-4.

Step M-4 is the step of forming a salt of compound 94. This step is carried out by the same method as step A-5.

Production method M

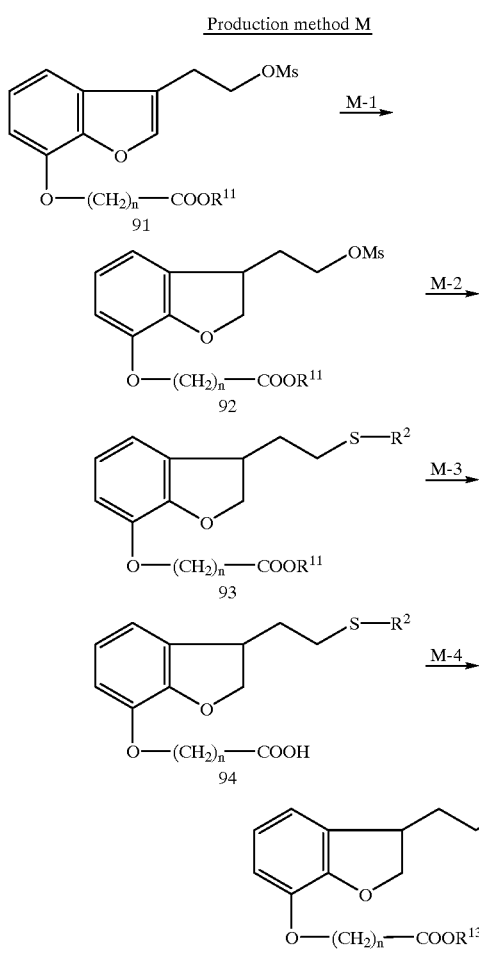

(wherein $R^2$, n, $R^{11}$ and $R^{13}$ are defined as the same as the above).

Of the compounds of the present invention, optically active compounds in which $A^1$ is —O—, $A^2$ is —(CH—)—, $A^3$ is —CH$_2$CH$_2$—, $A^4$ is —S—, $R^3$ is hydrogen, X is —O—, and m is 1 can be produced by production method N.

Production method N

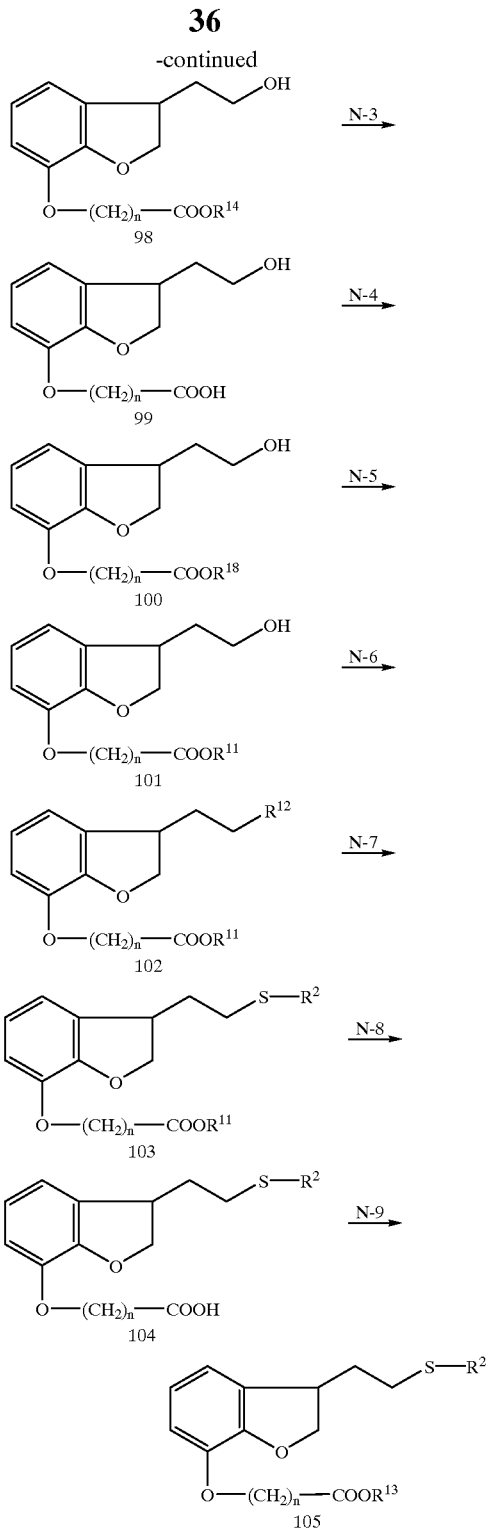

(wherein $R^2$, n, $R^{11}$, $R^{12}$, $R^{13}$ and $R^{14}$ are defined as the same as the above, and $R^{18}$ represents an optically active amine cation).

Step N-1 is the step of introducing an ester unit into a phenolic hydroxyl group of compound 96. This step is carried out by the same method as step A-1.

Step N-2 is the step of reducing benzofuran of compound 97 to dihydrobenzofuran. This step is carried out by the same method as step M-1.

Step N-3 is the step of ester hydrolysis of compound 98. This step is carried out by the same method as step A-4.

Step N-4 is the step of optical resolution of compound 99, comprising a salt formation step and a resolution step. The salt formation step is carried out by reacting compound 99 with an optically active amine. As the optically active amine, 1-(1-naphthyl)ethylamine, 2-(benzylamino)cyclohexane methanol, cinchonine, or the like is preferably used. As a solvent, water, methanol, ethanol, tetrahydrofuran, ethyl acetate, or the like is used. The reaction temperature is selected from −50 to 150° C., and is preferably 0 to 80° C. The reaction time is 1 minute to 120 hours, and is usually 1 minute to 30 hours. The resolution step is carried out by dissolving an optically active amine salt of compound 99 under heating, and then standing it to cool. Crystallization may be accelerated by adding a seed crystal. As a solvent, water, methanol, ethanol, tetrahydrofuran, ethyl acetate, or the like is used.

N-5 is the step of esterifying compound 100. This step is carried out by refluxing compound 100 with alcohol under acidic conditions. As an acid, sulfuric acid, hydrochloric acid, hydrobromic acid, hydroiodic acid, methanesulfonic acid, trifluoromethanesulfonic acid, or the like is used. As a solvent, benzene, toluene, or the like is used, and alcohol may be used as the solvent. Furthermore, a dehydrating agent may be added, or a dehydrating device such as Dean-stark or the like may be used. The reaction temperature is selected from 0 to 150° C., and reaction is preferably effected under reflux conditions of the solvent. The reaction time is 1 minute to 120 hours, and is usually 5 minutes to 50 hours Step N-6 is the step of converting a hydroxyl group of compound 101 to a leaving group. This step is carried out by the same method as step A-2.

Step N-7 is the step of thioetherifying compound 102. This step is carried out by the same method as step A-3.

Step N-8 is the step of ester hydrolysis of compound 103. This step is carried out by the same method as step A-4.

Step N-9 is the step of forming a salt of compound 104. This step is carried out by the same method as step A-5.

With the compounds of the present invention having asymmetric carbons, the formula represents d, l and dl isomers. Each of the steps can be applied to the d, l and dl isomers in the same manner.

In producing dl isomers of the compounds of the present invention, compounds represented by formula (I), which are obtained in a racemic modification, can easily be separated into d and l isomers by an optically active column chromatography technique.

The compounds of the present invention have the strong TXA$_2$ receptor antagonistic action and PGI$_2$ receptor agonistic action, and thus have pharmacological actions such as the platelet aggregation inhibiting action, vascular contraction inhibiting action, bronchial contraction inhibiting action, etc. Therefore, these compounds are effective to treat or prevent diseases such as hypertension, thrombosis, ischemic heart diseases (myocardial infarction, angina pectoris, thrombogenesis after PTCA, etc.), cerebral circulatory disorders (cerebral infarction, transient cerebral ischemic attack, etc.), peripheral circulatory disorders (Buerger's disease, Raynaud's disease, Behcet's disease, thrombotic thrombocytopetic purpura, hepatic disorders, renal disorders, etc.), arteriosclerosis, platelet functional disorder concurrent with diabetes, hyperlipidemia, nephritis, asthma, allergic diseases, etc.

For this purpose, the compounds of the present invention can be generally administered by intravenous injection, intraarterial injection, intramuscular injection, percutaneous administration, subcutaneous administration, or oral administration. In general oral or rectal administration, the compound is administered 1 to 4 times a day at a dose of 1 µg/kg/day to 100 mg/kg/day. In intravenous infusion or intraarterial injection, the compound is administered at a dose of 1 ng/kg/min to 1 mg/kg/min to obtain good results. In general intravenous injection, intraarterial injection, intramuscular injection, or subcutaneous administration, the compound is administered 1 to 4 times a day at a dose of 0.1 µg/kg/day to 100 mg/kg/day. In these administrations, a dose is selected from the above-described ranges in consideration of the age, sexuality, and conditions of a patient, and the times of administration of the compound, etc.

The compounds of the present invention can be orally administered in a solid form containing starch, lactose, sucrose, glucose, crystalline cellulose, an excipient such as a type of clay, a colorant, a lubricant, a binder, a disintegrant, and a coating agent. The compounds of the present invention may be parenterally administered in the form of a sterilized solution, and may also contain other solutes such as a tonicity agent such as sodium chloride, glucose, or the like, a PH regulator, and solution adjuvant such as cyclodextrin or the like. The compounds of the present invention have stability in chemical structure, and thus cause no difficulties in formulation, thereby permitting a variety of administration methods such as oral formulations (tablets, powder, and granules), various injections, suppositories, ointments, lotions, etc.

EXAMPLES

The present invention will be described in further detail below with reference to examples.

Reference Example 1

4-bromo-2-nitro-6-methoxyphenol

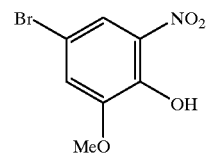

Trifluoroacetic anhydride (3.50 ml) was cooled to −78° C. 61% nitric acid (1.85 ml) was slowly added dropwise at −78° C., and the resultant mixture was stirred at 0° C. for 2.5 hours. The above nitrating agent was added to a solution of 4-bromoguaiacol (5.00 g) in ethyl acetate (50 ml) and the mixture was stirred at 0° C. for 1.5 hours. Saturated brine was added to the reaction solution, and an organic layer was then separated. The organic layer was washed with water and saturated brine, dried over magnesium sulfate, concentrated, and then allowed to cool to form crystals. After filtration, the crystal was washed with a small amount of n-hexane, and then dried under reduced pressure to obtain the object compound (4.02 g, yield 66%).

Pale yellow needle crystals: mp. 113–114° C. (recrystallized from ethyl acetate)

$^1$H-NMR (300 MHz, CDCl$_3$) δ3.96 (3H, s), 7.21 (1H, d, J=2.2 Hz), 7.86 (1H, d, J=2.2 Hz).

IR (KBr method) 3192, 3093, 1537, 1316, 1259, 1153, 1049, 915, 702, 676 cm$^{-1}$ Mass (EI, m/e) 247, 249 (M$^+$) (peak height 1:1)

Reference Example 2

Methyl 4-bromo-2-nitro-6-methoxyphenoxyacetate

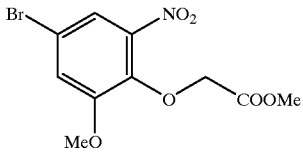

4-bromo-2-nitro-6-methoxyphenol (52.2 g) was dissolved in DMF (450 ml), and methyl bromoacetate (30 ml) and potassium carbonate (41.5 g) were added to the solution, and the mixture was stirred at room temperature for 14 hours. The reaction solution was subjected to suction filtration to remove inorganic salts, and the residue was washed with a small amount of ethyl acetate. The filtrate was concentrated, and ethanol was added to the residue to crystallize. After filtration, the crystal was washed with small amounts of water and ethanol, and then dried under reduced pressure to obtain the object compound (50.54 g, it yield 75%).

Colorless needle crystals: mp. 130–130.5° C. (recrystallized from ethanol)

$^1$H-NMR. (300 MHz, CDCl$_3$) δ3.79 (3H, s), 3.91 (3H, s), 4.76 (2H, s), 7.22 (1H, d, J=2.2 Hz), 7.52 (1H, d, J=2.2 Hz).

IR (KBr method) 3085, 3033, 2992, 2955, 1760, 1595, 1538, 1481, 1444, 1361, 1260, 1205, 1176, 1053, 856, 696 cm$^{-1}$ Mass (EI, m/e) 319, 321 (M$^+$) (peak height=1:1)

Reference Example 3

8-methoxy-3-oxo-3,4-dihydro-2H-1,4-benzoxazine

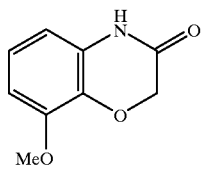

Methyl 4-bromo-2-nitro-6-methoxyphenoxyacetate (897 mg), Zn (50 mg), activated carbon (130 mg), and 10% Pd/C (containing 50% water) (50 mg) were suspended in acetic acid (10 ml), and the resultant suspension was stirred at 70° C. for 7.5 hours in a hydrogen atmosphere. The temperature was returned to room temperature, and an aqueous solution obtained by dissolving sodium acetate (250 mg) in water (1.0 ml) was then added to the reaction solution. The mixture was filtered with a membrane filter, and the residue was washed with a small amount of ethyl acetate. The filtrate was evaporated, and water was added to the residue to crystallize. After filtration, the crystal was dried under reduced pressure to obtain the object compound (470 mg, yield 94%).

Colorless needle crystals: mp. 186–187° C. (recrystallized from ethyl acetate/n-hexane)

$^1$H-NMR (300 MHz, CDCl$_3$) δ3.90 (3H, s), 4.68 (2H, s), 6.45 (1H, dd, J=1.5, 8 Hz), 6.65 (1H, dd, J=1.5, 8 Hz), 6.92 (1H, t, J=8 Hz), 9.19 (1H, bs).

IR (KBr method) 3052, 3006, 2938, 1696, 1615, 1518, 1489, 1437, 1402, 1282, 1249, 1216, 1172, 1120, 1031, 774, 723 cm$^{-1}$ Mass (EI, m/e) 179 (M$^+$)

Reference Example 4

Methyl 8-methoxy-3-oxo-3,4-dihydro-2H-1,4-benzooxazine-4-ylacetate

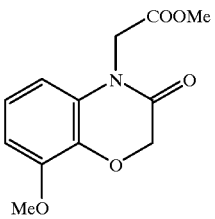

8-methoxy-3-oxo-3,4-dihydro-2H-1,4-benzoxazine (2.00 g) and potassium carbonate (1.85 g) were suspended in DMF (4.0 ml), and methyl bromoacetate (1.20 ml) was added to the resultant suspension, and the mixture was stirred at room temperature for 18.5 hours. The reaction solution was subjected to suction filtration to remove inorganic salts, and the residue was washed with a small amount of ethyl acetate. Water (10 ml) and saturated brine (10 ml) were added to the filtrate, and the resulting mixture was then extracted with ethyl acetate. The resultant organic layer was washed with water and saturated brine, dried over magnesium sulfate, and then evaporated. The residue was recrystallized from ethyl acetate/n-hexane to obtain the object compound (2.58.g, yield 92%).

Colorless leaf-like crystals: mp. 118–119° C. (recrystallized from ethyl acetate/n-hexane)

$^1$H-NMR (300 MHz, CDCl$_3$) δ3.78 (3H, s), 3.91 (3H, s), 4.67 (2H, s), 4.74 (2H, s), 6.41 (1H, dd, J=1, 8 Hz), 6.71 (1H, dd, J=1, 8 Hz), 6.97 (1H, t, J=8 Hz).

IR (KBr method) 2966, 1746, 1680, 1487, 1429, 1404, 1209, 1166, 1052 cm$^{-1}$

Mass (El, m/e) 251 (M$^+$)

Reference Example 5

4-(2-hydroxyethyl)-8-methoxy-3,4-dihydro-2H-1,4-benzoxazine

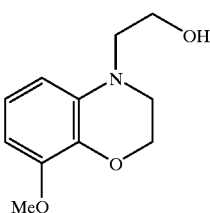

Methyl 8-methoxy-3-oxo-3,4-dihydro-2H-1,4-benzooxazine-4-ylacetate (4.52 g) and sodium borohydride (1.10 g) were suspended in THF (10 ml), and the resultant suspension was cooled to 0° C. A trifluoroboron-tetrahydrofuran complex (4.0 ml, 2.0 eq) was slowly added dropwise to the suspension. After heat generation stopped, the temperature was returned to room temperature, and the reaction solution was further stirred at 70° C. for 22 hours. The reaction solution was then cooled to 0° C., and water was added thereto to terminate reaction. Then, the reaction solution was rendered basic with sodium carbonate, and extracted with ethyl acetate. The resultant organic layer was washed with water, saturated sodium bicarbonate solution, and saturated brine, dried over magnesium sulfate, and then evaporated. The residue was recrystallized from ethyl acetate/n-hexane to obtain the object compound (3.37 g, yield 89%).

Colorless prismatic crystals: mp. 59–60° C. (recrystallized from ethyl acetate/n-hexane)

$^1$H-NMR (300 MHz, CDCl$_3$) δ1.79 (1H, t, J=5 Hz), 3.42 (4H, m), 3.83 (2H, q, J=5 Hz), 3.86 (3H, s), 4.31 (2H, m), 6.38 (1H, dd, J=1.5, 8 Hz), 6.45 (1H, dd, J=1.5, 8 Hz), 6.78 (1H, t, J=8 Hz).

IR (KBr method) 3259, 2931, 2871, 1610, 1500, 1460, 1347, 1273, 1248, 1204, 1138, 1064, 762, 717 cm$^{-1}$ Mass (EI, m/e) 209 (M$^+$)

Reference Example 6

4-(2-hydroxyethyl)-8-hydroxy-3,4-dihydro-2H-1,4-benzoxazine

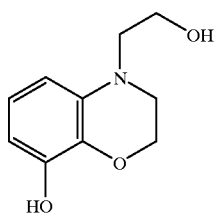

A solution of 4-(2-hydroxyethyl)-8-methoxy-3,4-dihydro-2H-1,4-benzoxazine (20.70 g) in dichloromethane (350 ml) was cooled to −78°. Boron tribromide (42.09 g) was added dropwise to the solution over 20 minutes, and the resultant mixture was stirred at room temperature for 1.5 hours. An aqueous solution of sodium hydroxide was added to the reaction solution, and the mixture was rendered basic with a saturated sodium bicarbonate solution, and then extracted with ethyl acetate. The resultant organic layer was washed with water and saturated brine, dried over magnesium sulfate, and then evaporated to obtain the object compound (15.55 g, yield 81%).

Colorless plate crystals: mp. 105.5° C. (recrystallized from ethyl acetate/n-hexane)

$^1$H-NMR (300 MHz, DMSO-d$_6$) δ3.26 (1H, t, J=5.5 Hz), 3.36 (2H, t, J=4 Hz), 3.54 (2H, q, J=5.5 Hz), 4.10 (2H, t, J=4 Hz), 4.65 (1H, t, J=5.5 Hz), 6.07 (1H, dd, J=1, 8 Hz), 6.15 (1H, dd, J=1, 8 Hz), 6.49. (1H, t, J=8 Hz), 8.49 (1H, s).

IR (KBr method) 3486, 3250, 2950, 2880, 1615, 1584, 1512, 1483, 1460, 1350, 1272, 1253, 1201, 1166, 1125, 1054, 980, 930, 901, 876, 832, 795, 766, 712 cm$^{-1}$ Mass (EI, m/e) 195 (M$^+$)

Reference Example 7

Methyl (4-(2-hydroxyethyl)-3,4-dihydro-2H-1,4-benzoxazin-8-yloxy)acetate

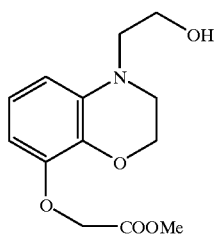

4-(2-(hydroxyethyl)-8-hydroxy-3,4-dihydro-2H-1,4-benzoxazine (4.66 g) was dissolved in anhydrous DMF (50 ml), and anhydrous potassium carbonate (8.50 g) and methyl bromoacetate (4.0 ml) were added to the resultant solution, and the mixture was stirred at room temperature for 6 hours. The solvent was distilled off, and the residue was poured into 5% citric acid, and then extracted with ethyl acetate. The resultant organic layer was washed with water and saturated brine, dried over magnesium sulfate, and then concentrated. The residue was recrystallized from ethyl acetate/n-hexane to obtain the object compound (3.83 g, yield 60%).

Colorless plate crystals: mp. 64–66° C. (recrystallized from ethyl acetate/n-hexane)

$^1$H-NMR (300 MHz, CDCl$_3$) δ1.78 (1H, t, J=5.5 Hz), 3.42 (4H, m), 3.79 (3H, s), 3.83 (2H, q, J=5.5 Hz), 4.31 (2H, m), 4.68 (2H, s), 6.26 (1H, dd, J=1, 8 Hz), 6.47 (1H, dd, J=1, 8 Hz), 6.73 (1H, t, J=8 Hz).

IR (Kbr method) 3484, 2904, 2864, 1719, 1615, 1510, 1489, 1446, 1433, 1381, 1350; 1321, 1274, 1257, 1232, 1214, 1193, 1145, 1094, 1069, 1054, 1040, 1015, 973, 650, 602 cm$^{-1}$ Mass (El, m/e) 267 (M$^+$)

Reference Example 8

2,3-dimethoxy-α-chloroacetoanilide

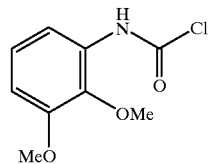

2,3-dimethoxyaniline (1.00 g) and chloroacetic anhydride (1.26 g) were dissolved in THF (5 ml), and the resultant solution was stirred at room temperature for 4 hours. The solvent was distilled off under reduced pressure, and the reaction solution was then poured into a saturated sodium bicarbonate solution, and extracted with ethyl acetate. The resultant organic layer was washed with saturated brine, dried over magnesium sulfate, and then concentrated. The residue was purified by column chromatography (silica gel; ethyl acetate/n-hexane=1:2) to obtain the object compound (1.64 g, yield 97%).

Colorless leaf-like crystals: mp. 58–59° C. (recrystallized from dichloromethane/n-hexane)

$^1$H-NMR (300 MHz, CDCl$_3$) δ3.88 (3H, s), 3.91 (3H, s), 4.20 (2H, s), 6.73 (1H, dd, J=1.5, 8.5 Hz), 7.06 (1H, t, J=8.5 Hz), 7.96 (1H, dd, J=1.5, 8.5 Hz), 9.05 (1H, bs).

IR (KBr method) 3324, 3008, 2952, 1702, 1607, 1549, 1481, 1462, 1423, 1400, 1332, 1296, 1259, 1224, 1187, 1176, 1166, 1083, 990, 967, 779, 743, 681 cm$^{-1}$ Mass (EI, m/e) 229, 231 (M$^+$) (peak height=3:1)

Reference Example 9

8-hydroxy-3-oxo-3,4-dihydro-2H-1,4-benzoxazine

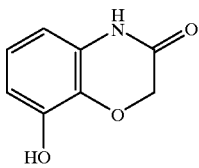

A solution of 2,3-dimethoxy-α-chloroacetoanilide (1.43 g) in dichloromethane (30 ml) was cooled to −78° C., and a solution (13.0 ml) of 1.0M boron tribromide in dichloromethane was added to the solution, and the mixture was stirred at 0° C. for 2 hours. The reaction solution was poured into water, and then extracted with ethyl acetate. The resultant organic layer was washed with water and saturated saline, dried over magnesium sulfate, and then concentrated. The residue was dissolved in anhydrous DMF (30 ml), and potassium carbonate (1.03 g) was added to the resultant solution, and the mixture was stirred for 2.5 hours. The solvent was distilled off under reduced pressure, and the residue was poured into 5% citric acid, and then extracted with ethyl acetate. The resultant organic layer was washed with water and saturated brine, dried over magnesium sulfate, and then concentrated. The residue was recrystallized from ethyl acetate to obtain the object compound (922 mg, yield 90%).

Colorless plate crystals: mp. 226° C. (recrystallized from ethyl acetate)

$^1$H-NMR (300 MHz, DMSO-d$_6$) δ4.49 (2H, s), 6.34 (1H, dd, J=1, 8 Hz), 6.45 (1H, dd, J=1, 8 Hz), 6.71 (1H, t, J=8 Hz), 9.37 (1H, bs), 10.57 (1H, bs).

IR (KBr method) 3200, 1682, 1638, 1609, 1504, 1450, 1226, 1205, 1187, 1071, 785 cm$^{-1}$ Mass (EI, m/e) 165 (M$^+$)

Reference Example 10

3-oxo-8-(tetrahydropyrane-2-yloxy)-3,4-dihydro-2H-1,4-benzoxazine

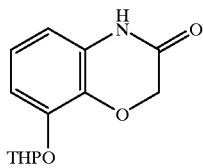

8-hydroxy-3-oxo-3,4-dihydro-2H-1,4-benzooxazine (740 mg) was dissolved in anhydrous DMF (1.5 ml), and dihydropyrane (1.0 g) and pyridinium p-toluenesulfonate (360 mg) were added to the-resultant solution, and the mixture was stirred at room temperature for 18 hours. The solvent was distilled off under reduced pressure, and the residue was poured into a saturated sodium bicarbonate aqueous solution, and then extracted with ethyl acetate. The resultant organic layer was washed with water, 5% citric acid, water, and saturated brine, dried over magnesium sulfate, and then concentrated. The residue was recrystallized from ethyl acetate to obtain the object compound (890 mg, yield 80%).

Colorless plate crystals: mp. 186° C. (recrystallized from ethyl acetate)

$^1$H-NMR (300 MHz, DMSO-d$_6$) δ1.54 (3H, m), 1.76 (3H, m), 3.52 ($^1$H, m), 3.79 (1H, m), 4.54 (2H, s), 5.40 (1H, t, J=4 Hz), 6.54 (1H, dd, J=1.5, 8 Hz), 6.76 (1H, dd, J=1.5, 8 Hz), 6.83 (1H, t, J=8 Hz), 10.67 (1H, bs).

IR (KBr method) 3104, 3080, 3008, 2944, 2892, 1684, 1615, 1520, 1495, 1452, 1406, 1354, 1288, 1253, 1214, 1207, 1180, 1125, 1087, 1048, 1036, 1021, 949, 917, 884, 814, 764 cm$^{-1}$ Mass (EI, m/e) 249 (M$^+$)

Reference Example 11

4-(2-(tetrahydropyran-2-yloxy)ethyl)-8-(tetrahydropyran-2-yloxy)-3,4-dihydro-2H-1,4-benzoxazine

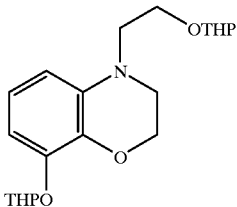

Sodium hydride (1.02 g) was washed with n-hexane, dried under reduced pressure, and the air was substituted by argon. A solution of 3-oxo-8-tetrahydropyranyloxy-3,4-dihydro-2H-1,4-benzoxazine (6.04 g) in anhydrous DMF (100 ml) was added to the sodium hydride, and the mixture was stirred at room temperature for 1 hour. 2-(2-bromoethoxy) tetrahydropyrane (7.60 g) was added to the resultant mixture, and the mixture was stirred at room temperature for 17.5 hours. The solvent was distilled off under reduced pressure, and the residue was poured into a 5% citric acid aqueous solution, and then extracted with ethyl acetate. The resultant organic layer was washed with water and saturated brine, dried over magnesium sulfate, and then concentrated. The residue was dissolved in THF (150 ml), and a 1.0M borane THF solution (60 ml) was added to the resultant solution, and the mixture was stirred at room temperature for 2 hours. A saturated sodium bicarbonate aqueous solution was added to the resultant solution to terminate reaction, and the reaction solution was extracted with ethyl acetate. The resultant organic layer was washed with water and saturated brine, dried over magnesium sulfate, and then concentrated. The residue was purified by medium-pressure column chromatography (silica gel; ethyl acetate/n-hexane=1:2) to obtain the object compound (7.01 g, yield 93%).

Colorless oily substance $^1$H-NMR (300 MHz, CDCl$_3$) δ1.50–2.10 (12H, m), 3.47 (5H, m), 3.62 (2H, m), 3.82 (1H, m), 3.91 (1H, m), 4.03 (1H, m), 4.25 (2H, t, J=4.5 Hz), 4.59 (1H, t, J=3 Hz), 5.36 (1H, t, J=3 Hz), 6.41 (1H, dd, J=1, 8 Hz), 6.52 (1H, dd, J=1, 8 Hz), 6.72 (1H, t, J=8 Hz).

IR (liquid film method) 2944, 2874, 1609, 1485, 1350, 1251, 1203, 1181, 1123, 1077, 1035, 996 cm$^{-1}$ Mass (El, m/e) 363 (M$^+$)

Reference Example 12

4-(2-hydroxyethyl)-8-hydroxy-3,4-dihydro-2H-1,4-benzoxazine

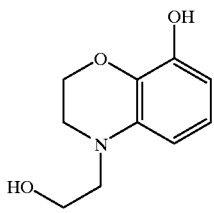

4-(2-(tetrahydropyran-2-yloxy)ethyl)-8-(tetrahydropyran-2-yloxy)-3,4-dihydro-2H-1,4-benzooxazine (3.89 g) was dissolved in methanol (80 ml), and pyridinium p-toluenesulfonate (520 mg) was added to the resultant solution, and the mixture was stirred at room temperature for 1.5 hours. The solvent was distilled off under reduced pressure, and the residue was poured into 5% citric acid, and then extracted with ethyl acetate. The resultant organic layer was washed with water and saturated brine, dried over magnesium sulfate, and then concentrated. The residue was recrystallized from ethyl acetate/n-hexane to obtain the object compound (2.00 g, yield 97%).

Colorless plate crystal: mp. 105.5° C. (recrystallized from ethyl acetate/n-hexane)

$^1$H-NMR (300 MHz, DMSO-$d_6$) δ3.26 (2H, t, J=5.5 Hz), 3.36 (2H, t, J=4 Hz)), 3.54 (2H, q, J=5.5 Hz), 4.10 (2H, t, J=4 Hz), 4.65 (1H, t, J=5.5 Hz)), 6.07 (1H, dd, J=1, 8 Hz), 6.15 (1H, dd, J=1, 8 Hz), 6.49 (1H, t, J=8 Hz), 8.49 (1H, s).

IR (KBr method) 3486, 3250, 2950, 2880, 1615, 1584, 1512, 1483, 1460, 1350, 1272, 1253, 1201, 1166, 1125, 1054, 980, 930, 901, 876, 832, 795, 766, 712 cm$^{-1}$ Mass (EI, m/e) 195 (M$^+$)

Reference Example 13

4-(2-hydroxyethyl)-8-hydroxy-3-oxo-3,4-dihydro-2H-1,4-benzoxazine

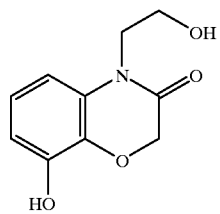

Sodium hydride (127 mg) was washed with n-hexane, dried under reduced pressure, and the air was substituted by argon. A solution of 3-oxo-(8-tetrahydropyrane-2-yloxy)-3,4-dihydro-2H-1,4-benzoxazine (529 mg) in anhydrous DMF (15 ml) was stirred into the sodium hydride, and the mixture was stirred at room temperature for 10 minutes. 2-(2-bromoethoxy)tetrahydropyrane (935 mg) was dissolved in DMF (3.0 ml), and the resultant solution was added to the resultant mixture, and the mixture was stirred at room temperature for 5.5 hours. The solvent was distilled off under reduced pressure, and the residue was poured into a 5% citric acid aqueous solution, and then extracted with ethyl acetate. The resultant organic layer was washed with water and saturated brine, dried over magnesium sulfate, and then concentrated. The residue was dissolved in methanol (50 ml), and p-toluenesulfonic acid hydrate (160 mg) was added to the resultant solution, and the mixture was stirred at room temperature for 2 hours. The solvent was distilled off under reduced pressure, and the residue was poured into 5% citric acid, and then extracted with ethyl acetate. The resultant organic layer was washed with water and saturated brine, dried over magnesium sulfate, and then concentrated. The residue was recrystallized from ethyl acetate/n-hexane to obtain the object compound (415 mg, yield 94%).

Colorless plate crystal: mp. 166° C. (recrystallized from ethyl acetate/n-hexane)

$^1$H-NMR (300 MHz, DMSOd$_6$) δ3.54 (2H, m), 3.90 (2H, t, J=6 Hz), 4.55 (2H, s), 4.85 (1H, br), 6.55 (1H, dd, J=1, 8 Hz), 6.70 (1H, dd, J=1, 8 Hz), 6.70 (1H, dd, J=1, 8 Hz), 6.82 (1H, t, J=8 Hz), 9.42 (1H, bs).

IR (KBr method) 3334, 1669, 1647, 1607, 1497, 1427, 1230, 1048, 727 cm$^{-1}$

Mass (EI, m/e) 209 (M$^+$)

Reference Example 14

Methyl(4-(2-hydroxyethyl)-3-oxo-3,4-dihydro-2H-1,4-benzoxazin-8-yloxy)acetate

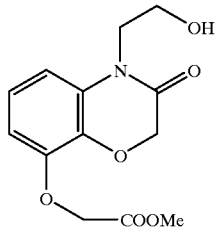

The same process as Reference Example 7 was repeated by except that 4-(2-hydroxyethyl)-8-hydroxy-3-oxo-3,4-dihydro-2H-1,4-benzoxazine (216 mg) was used to obtain the object compound (280 mg, yield 97%).

Colorless plate crystal: mp. 106° C. (recrystallized from ethylacetate/n-hexane)

$^1$H-NMR (300 MHz, CDCl$_3$) δ2.13 (1H, bs), 3.80 (3H, s), 3.94 (2H, bt, J=5.5 Hz)), 4.13 (2H, t, J=5.5 Hz), 4.70 (2H, s), 4.72 (2H, s), 6.62 (1H, dd, J=1, 8 Hz), 6.80 (1H, dd, J=1, 8 Hz), 6.96 (1H, t, J=8 Hz).

IR (KBr method) 3376, 2962, 2914, 2856, 1763, 1742, 1663, 1613, 1504, 1489, 1410, 1272, 1220, 1158, 1071, 1054, 1002, 785, 774 cm$^{-1}$ Mass (EI, m/e) 281 (M$^+$)

Reference Example 15

8-acetoxy-3-oxo-3,4-dihydro-2H-1,4-benzoxazine

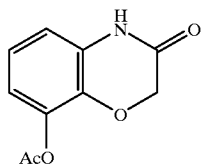

8-hydroxy-3-oxo-3,4-dihydro-2H-1,4-benzoxazine (100 mg) was dissolved in toluene (2 ml), and acetic anhydride (0.09 ml) and pyridine (2 ml) were added to the resultant solution at room temperature, and the mixture was stirred for 1.5 hours. The reaction solution was poured into a 1-N hydrochloric acid aqueous solution, and then extracted with ethyl acetate. The resultant organic layer was washed with water and saturated brine, dried over sodium sulfate, and then concentrated. The residue was recrystallized from ethyl acetate to obtain the object compound (97 mg, yield 77%). ethyl acetate/n-hexane)

$^1$H-NMR (300 MHz, CDCl$_3$) δ2.11 (3H, s), 4.61 (2H, s), 6.71 (1H, dd, J=8.0, 1.4 Hz)), 6.76 (1H, dd, J=8.0, 1.4 Hz), 6.94 (1H, t, J=8.0 Hz), 8.67 (1H, bs).

IR (KBr method) 3054, 1771, 1694, 1620, 1518, 1495, 1448, 1410, 1381, 1249, 1226, 1199, 1166, 1067, 901, 779 cm$^{-1}$ Mass (EI, m/e) 207 (M$^+$)

Reference Example 16

8-acetoxy-4-(2-(diphenylmethoxy)ethyl)-3-oxo-3,4-dihydro-2H-1,4-benzoxazine

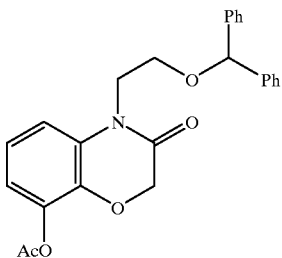

Anhydrous THF (15 ml) was added to sodium hydride (106 mg) to form a suspension, and a solution of 8-acetoxy-3-oxo-3,4-dihydro-2H-1,4-benzoxazine (498 mg) in anhydrous DMF (5 ml) was added to the resulting suspension, and the mixture was stirred at room temperature for 1 hour. 2-diphenylmethoxyethyl bromide (980 mg) was added to the mixture, and the mixture was stirred at room temperature overnight. The reaction solution was poured into a 3% citric acid aqueous solution, and then extracted with ethyl acetate. The resultant organic layer was washed with water and saturated brine, dried over sodium sulfate, and then concentrated. The residue was purified by medium-pressure column chromatography (solvent:ethyl acetate/cyclohexane=1/3) to obtain the colorless oily object compound (640 mg, yield 66%).

$^1$H-NMR (300 MHz, CDCl$_3$) δ2.33 (3H, s), 3.72 (2H, t, J=5.8 Hz), 4.17 (2H, t, J=5.8 Hz), 4.54 (2H, s), 5.34 (1H, s), 6.79 (1H, dd, J=8.2, 1.4 Hz)), 6.99 (1H, t, J=8.2 Hz), 7.18 (1H, dd, J=8.2, 1.4 Hz), 7.18–7.32 (10H, m).

IR (liquid film method) 3064, 3030, 2872, 1769, 1684, 1613, 1495, 1456, 1404, 1371, 1332, 1305, 1262, 1195, 1178, 1141, 1102, 1079, 1025, 1002, 911 cm$^{-1}$ Mass (EI, m/e) 417 (M$^+$)

Reference Example 17

8-acetoxy-4-(2-(1,1-diphenylethoxy)ethyl)-3-oxo-3,4-dihydro-2H-1,4-benzoxazine

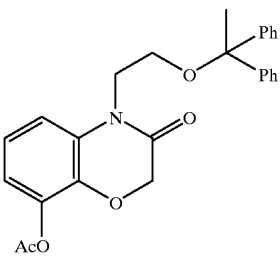

A solution of 2-(1,1-diphenylethoxy)-ethanol (606 mg) in THF (10 ml) was cooled to −40° C. n-butyllithium (1.47M hexane solution) (2.6 ml) and toluenesulfonyl chloride (715 mg) were added to the solution, and the mixture was stirred for 1.5 hours. The reaction solution was poured into water, and then extracted with ethyl acetate. The resultant organic layer was washed with water and saturated brine, dried over sodium sulfate, and concentrated to obtain a tosyl compound.

Anhydrous DMF (5 ml) was added to sodium hydride (84 mg) to form a suspension, and a solution of 8-acetoxy-3-oxo-3,4-dihydro-2H-1,4-benzooxazine (363 mg) in anhydrous DMF (5 ml) was stirred into the resulting suspension, and the mixture was stirred at room temperature for 30 minutes. The above tosyl compound was added to this mixture, and the mixture was stirred at room temperature overnight. The reaction solution was poured into a 5% citric acid aqueous solution, and then extracted with ethyl acetate containing 15% n-hexane. The resultant organic layer was washed with water and saturated brine, dried over sodium sulfate, and then concentrated. The residue was purified by medium-pressure column chromatography (solvent:ethyl acetate/cyclohexane=1/4) to obtain the colorless oily object compound (429 mg, yield 57%).

$^1$H-NMR (300 MHz, CDCl$_3$) δ1.81 (3H, s), 2.32 (3H, s), 3.52 (2H, t, J=5.8 Hz), 4.12 (2H, t, J=5.8 Hz), 4.53 (2H, s), 6.77 (1H, dd, J=8.2, 1.4 Hz), 6.94 (1H, t, J=8.2 Hz), 7.04 (1H, dd, J=8.2, 1.4 Hz), 7.18–7.29 (10H, m).

IR (KBr method) 3408, 1773, 1688, 1613, 1497, 1483, 1218, 1199, 1174, 1139 cm$^{-1}$ Mass (EI, m/e) 431 (M$^+$)

Reference Example 18

8-acetoxy-4-(4,4-diphenylpentyl)-3-oxo-3,4-dihydro-2H-1,4-benzoxazine

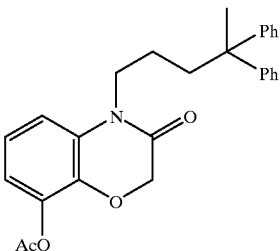

Pyridine (3 ml) and p-toluenesulfonyl chloride (300 mg) were added to a solution of 4,4-diphenylpentane-1-ol (391 mg) in dichloromethane (10 ml), and the mixture was stirred for 1.5 hours. The reaction solution was poured into 1-N hydrochloric acid, and then extracted with ethyl acetate. The resultant organic layer was washed with water and saturated brine, dried over sodium sulfate, and concentrated to obtain a tosyl compound.

Anhydrous DMF (5 ml) was added to sodium hydride (85 mg) to form a suspension, and a solution of 3-oxo-8-acetoxy-3,4-dihydro-2H-1,4-benzoxazine (507 mg) in anhydrous DMF (5 ml) was added to the resultant suspension, and the mixture was stirred at 0° C. for 40 minutes. A solution of the obtained tosyl compound in anhydrous DMF (2 ml) was added to the mixture, and the mixture was stirred at room temperature for 7 hours. The reaction solution was poured into a 5% citric acid aqueous solution, and then etracted with ethyl acetate containing 15% n-hexane. The resultant organic layer was washed with water and saturated brine, dried over sodium sulfate, and then concentrated. The residue was purified by medium-pressure column chromatography (solvent:ethyl acetate/cyclohexane=1/6) to obtain the object compound (428 mg, yield 61%).

$^1$H-NMR (300 MHz, CDCl$_3$) δ1.42–1.55 (4H, m), 1.61 (3H, s), 2.14–2.24 (2H, m), 2.31 (3H, s), 3.83 (2H, t, J=7.7 Hz), 4.55 (2H, s), 6.46 (1H, dd, J=8.2, 1.4 Hz), 6.74 (1H, dd, J=8.2, 1.4 Hz), 6.87 (1H, t, J=8.2 Hz), 7.13–7.21 (6H, m), 7.21–7.30 (4H, m).

IR (KBr method) 1688, 1611, 1495, 1481, 1446, 1408, 1375, 1328, 1299, 1261, 1224, 1205, 1183, 1137, 1042, 1029, 777, 748, 739, 698 cm$^{-1}$ Mass (EI, m/e) 429 (M$^+$)

Reference Example 19

8-acetoxy-4-(2-(diphenylmethoxy)ethyl)-3,4-dihydro-2H-1,4-benzoxazine

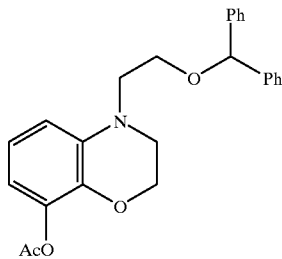

8-acetoxy-4-(2-(diphenylmethoxy)ethyl)-3-oxo-3,4-dihydro-2H-1,4-benzooxazine (630 mg) was dissolved in THF (10 ml), and a 1.0M borane THF solution (4.5 ml) was added to the resultant solution at 0° C., followed by stirring at room temperature for 4 hours. After water was added to the reaction solution to terminate reaction, the reaction solution was extracted with ethyl acetate. The resultant organic layer was washed with water, saturated sodium bicarbonate water, water and saturated brine, dried over sodium sulfate, and then concentrated. The residue was purified by medium-pressure column chromatography (solvent:ethyl acetate/cyclohexane=1/5) to obtain the colorless oily object compound (550 mg, yield 90%).

$^1$H-NMR (300 MHz, CDCl$_3$) δ2.30 (3H, s), 3.47 (2H, t, J=4.5 Hz), 3.54 (2H, t, J=5.5 Hz), 3.65 (2H, t, J=5.5 Hz), 4.18 (2H, t, J=4.5 Hz), 5.35 (1H, s), 6.38 (1H, dd, J=8.2, 1.4 Hz), 6.49 (1H, dd, J=8.2, 1.4 Hz), 6.73 (1H, t, J=8.2 Hz), 7.19–7.33 (10H, m).

IR (liquid film method) 3064, 3030, 2926, 2868, 1763, 1613, 1582, 1483, 1456, 1369, 1311, 1168, 1015 cm$^{-1}$ Mass (EI, m/e) 403 (M$^+$)

Reference Example 20

4-(2-(diphenylmethoxy)ethyl)-8-hydroxy-3,4-dihydro-2H-1,4-benzoxazine

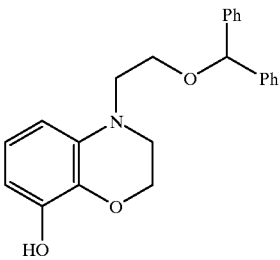

8-acetoxy-4-(2-(diphenylmethoxy)ethyl)-3,4-dihydro-2H-1,4-benzoxazine (482 mg) was dissolved in THF (2 ml) and a methanol (10 ml), and anhydrous potassium carbonate (250 mg) was added to the resultant solution, and the mixture was stirred at room temperature for 1 hour. The solvent was distilled off under reduced pressure, and the residue was poured into 5% citric acid, and then extracted with ethyl acetate. The resultant organic layer was washed with water and saturated brine, dried over sodium sulfate, and then concentrated to obtain the colorless oily object compound (429 mg, yield 99%).

$^1$H-NMR (300 MHz, CDCl$_3$) δ3.48 (2H, t, J=4.5 Hz), 3.53 (2H, t, J=5.5 Hz), 3.65 (2H, t, J=5.5 Hz), 4.23 (2H, t, J=4.5 Hz), 5.34 (1H, s), 5.40 (1H, s), 6.20 (1H, dd, J=8.0, 1.1 Hz), 6.32 (1H, dd, J=8.0, 1.1 Hz), 6.67 (1H, t, J=8.0 Hz), 7.20–7.34 (10H, m).

IR (liquid film method) 3514, 3062, 3030, 2928, 2870, 1736, 1620, 1589, 1510, 1485, 1454, 1350, 1249, 1207, 1166, 1096, 1073, 1040 cm$^{-1}$ Mass (EI, m/e) 361 (M$^+$)

Reference Example 21

4-(2-(1,1-diphenylethoxy)ethyl)-8-hydroxy-3,4-dihyro-2H-1,4-benzoxazine

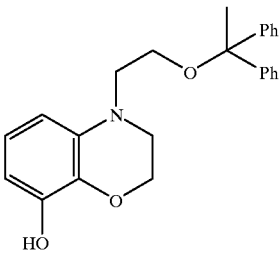

8-acetoxy-3,4-(2-(1,1-diphenylethoxy)ethyl)-3-oxo-3,4-dihydro-2H-1,4-benzoxazine (386 mg) was dissolved in THF (10 ml), and a 1.0M borane THF solution (3 ml) was added to the resultant solution at 0° C., followed by stirring at room temperature for 4 hours. After water was added to the reaction solution to terminate reaction, the reaction solution was extracted with ethyl acetate. The resultant organic layer was washed with water, sodium bicarbonate water, water and saturated brine, dried over sodium sulfate, and then concentrated. The residue was roughly purified by medium-pressure column chromatography (solvent:ethyl acetate/cyclohexane=1/5). The thus-obtained oily substance was dissolved in THF (1 ml) and methanol (10 ml), and anhydrous potassium carbonate (170 mg) was added to the resultant solution, and the mixture was stirred at room temperature for 1 hour. The solvent was distilled off under reduced pressure, and the residue was poured into 5% citric acid, and then extracted with ethyl acetate. The resultant organic layer was washed with water and saturated brine, dried over sodium sulfate, and concentrated to obtain the colorless oily object compound (339 mg, yield 99%).

$^1$H-NMR (300 MHz, CDCl$_3$) δ1.83 (3H, s), 3.40–3.52 (6H, m), 4.25 (2H, t, J=4.5 Hz), 5.38 (1H, s), 6.11 (1H, dd, J=8.1, 1.4 Hz), 6.30 (1H, dd, J=8.1, 1.4 Hz), 6.63 (1H, t, J=8.1 Hz), 7.17–7.36 (10H, m).

IR (KBr method) 3510, 2934, 2874, 1620, 1591, 1512, 1485, 1448, 1348, 1251, 1209, 1079, 1062, 1031, 756, 702 cm$^{-1}$ Mass (EI, m/e) 375 (M$^+$)

Reference Example 22

4-(4,4-diphenylpentyl)-8-hydroxy-3-oxo-3,4-dihydro-2H-1,4-benzoxazine

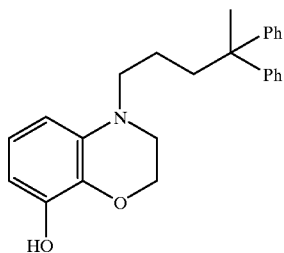

8-acetoxy-4-(4,4-diphenylpentyl)-3-oxo-3,4-dihydro-2H-1,4-benzoxazine (424 mg) was dissolved in THF (10 ml), and a 1.0M borane THF solution (4 ml) was added to the resultant solution at 0° C., followed by stirring at room temperature overnight. After water was added to the reaction solution to terminate reaction, the reaction solution was extracted with ethyl acetate. The resultant organic layer was washed with water, sodium bicarbonate water, water and saturated brine, dried over sodium sulfate, and then concentrated. The thus-obtained oily substance was dissolved in THF (1 ml) and methanol (10 ml), and anhydrous potassium carbonate (170 mg) was added to the resultant solution, and the mixture was stirred at room temperature for 30 minutes. The solvent was distilled off under reduced pressure, and the residue was poured into 5% citric acid, and then extracted with ethyl acetate. The resultant organic layer was washed with water and saturated brine, dried over sodium sulfate, and concentrated to obtain the colorless oily object compound (391 mg, yield 99%).

$^1$H-NMR (300 MHz, CDCl$_3$) δ1.36–1.48 (2H, m), 1.63 (3H, s), 2.08–2.16 (2H, m), 3.15 (2H, t, J=7.3 Hz), 3.19 (2H, t, J=4.4 Hz), 4.22 (2H, t, J=4.4 Hz), 5.36 (1H, s), 6.10 (1H, dd, J=8.1, 1.1 Hz), 6.31 (1H, dd, J=8.1, 1.1 Hz), 6.66 (1H, t, J=8.1 Hz), 7.14–7.21 (6H, m), 7.23–7.29 (4H, m).

IR (KBr method) 3500, 2974, 1618, 1591, 1487, 1446, 1377, 1354, 1303, 1249, 1212, 1199, 1164, 1091, 1075, 1044, 1029, 909, 756, 727, 714, 694 cm$^{-1}$ Mass (EI, m/e) 373 (M$^+$)

Reference Example 23

N-diphenylmethyl-2-chloroacetamide

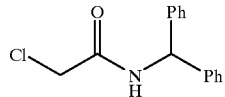

A solution of N-diphenylmethylamine (1103 mg) in methylene chloride (20 ml) was stirred at 0° C. Triethylamine (1.70 ml) and chloroacetyl chloride (0.72 ml) were added to the solution, and the mixture was stirred at 0° C. for 40 minutes. After water (20 ml) was added to the reaction mixture, the mixture was extracted with ethyl acetate. The resultant organic layer was washed with saturated brine, dried over sodium sulfate, and concentrated. The residue was purified by silica gel column chromatography (developing solvent:n-hexane/ethyl acetate=5/1) to obtain the object compound (1522 mg, yield 97%).

$^1$H-NMR (300 MHz, CDCl$_3$) δ4.13 (2H, s), 6.26 (1H, d, J=8.1 Hz), 7.13–7.40 (11H, m).

IR (KBr method) 3204, 3042, 1554, 1495, 1454, 1420, 1237, 1090, 1060, 1031, 987, 925, 857, 786, 762, 748, 703 cm$^{-1}$ Mass (EI, m/e) 259 (M$^+$)

Reference Example 24

N-diphenylmethyl-2-(8-hydroxy-3-oxo-3,4-dihydro-2H-1,4-benzoxazin-4-yl)acetamide

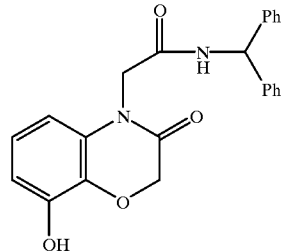

A solution of 8-(tetrahydropyrane-2-yloxy)-3-oxo-3,4-dihydro-2H-1,4-benzooxazine (538 mg) in DMF (15 ml) was stirred at 0° C., and t-BuOK (333 mg) was added to the solution, and the mixture was stirred for 10 minutes. A solution of N-diphenylmethyl-2-chloroacetamide (841 mg) DMF (5 ml) was then added to the resultant mixture, and the mixture was stirred at room temperature for 160 minutes. After water (25 ml) was added to the reaction mixture, the precipitated solid was filtered off, and the filtrate was then extracted with ethyl acetate. The resultant organic layer was washed with saturated brine, dried over sodium sulfate, and concentrated. The thus-obtained residue and the solid filtered off were combined, and the combined mixture was suspended in methanol (200 ml). p-Toluenesulfonic acid-hydrate (156 mg) was added to the suspension, and the mixture was stirred at room temperature for 15 hours. The precipitated solid was filtered off, and the filtrate was concentrated. The residue was purified by silica gel column chromatography (developing solvent:n-hexane/ethyl acetate=2/3) to obtain the object compound (738 mg, yield 88%).

$^1$H-NMR (300 MHz, CDCl$_3$) δ4.61 (2H, s), 4.72 (2H, s), 5.46 (1H, s), 6.21 (1H, d, J=8.1 Hz), 6.67–6.78 (3H, m), 6.93 (1H, t, J=8.3 Hz), 7.10–7.17 (4H, m), 7.21–7.33 (6H, m).

IR (KBr method) 3280, 1661, 1543, 1494, 1482, 1421, 1375, 1350, 1236, 1176, 1150, 1086, 1043, 977, 956, 823, 769, 750, 724, 700 cm$^{-1}$ Mass (EI m/e) 388 (M$^+$)

Reference Example 25

3-oxo-4-(2-(benzyloxy)ethyl)-8-(tetrahydropyran-2-yloxy)-3,4-dihydro-2H-1,4-benzoxazine

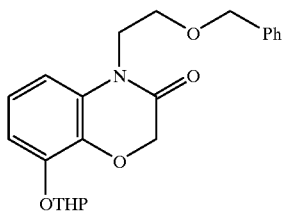

Anhydrous DMF (12 ml) was added to sodium hydride (353 mg) to form a suspension, and a solution of 3-oxo-8-(tetrahydropyran-2-yloxy)-3,4-dihydro-2H-1,4-benzoxazine (2.02 g) in anhydrous DMF (15 ml) was added to the resultant suspension at 0° C., and the mixture was stirred at room temperature for 1 hour. A solution of benzyl-2-bromoethyl ether in anhydrous DMF (5 ml) was added to the mixture, and the mixture was stirred at room temperature for 21 hours. The solvent was distilled off under reduced pressure, and the residue was then poured into a saturated ammonium chloride aqueous solution, and then extracted with ethyl acetate. The resultant organic layer was dried over magnesium sulfate, and concentrated. The residue was purified by column chromatography (silica gel:hexane/ethyl acetate=2/1) to obtain the object compound (1.99 g, yield 65%).

$^1$H-NMR (300 MHz, CDCl$_3$) δ1.59–1.75 (3H, m), 1.82–2.08 (3H, m), 3.57–3.64 (1H, m), 3.73 (2H, t, J=5.9 Hz), 3.93–4.01 (1H, m), 4.14 (2H, t, J=5.9 Hz), 4.53 (2H, s), 4.61 (2H, s), 5.42 (1H, t, J=3.3 Hz), 6.86–6.93 (3H, m), 7.25–7.35 (5H, m).

IR (liquid film method) 3585, 3061, 3031, 2945, 2869, 1736, 1686, 1609, 1590, 1481, 1454, 1401, 1358, 1318, 1273, 1204, 1183, 1149, 1115, 1038, 952, 917, 873, 818, 770, 737, 698, 672 cm$^{-1}$ Mass (EI m/e) 383 (M$^+$)

Reference Example 26

8-hydroxy-3-oxo-4-(2-(benzyloxy)ethyl)-3,4-dihydro-2H-1,4-benzoxazine

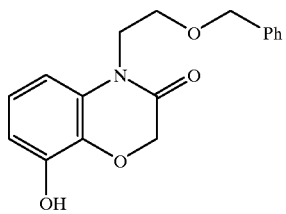

3-oxo-4-(2-(benzyloxy)ethyl)-8-(tetrahydropyrane-2-yloxy)-3,4-dihydro-2H-1,4-benzoxazine (1.89 g) was dissolved in methanol (100 ml), and pyridinium p-toluenesulfonate (126 mg) was added to the resultant solution, and the mixture was refluxed for 12 hours. The solvent was distilled off under reduced pressure, and the residue was poured into a saturated sodium bicarbonate aqueous solution, and then extracted with ethyl acetate. The resultant organic layer was dried over magnesium sulfate, and concentrated. The residue was purified by column chromatography (silica gel:hexane/ethyl acetate=1/1) to obtain the object compound (1.18 g, yield 80%).

$^1$H-NMR (300 MHz, CDCl$_3$) δ3.73 (2H, t, J=5.9 Hz), 4.14 (2H, t, J=5.9 Hz), 4.53 (2H, s), 4.63 (2H, s), 5.61 (1H, s), 6.68–6.76 (2H, m), 6.87–6.92 (1H, m), 7.23–7.34 (5H, m).

IR (liquid film method) 3353, 3031, 2866, 1734, 1683, 1612, 1492, 1453, 1405, 1373, 1341, 1227, 1173, 1142, 1100, 1044, 1006, 807, 772, 734, 699 cm$^{-1}$ Mass (EI, m/e) 299 (M$^+$)

Reference Example 27

3-oxo-4-(2-(benzyloxy)ethyl)-8-(trifluoromethanesulfonyloxy)-3,4-dihydro-2H-1,4-benzoxazine

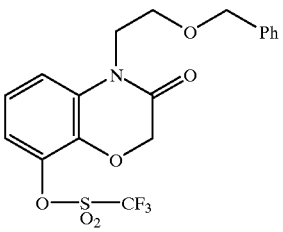

8-hydroxy-3-oxo-4-(2-(benzyloxy)ethyl)-3,4-dihydro-2H-1,4-benzoxazine (1.10 g) was dissolved in dichloromethane (18 ml), and 2,6-lutidine (0.85 ml) and trifluoromethanesulfonic anhydride (1.50 ml) were added to the resultant solution, and the mixture was stirred at −78° C. for 1.5 hours. The reaction solution was poured into a saturated ammonium chloride aqueous solution, and then extracted with ethyl acetate. The resultant organic layer was dried over magnesium sulfate, and concentrated. The residue was purified by column chromatography (silica gel:hexane/ethyl acetate=2/1) to obtain the object compound (1.40 g, yield 89%).

$^1$H-NMR (300 MHz, CDCl$_3$) δ3.76 (2H, t, J=5.6 Hz), 4.14 (2H, t, J=5.6 Hz), 4.52 (2H, s), 4.67 (2H, s), 6.94–7.06 (2H, m), 7.21–7.34 (6H, m).

IR (liquid film method) 3033, 2866, 1694, 1615, 1500, 1478, 1425, 1333, 1303, 1212, 1168, 1139, 1043, 1001, 900, 850, 830, 798, 779, 758, 734, 700, 665, 598 cm$^{-1}$ Mass (EI, m/e) 431 (M$^+$)

Reference Example 28

Methyl (E)-3-(3-oxo-4-(2-(benzyloxy)ethyl)-3,4-dihydro-2H-1,4-benzoxazin-8-yl)acrylate

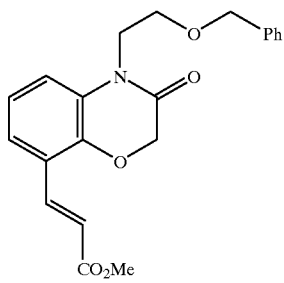

3-oxo-4-(2(benzyloxy)ethyl)-8-(trifluoromethanesulfonlyloxy)-3,4-dihydro-2H-1,4-benzoxazine (1.32 g) was dissolved in anhydrous DMF (12 ml), and triethylamine (2.6 ml), lithium chloride (388 mg), tris(2-methylphenyl)phosphine (466 mg), palladium acetate (67 mg) and methyl acrylate (0.70 ml) were added to the resultant solution, and the mixture was stirred at 100° C. for 14 hours. The reaction mixture was filtered, and then the residue was washed with water and a saturated brine, and extracted with ethyl acetate. The resultant organic layer was dried over magnesium sulfate, and concentrated. The residue was purified by column chromatography (silica gel:hexane ethyl acetate=2/1) to obtain the object compound (1.09 g, yield 97%).

$^1$H-NMR (300 MHz, CDCl$_3$) δ3.75 (2H, t, J=5.6 Hz), 3.82 (3H, s), 4.15 (2H, t, J=5.6 Hz), 4.53 (2H, s), 4.65 (2H, s), 6.53 (1H, d, J=16.2 Hz), 7.01 (1H, t, J=8.0 Hz), 7.23–7.33 (7H, m), 7.95 (1H, d, J=16.2 Hz).

IR (liquid film method) 3585, 3031, 2998, 2950, 2864, 1686, 1634, 1585, 1482, 1454, 1435, 1402, 1315, 1273, 1172, 1094, 1043, 988, 934, 866, 810, 787, 740, 699, 651 cm$^{-1}$ Mass (EI, m/e) 367 (M$^+$)

Reference Example 29

Methyl 3-(4-(2-hydroxyethyl)-3-oxo-3,4-dihydro-2H-1,4-benzoxazin-8-yl)propionate

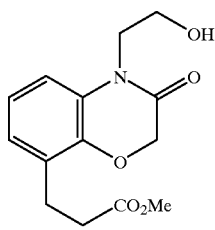

10% Pd-C (310 mg) was dissolved in ethanol (10 ml), and deaerated, and the air in a reactor was replaced by argon. A solution of methyl (E)-3-(3-oxo-4-(2-benzyloxy)ethyl)-3,4-dihydro-2H-1,4-benzoxazin-8-yl)acrylate (1.04 g) in ethanol (14 ml) was added to the resultant solution. A 0.1M hydrochloric acid aqueous solution (2 ml) was then added to the mixture, and the mixture was stirred at room temperature for 37 hours in the reactor in which the atmosphere was replaced by hydrogen. The reaction mixture was filtered with Celite, and then the filtrate was concentrated. The residue was purified by column chromatography (silica gel:hexane/ethyl acetate=1/3) to obtain the object compound (747 mg, yield 95%).

$^1$H-NMR (300 MHz, CDCl$_3$) δ2.61 (2H, t, J=7.7 Hz), 2.96 (2H, t, J=7.7 Hz), 3.67 (3H, s), 3.93 (2H, t, J=5.5 Hz), 4.12 (2H, t, J=5.5 Hz), 4.63 (2H, s), 6.90–7.01 (3H, m).

IR (liquid membrane method) 3450, 2952, 2888, 2084, 1736, 1681, 1611, 1590, 1481, 1438, 1408, 1370, 1304, 1273, 1227, 1201, 1174, 1129, 1089, 1051, 983, 944, 907, 840, 809, 783, 743, 711 cm$^{-1}$ Mass (EI, m/e) 279 (M$^+$)

Reference Example 30

4-(3-(tert-butyldimethylsilyloxy)propyl)-3-oxo-8-(tetrahydropyran-2-yloxy)-3,4-dihydro-2H-1,4-benzoxazine

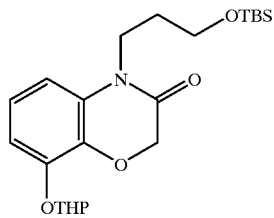

3-oxo-8-(tetrahydropyran-2-yl)-3,4-dihydro-2H-1,4-benzoxazine (2.0 g) was dissolved in DMF (25 ml), and potassium t-butoxide (1.1 g) was added to the resultant solution, and the mixture was stirred at 0° C. for 15 minutes and then at room temperature for 15 minutes. The reaction solution was cooled to 0° C., and 3-(tert-butyldimethylsilyloxy)-1-bromopropane (2.1 ml) was then added to the reaction solution, and the mixture was stirred for 3 hours at room temperature. The reaction solution was diluted with ethyl acetate, washed with a saturated ammonium chloride aqueous solution and saturated brine, and then dried over anhydrous sodium sulfate. Then, the solvent was distilled off under reduced pressure, and the resultant residue was purified by column chromatography (silica gel:ethyl acetate/n-hexane=3:17) to obtain the object compound (2.55 g, yield 75%).

Pale yellow oily substance $^1$H-NMR (300 MHz, CDCl$_3$) δ0.07 (6H, s), 0.93 (9H, s), 1.60–1.75 (2H, m), 1.82–2.12 (6H, m), 3.56–3.65 (1H, m), 3.70 (2H, t, J=5.7 Hz), 3.92–4.06 (3H, m), 4.62 (2H, s), 5.42 (1H, t, J=3.0 Hz), 6.83–6.96 (3H, m).

IR (liquid film method) 2951, 2856, 1688, 1610, 1481, 1404, 1358, 1275, 1202, 1181, 1145, 1099, 1038, 1022, 950, 918, 835, 776 cm$^{-1}$ Mass (EI, m/e) 421 (M$^+$)

Reference Example 31

4-(3-hydroxypropyl)-3-oxo-8-(tetrahydropyran-2-yloxy)-3,4-dihydro-2H-1,4-benzoxazine

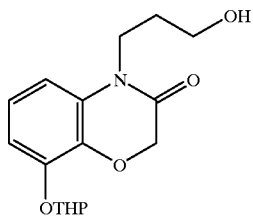

4-(3-(tetra-butyldimethylsilyloxy)propyl)-3-oxo-8-(tetrahydropyran-2-yloxy)-3,4-dihydro-2H-1,4-benzoxazine (2.75 g) was dissolved in THF (20 ml), and tetrabutylammonium fluoride (1.0M in THF) was then added to the resultant solution at 0° C., followed by stirring for 14.5 hours at room temperature. The reaction solution was diluted with ethyl acetate, washed with saturated brine, and then dried over anhydrous sodium sulfate. Then, the solvent was distilled off under reduced pressure, and the resultant residue was purified by column chromatography (silica gel:ethyl acetate/n-hexane=1:1 to 3:1) to obtain the object compound (2.0 g, yield 99.8%).

Colorless oily substance $^1$H-NMR (300 MHz, CDCl$_3$) δ1.60–1.77 (2H, m), 1.82–2.12 (6H, m), 2.99 (1H, t, J=6.8 Hz), 3.54–3.65 (3H, m), 3.91–4.02 (1H, m), 4.10 (2H, t, J=6.2 Hz), 4.67 (2H, s), 5.43 (1H, t, J=3.0 Hz), 6.76 (1H, dd, J=6.9, 3.0 Hz), 6.90–7.00 (2H, m).

IR (liquid film method) 3447, 2946, 1680, 1610, 1481, 1409, 1356, 1270, 1180, 1143, 1119, 1037, 957, 908, 872, 817, 754 cm$^{-1}$ Mass (EI, m/e) 307 (M$^+$)

Reference Example 32

4-(3-azidopropyl)-3-oxo-8-(tetrahydropyran-2-yloxy)-3,4-dihydro-2H-1,4-benzoxazine

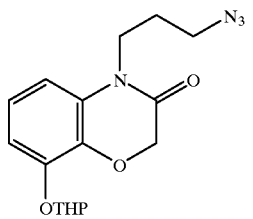

4-(3-hydroxypropyl)-3-oxo-8-(tetrahydropyran-2-yloxy)-3,4-dihydro-2H-1,4-benzoxazine (2.0 g) was dissolved in dichloromethane (20 ml), and triethylamine (1.27 ml) and a methanesulfonyl chloride (0.6 ml) were added to the resultant solution at 0° C., followed by stirring for 2 hours. The reaction solution was diluted with chloroform, washed with saturated brine, and then dried over anhydrous sodium sulfate. Then, the solvent was distilled off under reduced pressure to obtain a crude mesyl compound. The crude mesyl compound was dissolved in DMF (20 ml), and sodium azide (510 mg) was added to the resultant solution, and the mixture was stirred at room temperature for 15 hours. The reaction solution was diluted with ethyl acetate, washed with saturated brine, and then dried over anhydrous sodium sulfate. The solvent was distilled off under reduced pressure, and the resultant residue was purified by column chromatography (silica gel: ethyl acetate/n-hexane=1:9) to obtain the object compound (2.07 g, yield 96%).

Colorless oily substance $^1$H-NMR (300 MHz, CDCl$_3$) δ1.60–1.76 (2H, m), 1.82–2.09 (6H, m), 3.42 (2H, t, J=6.5 Hz), 3.57–3.66 (1H, m), 3.92–4.06 (3H, m), 4.63 (2H, s), 5.43 (1H, t, J=3.2 Hz), 6.70 (1H, dd, J=7.8, 1.8 Hz), 6.89–7.01 (2H, m).

IR (liquid film method) 2946, 2874, 2098, 1686, 1609, 1481, 1404, 1355, 1271, 1200, 1180, 1145, 1119, 1075, 1036, 953, 921, 872, 817, 755 cm$^{-1}$ Mass (EI, m/e) 332 (M$^+$)

Reference Example 33

4-(3-(2-naphthoylamino)propyl)-3-oxo-8-(tetrahydropyrane-2-yloxy)-3,4-dihydro-2H-1,4-benzoxazine

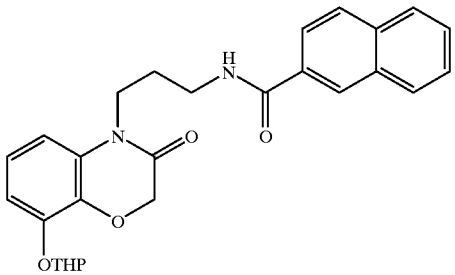

A solution of 4-(3-azidopropyl)-3-oxo-8-(tetrahydropyran-2-yloxy)-3,4-dihydro-2H-1,4-benzoxazine (1.0 g) in ethanol (10 ml) was added to a suspension of 10% palladium carbon (containing 50% water) (100 mg) in ethanol (20 ml), and the mixture was stirred at room temperature for 22 hours under a hydrogen atmosphere. The reaction solution was filtered with Celite, and the solvent was distilled off under reduced pressure to obtain a crude amine. The thus-obtained crude amine was dissolved in DMF (10 ml), and 2-naphthalenecarboxylic acid (780 mg) and 1-(3-(dimethylamino)propyl)-3-ethylcarbodiimide hydrochloride (865 mg) were added to the resultant solution, and the mixture was stirred at room temperature for 19 hours. The reaction solution was diluted with ethyl acetate, washed with saturated brine, and then dried over anhydrous sodium sulfate. The solvent was distilled off under reduced pressure, and the resultant residue was purified by column chromatography (silica gel:ethyl acetate/n-hexane=3:2) to obtain the object compound (717 mg, yield 55%).

Colorless oily substance $^1$H-NMR (300 MHz, CDCl$_3$) δ1.55–2.13 (8H, m), 3.50 (2H, dd, J=12.0, 6.3 Hz), 3.57–3.67 (1H, m), 3.90–4.02 (1H, m), 4.08–4.17 (2H, m), 4.71 (2H, s), 5.43 (1H, t, J=3.3 Hz), 6.75 (1H, dd, J=7.1, 2.6 Hz), 6.92–7.02 (2H, m), 7.50–7.64 (3H, m), 7.84–8.01 (4H, m), 8.44 (1H, s).

IR (liquid film method) 2943, 1684, 1636, 1534, 1480, 1411, 1291, 1186, 1147, 1021, 958, 819, 772, 483 cm$^{-1}$ Mass (EI, m/e) 460 (M$^+$)

Reference Example 34

4-(3-(2-naphthylmethylamino)propyl)-8-hydroxy-3,4-dihydro-2H-1,4-benzoxazine

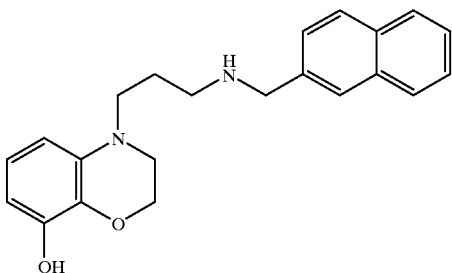

4-(3-(2-naphthoylamino)propyl)-3-oxo-8-(tetrahydropyran-2-yloxy)-3,4-dihydro-2H-1,4-benzooxazine (398 mg) was dissolved in methanol (5 ml), and a 1N hydrochloric acid aqueous solution was added to the resultant solution, and the mixture was stirred at 0° C. for 1 hour. The reaction solution was extracted with ethyl acetate, and the resultant organic layer was washed with saturated brine, and then dried over anhydrous sodium sulfate. The solvent was distilled off under reduced pressure, and the resultant residue was dissolved in THF (5 ml). A borane THF complex (1.0 M in THF, 2.8 ml) was added to the resultant solution, and then the mixture was refluxed under heating for 3.5 hours. A saturated sodium bicarbonate aqueous solution was added to the reaction solution, and the mixture was then extracted with ethyl acetate. The resultant organic layer was washed with saturated brine, and then the solvent was distilled off under reduced pressure. The resultant residue was purified by column chromatography (silica gel:ethyl acetate/n-hexane=3:7) to obtain the object compound (166 mg, yield 52%).

Colorless oily substance $^1$H-NMR (300 MHz, CDCl$_3$) δ1.76–1.91 (1H, m), 2.16–2.33 (1H, m), 2.70–2.83 (1H, m), 2.85–2.97 (1H, m), 3.00–3.11 (2H, m), 3.13–3.24 (1H, m), 3.31 (1H, dd, J=12.1, 4.9, 2.7 Hz), 3.70 (1H, dd, J=13.5, 9.1 Hz), 4.00–4.17 (2H, m), 4.31 (1H, dd, J=13.5, 3.6 Hz), 4.53 (1H, br. s), 5.42 (1H, s), 6.01 (1H, dd, J=8.2, 1.4 Hz), 6.43 (1H, dd, J=8.2, 1.4 Hz), 6.57 (1H, t, J=8.2 Hz), 7.17 (1H, dd, J=8.2, 1.9 Hz), 7.46–7.56 (2H, m), 7.58 (1H, br. s), 7.66–7.75 (2H, m), 7.80–7.87 (1H, m).

IR (liquid film method) 3518, 2945, 1617, 1509, 1482, 1350, 1166, 1074, 1042, 909, 859, 821, 759, 731 cm$^{-1}$ Mass (EI, m/e) 348 (M$^+$)

Reference Example 35

6-acetoxy-2-oxo-2,3,4,5-tetrahydro-1H-benzazepine

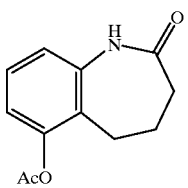

5-hydroxy-1-tetralone (506 mg) was dissolved in trifluoroacetic acid (10 ml) in a 50-ml short-neck flask with a condenser in an argon atmosphere, followed by stirring at room temperature. Sodium azide (254 mg) was added to the resultant solution, and the mixture was refluxed under heating. Since the progress of reaction stopped, the reaction solution was poured into water (20 ml), neutralized with a sodium bicarbonate aqueous solution, and then extracted with ethyl acetate. The combined organic layers were washed with saturated brine, dried over anhydrous sodium sulfate, and then concentrated to obtain a residue. The thus-obtained residue was dissolved in methylene chloride (5 ml) and pyridine (2 ml) in a 100-ml short-neck flask, and the resultant solution was stirred at room temperature. Acetic anhydride (0.45 ml) was added to the resultant solution, and the mixture was stirred at room temperature. After disappearance of the raw materials was confirmed, the reaction solution was added to a saturated ammonium chloride aqueous solution (30 ml), and then extracted with ethyl acetate. The resultant organic layer was washed with saturated brine, dried over anhydrous sodium sulfate, and then concentrated. The resultant residue was purified by column chromatography (silica gel:hexane/ethyl acetate=1/1) to obtain the object compound (416 mg, yield a 61%).

$^1$H-NMR (300 MHz, CDCl$_3$) δ1.99–2.07 (2H, m), 2.14 (2H, t, J=6.9 Hz), 2.32 (3H, s), 2.56 (2H, t, J=7.2 Hz), 6.89 (2H, d, J=8.1 Hz), 7.24 (1H, t, J=8.1 Hz), 9.66 (1H, s).

IR (KBr method) 3188, 1758, 1676, 1642, 1580, 1473, 1381, 1220, 1176, 1067, 1021, 777 cm$^{-1}$ Mass (EI, m/e) 219 (M$^+$)

Reference Example 36

Methyl (6-acetoxy-2-oxo-2,3,4,5-tetrahydro-1H-1-benzazepin-1-yl)acetate

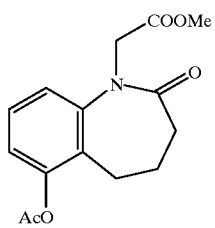

6-acetoxy-2-oxo-2,3,4,5-tetrahydro-1H-1-benzoazepine (252 mg) was dissolved in DMF (5 ml), and the resultant solution was stirred at room temperature. Potassium carbonate (509 mg) and methyl bromoacetate (0.22 ml) were added to the solution at room temperature. After disappearance of the raw materials was confirmed, water (20 ml) was added to the reaction solution, and the mixture was then extracted with ethyl acetate. The resultant organic layer was washed with saturated saline, dried over anhydrous sodium sulfate, and then concentrated. The resultant residue was purified by column chromatography (silica gel:hexane/ethyl acetate=1/1) to obtain the object compound ml (333 mg, yield 99%).

$^1$H-NMR (300 MHz, CDCl$_3$) δ1.95–2.30 (2H, m), 2.30–2.41 (2H, m), 2.35 (3H, s), 2.78–2.90 (2H, m), 3.75 (3H, s), 4.51 (2H, s), 6.96 (1H, dd, J=8.1, 0.9 Hz), 7.06 (1H, dd, J=8.1, 0.9 Hz), 7.27 (1H, t, J=8.1 Hz).

IR (liquid film method) 2958, 1750, 1661, 1607, 1586, 1437, 1412, 1379, 1172, 1110, 1083, 1015, 980, 920, 731 cm$^{-1}$ Mass (EI, m/e) 291 (M$^+$)

Reference Example 37

1-(2-hydroxyethyl)-6-hydroxy-2,3,4,5-tetrahydro-1H-1-benzazepine

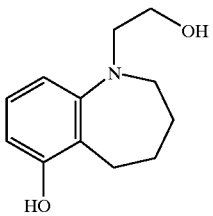

Methyl (6-acetoxy-2-oxo-2,3,4,5-tetrahydro-1H-1-benzazepin-1-yl)acetate (1080 mg) was dissolved in THF (15 ml) under an argon atmosphere, and the resultant solution was stirred at 0° C. Lithium aluminum hydride (355 mg) was added to the solution, and the mixture was stirred at 0° C. After disappearance of the raw materials was confirmed, the reaction solution was added to water (100 ml), and then extracted with ethyl acetate. The resultant organic layer was washed with saturated brine, dried over anhydrous sodium sulfate, and then concentrated. The resultant residue was purified by column chromatography (silica gel:hexane/ethyl acetate=2/1) to obtain the object compound (624 mg, yield 81%).

$^1$H-NMR (300 MHz, CDCl$_3$) δ1.55–1.66 (2H, m), 1.68–1.81 (2H, m), 2.63 (1H, br s), 2.82–2.90 (2H, m), 2.90–2.97 (2H, m), 3.31 (2H, t, J=5.3 Hz), 3.71 (2H, t, J=5.3 Hz), 5.31 (1H, br s), 6.47 (1H, dd, J=8.1, 1.2 Hz), 6.57 (1H, d, J=8.1 Hz), 6.98 (1H, t, J=8.1 Hz).

IR (liquid film method) 2926, 2850, 1605, 1582, 1495, 1468, 1305, 1257, 1230, 1141, 1029, 1004, 785, 733 cm$^{-1}$ Mass (EI, m/e) 207 (M$^+$)

Reference Example 38

Methyl (1-(2-hydroxyethyl)-2,3,4,5-tetrahydro-1H-1-benzazepin-6-yloxy)acetate

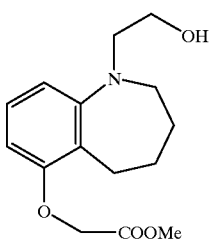

1-(2-hydroxyethyl)-6-hydroxy-2,3,4,5-tetrahydro-1H-1-benzazepine (52 mg) was dissolved in DMF (3 ml), and the resultant solution was stirred at room temperature. Potassium carbonate (122 mg) and methyl bromoacetate (0.035 ml) were added to the solution, and the mixture was stirred at room temperature. After disappearance of the raw materials was confirmed, water (20 ml) was added to the reaction solution, and the mixture was then extracted with ethyl acetate. The resultant organic layer was washed with saturated brine, dried over anhydrous sodium sulfate, and then concentrated. The resultant residue was purified by column chromatography (silica gel:hexane/ethyl acetate=2/1) to obtain the object compound (47 mg, yield 67%).

$^1$H-NMR (300 MHz, CDCl$_3$) δ1.55–1.67 (2H, m), 1.68–1.80 (2H; m), 2.51 (1H, br s), 2.93–2.98 (4H, m), 3.31 (2H, t, J=5.1 Hz), 3.69 (2H, t, J=5.1 Hz), 3.80 (3H, s), 4.62 (2H, s), 6.46 (1H, dd, J=8.1, 0.9 Hz), 6.67 (1H, dd, J=8.1, 0.9 Hz), 7.06 (1H, t, J=8.1 Hz).

IR (liquid film method) 2928, 2858, 1760, 1599, 1580, 1470, 3:441, 1290, 1212, 1181, 1145, 1125, 1098, 1046, 733 cm$^{-1}$ Mass (EI, m/e) 279 (M$^+$)

Reference Example 39

5-(t-butyldimethylsiloxy)quinoline

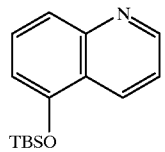

5-hydroxyquinoline (101 mg) was dissolved in DMF (5 ml) under an argon atmosphere, and the resultant solution was stirred at room temperature. Imidazole (113 mg) and t-butyldimethylsilyl chloride (162 mg) were added to the solution, and the mixture was stirred at room temperature. After disappearance of the raw materials was confirmed, water (5 ml) was added to the reaction solution, and the mixture was then extracted with ethyl acetate. The resultant organic layer was washed with saturated brine, dried over anhydrous sodium sulfate, and then concentrated. The resultant residue was purified by column chromatography (silica gel:hexane/ethyl acetate=9/1) to obtain the object compound (197 mg, yield 100%).

$^1$H-NMR (300 MHz, CDCl$_3$) δ0.30 (6H, s), 1.09 (9H, s), 6.92 (1H, dd, J=7.8, 0.9 Hz), 7.38 (1H, dd, J=8.7, 4.5 Hz), 7.56 (1H, dd, J=8.4, 7.5 Hz), 7.73 (1H, dt, J=8.4, 0.9 Hz), 8.50 (1H, ddd, J=8.7, 2.1, 0.9 Hz), 8.89 (1H, dd, J=4.5, 1.8 Hz).

IR (liquid film method) 2934, 2862, 1593, 1574, 1470, 1396, 1365, 1317, 1261, 1201, 1164, 1141, 1087, 1056, 1019, 919, 833, 797 cm$^{-1}$ Mass (EI, m/e) 259 (M$^+$)

Reference Example 40

5-(t-butyldimethylsiloxy)-1,2,3,4-tetrahydroquinoline

5-(t-butyldimethylsiloxy)quinoline (1715 mg) was dissolved in ethanol (50 ml), and the air in a reactor was substituted by argon. 10% Pd—C (100 mg) was added to the resultant solution, and the mixture was stirred at room temperature in the reactor in which the atmosphere was replaced by hydrogen. After disappearance of the raw materials was confirmed, the solid was filtered off, and the filtrate was concentrated. The resultant residue was purified by column chromatography (silica gel:hexane/ethyl acetate= 10/1) to obtain the object compound (1426 mg, yield 82%).

¹H-NMR (300 MHz, CDCl₃) δ0.22 (6H, d, J=0.6 Hz), 1.00 (9H, d, J=0.6 Hz), 1.86–1.97 (2H, m), 2.65 (2H, t, J=6.6 Hz), 3.21–3.56 (2H, m), 3.80 (1H, br s), 6.13 (1H, d, J=8.1 Hz), 6.14 (1H, d, J=8.1 Hz), 6.82 (1H, td, J=7.8, 0.6 Hz).

IR (liquid film method) 2932, 2860, 1601, 1495, 1473, 1448, 1348, 1307, 1286, 1241, 1187, 1118, 1094, 1048, 1000, 934, 880, 841, 781 cm⁻¹

Mass (EI, m/e) 263 (M⁺)

Reference Example 41

Methyl 3-(2-hydroxyethyl)-2,3-dihydrobenzofuran-7-yloxyacetate

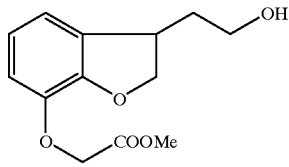

7-hydroxy-3-(2-hydroxyethyl)benzofuran (7.01 g) was dissolved in dimethylformamide (100 ml), and potassium carbonate (5.76 g) and methyl bromoacetate (4.74 ml) were added to the resultant solution, and the mixture was stirred at room temperature for 21 hours. The reaction solution was filtered with Celite, and the filtrate was concentrated. Ethyl acetate (300 ml) was added to the residue, and then the mixture was washed with water and saturated brine, and dried over sodium sulfate. After sodium sulfate was filtered off, the filtrate was concentrated, and the residue was dissolved in methanol (100 ml). 5% Pd/C (1.0 g), and acetic acid (5 ml) were added to the resultant solution, and the mixture was stirred at room temperature for 23 hours under a hydrogen atmosphere. The reaction solution was filtered with Celite, and the filtrate was concentrated. Ethyl acetate (300 ml) was added to the residue, and the mixture was washed with water and saturated brine, and dried over sodium sulfate. After sodium sulfate was filtered off, the filtrate was concentrated, and the residue was purified by flash column chromatography using silica gel (elution solvent:hexane/ethyl acetate=1/2) to obtain the object compound (7.80 g, yield 74%).

¹H-NMR (300 MHz, CDCl₃) δ1.37 (1H, t, J=4.9 Hz), 1.79–1.91 (1H, m), 2.11–2.00 (1H, m), 3.57–3.67 (1H, m), 3.77 (2H, dt, J=4.9, 6.3 Hz), 3.80 (3H, s), 4.34 (1H, dd, J=6.6, 8.8 Hz), 4.73 (2H, s), 4.74 (1H, t, J=8.8 Hz), 6.71–6.74 (1H, m), 6.80 (1H, t, J=8.0 Hz), 6.86–6.89 (1H, m).

Mass (EI, m/e) 252 (M⁺)

Reference Example 42

3-(2-hydroxyethyl)-2,3-dihydrobenzofuran-7-yloxyacetic acid

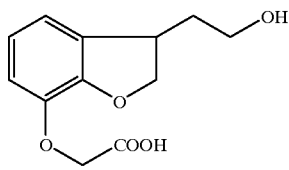

Methyl 3-(2-hydroxyethyl)-2,3-dihydrobenzofuran-7-yloxyacetate (7.80 g) was dissolved in methanol (100 ml), and a 2N sodium hydroxide aqueous solution (20 ml) was added to the resultant solution, and the mixture was stirred at room temperature for 4 hours. 1N hydrochloric acid (45 ml) was added to the reaction solution, and the mixture was concentrated. The residue was dissolved in ethyl acetate (200 ml), washed with water and saturated brine, and then dried over sodium sulfate. After sodium sulfate was filtered off, the filtrate was concentrated, and the residue was recrystallized from ethyl acetate/n-hexane to obtain the object compound (6.21 g, yield 84%).

mp. 91–93° C. (recrystallized from ethyl acetate/n-hexane)

¹H-NMR (300 MHz, CD₃OD) δ1.70–1.82 (1H, m), 1.94–2.05 (1H, m), 3.51–3.61 (1, m), 3.66 (2H, dt, J=2.5, 6.6 Hz), 4.28 (1H, dd, J=6.6, 8.8 Hz), 4.68 (1H, t, J=8.8 Hz), 4.69 (2H, s), 6.76–6.89 (3H, m).

Reference Example 43

(+)-3-(2-hydroxyethyl)-2,3-dihydrobenzofuran-7-yloxyacetic acid (−)-cis-2-benzylaminocyclohexanemethanol salt

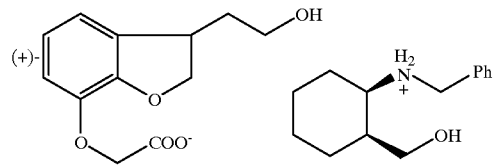

3-(2-hydroxyethyl)-2,3-dihydrobenzofuran-7-yloxyacetic acid (2.91 g) was dissolved in ethanol (30 ml), and (−)-cis-2-benzylaminocyclohexanemethanol (1.88 g) was added to the resultant solution, followed by reflux and dissolution. Ethyl acetate (15 ml) was then added to the resultant solution, and the mixture was cooled to room temperature to obtain crystals. The thus-obtained crystals were filtered off, and then recrystallized 6 times from ethanol to obtain the object compound of 97%e.e (0.77 g, yield 14%).

Reference Example 44

Methyl (+)-3-(2-hydroxyethyl)-2,3-dihydrobenzofuran-7-yloxyacetate

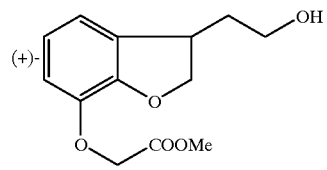

(+)-3-(2-hydroxyethyl)-2,3-dihydrobenzofuran-7-yloxyacetic acid (−)-cis-2-benzylaminocyclohexanemethanol salt (580 mg) was dissolved in water (30 ml), and the resultant solution was rendered acidic with 1N hydrochloric acid, and then extracted with ethyl acetate twice. The combined organic layers were washed with saturated brine, and dried over sodium sulfate. Sodium sulfate was filtered off, and the filtrate was concentrated. The residue was dissolved in 5 ml of methanol, and 2 drops of conc. hydrochloric acid were added to the resultant solution, followed by reflux for 30 minutes. After the reaction solution was cooled to room temperature, the solvent was distilled off under reduced pressure, and the residue was purified by flash column chromatography using silica gel (elution solvent:hexane/ethyl acetate=1/2) to obtain the object compound (274 mg, yield 86%). [α]$_D$ 28=+18.20 (c=0.455, CHCl$_3$)

Reference Example 45

5-(t-butyldimethylsiloxy)-1-chloroacetyl-1,2,3,4-tetrahydroquinoline

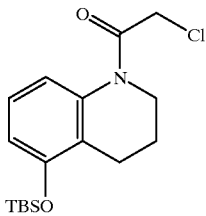

5-(t-butyldimethylsiloxy)-1,2,3,4-tetrahydroquinoline (1426 mg) was dissolved in methylene chloride (50 ml) under an argon atmosphere, and the resultant solution was stirred at 0° C. Pyridine (1.00 ml) and chloroacetyl chloride (0.70 ml) were added to the solution, and the mixture was stirred at 0° C. After disappearance of the raw materials was confirmed, the reaction solution was added to water (50 ml), and then extracted with ethyl acetate. The resultant organic layer was washed with saturated brine, dried over anhydrous sodium sulfate, and concentrated. The resultant residue was purified by column chromatography (silica gel:hexane/ethyl acetate=5/1) to obtain the object compound (1839 mg, yield 100%).

$^1$H-NMR (300 MHz, CDCl$_3$) δ0.24 (6H, s), 1.02 (9H, s), 1.98 (1H, quint, J=6.6 Hz), 2.70 (2H, t, J=6.6 Hz), 3.81 (2H, t, J=6.6 Hz), 4.25 (2H, s), 6.68 (1H, d, J=8.4 Hz), 6.75–7.00 (1H, m), 7.08 (1H, t, J=8.0 Hz).

IR (liquid film method) 2958, 2862, 1667, 1584, 1470, 1388, 1340, 1261, 1205, 1180, 1147, 1114, 1006, 942, 839, 828, 814, 783 cm$^{-1}$ Mass (EI, m/e) 339 (M$^{30}$)

Reference Example 46

1-((1,1-diphenylethylthio)acetyl)-5-hydroxy-1,2,3,4-tetrahydroquinoline

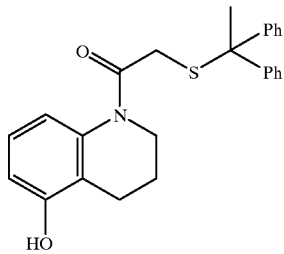

1,1-diphenylethanethiol (203 mg) was dissolved in DMF (3 ml) under an argon atmosphere, and the resultant solution was stirred at 0° C. Sodium hydride (65 mg) was added to the solution, and the mixture was stirred at 0° C. for 10 minutes. A solution of 5-(t-butyldimethylsiloxy)-1-chloroacetyl-1,2,3,4-tetrahydroquinoline (252 mg) in DMF (3 ml) was then added to the mixture, and the mixture was stirred at room temperature. After disappearance of the raw materials was confirmed, the reaction solution was added to water (30 ml), and then extracted with ethyl acetate. The resultant organic layer was washed with saturated brine, dried over anhydrous sodium sulfate, and concentrated. The resultant residue was purified by column chromatography (silica gel:hexane/ethyl acetate=2/1) to obtain the object compound (294 mg, yield 98%).

$^1$H-NMR (300 MHz, CDCl$_3$) δ1.88–1.98 (2H, m), 2.05 (3H, s), 0 2.65 (2H, t, J=7.1 Hz), 3.25 (2H, s), 3.50–3.80 (2H, m), 4.96 (1H, br s), 6.50–6.80 (1H, m), 6.60 (1H, d, J=8.7 Hz), 6.94 (1H, t, J=8.1 Hz), 7.14–7.40 (10H, m).

IR (KBr method) 2930, 1622, 1586, 1493, 1470, 1408, 1338, 1311, 1288, 1201; 1147, 1069, 915, 698 cm$^{-1}$ Mass (El, m/e) 403 (M$^{30}$)

Reference Example 47

1-(2-(1,1-diphenylethylthio)ethyl)-5-hydroxy-1,2,3,4-tetrahydroquinoline

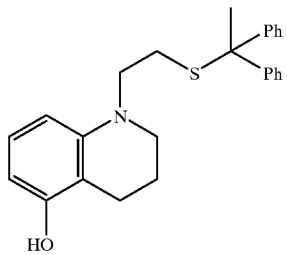

1-((1,1-diphenylethylthio)acetyl)-5-hydroxy-1,2,3,4-tetrahydroquinoline (136 mg) was dissolved in THF (5 ml), and the resultant solution was stirred at 0° C. A borane THF complex (1.0N in THF) (2.0 ml) was added to the solution, and the mixture was stirred at room temperature. After disappearance of the raw materials was confirmed, the reaction solution was added to a saturated ammonium chloride aqueous solution (20 ml), and then extracted with ethyl acetate. The resultant organic layer was washed with saturated brine, dried over anhydrous sodium sulfate, and a concentrated. The resultant residue was purified by column chromatography (silica gel:hexane/ethyl acetate=5/1) to obtain the object compound (60 mg, yield 46%).

$^1$H-NMR (300 MHz, CDCl$_3$) δ1.82–1.92 (2H, m), 2.07 (3H, s), 2.48–2.64 (4H, m), 3.04–3.19 (4H, m), 4.54 (1H, br s), 5.83 (1H d, J=8.1 Hz), 6.07 (1H, dd, J=8.1, 0.9 Hz), 6.81 (1H, t, J=8.1 Hz), 7.20–7.35 (6H, m), 7.39–7.45 (4H, m).

IR (liquid film method) 2934, 1615, 1578, 1506, 1481, 1464, 1446, 1332, 1270, 1224, 1195, 1152, 1102, 1029, 913, 762, 700 cm$^{-1}$ Mass (EI, m/e) 389 (M$^+$)

Example 1

Methyl (4-(2-(diphenylmethylthio)ethyl)-3,4-dihydro-2H-1,4-benzoxazin-8-yloxy)acetate

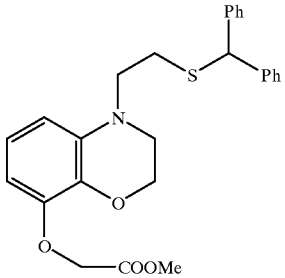

Methyl (4-(2-hydroxyethyl)-3,4-dihydro-2H-1,4-benzoxazin-8-yloxy)acetate (347 mg) was dissolved in methylene chloride (8.0 ml), and triethylamine (0.60 ml) was added to the resultant solution and then cooled to 0° C. Methanesulfonyl chloride (0.08 ml) was added to the mixture, and the mixture was stirred at 0° C. for 40 minutes. Methanesulfonyl chloride (0.10 ml) was further added to the mixture, and the mixture was stirred at 0° C. for 1 hour. The reaction solution was poured into a 5% citric acid aqueous solution, and then extracted with ethyl acetate. The resultant organic layer was washed with water, saturated sodium bicarbonate water, water and saturated brine, dried over magnesium sulfate, and then concentrated to obtain a mesyl compound.

Sodium hydride (68 mg) was washed with n-hexane, dried under reduced pressure, and then the air was substituted by argon. A solution of diphenylmethanethiol (440 mg) in anhydrous DMF (3.5 ml) was added to the sodium hydride at 0° C., and the mixture was stirred at room temperature for 10 minutes. A solution of the above mesyl compound in anhydrous DMF (6.0 ml) was added to the mixture, and the mixture was stirred at room temperature for 3 hours. The solvent was distilled off under reduced pressure, and the residue was poured into a 5% citric acid aqueous solution, and then extracted with ethyl acetate. The resultant organic layer was washed with water and saturated brine, dried over magnesium sulfate, and concentrated. The resultant residue was purified by column chromatography (neutral alumina:methyl acetate/n-hexane=1:3) to obtain the object compound (476 mg, yield 81%). Colorless plate crystal: mp. 94–95° C. (recrystallized from ethyl acetate/n-hexane)

$^1$H-NMR (300 MHz, CDCl$_3$) δ2.61 (2H, m), 3.26 (2H, m), 3.36 (2H, m), 3.78 (3H, s), 4.24 (2H, m), 4.65 (2H, s), 5.24 (1H, s), 6.06 (1H, dd, J=1, 8 Hz), 6.20 (1H, dd, J=l, 8 Hz), 6.61 (1H, t, J=8 Hz), 7.26–7.31 (6H, m), 7.41–7.46 (4H, m).

IR (KBr method) 2954, 1763, 1611, 1489, 1452, 1350, 1245, 1212, 1180, 1164, 1129, 1079, 1048, 752, 704 cm$^{-1}$ Mass (EI, m/e) 449 (M$^+$)

Example 2

Methyl (4-(2-(1,1-diphenylethylthio)ethyl)-3,4-dihydro-2H-1,4-benzoxazin-8-yloxy)acetate

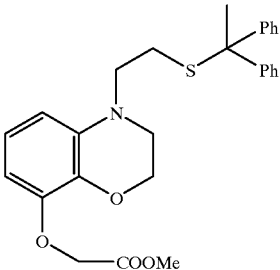

The same process as Example 1 was repeated except that methyl (4-(2-hydroxyethyl)-3,4-dihydro-2H-1,4-benzoxazin-8-yloxy)acetate (1.27 g) and 1,1-diphenylethanethiol-(1.13 g) were used to obtain the object compound (1.78 g, yield 81%). Colorless columnar crystal: mp. 101° C. (recrystallized from ethyl acetate/n-hexane)

$^1$H-NMR (300 MHz, CDCl$_3$) δ2.06 (3H, s), 2.51 (2H, t, J=8 Hz), 3.13 (2H, t, J=8 Hz), 3.19 (2H, t, J=4.5 Hz), 3.78 (3H, s), 4.22 (2H, t, J=4.5 Hz), 4.65 (2H, s), 6.01 (1H, dd, J=1, 8 Hz), 6.19 (1H, dd, J=1, 8 Hz), 6.62 (1H, t, J=8 Hz), 7.21–7.44 (10H, m).

IR (KBr method) 3034, 2930, 2875, 1765, 1611, 1580, 1487, 1444, 1350, 1286, 1245, 1212, 1180, 1164, 1129, 760, 700, 681 cm$^{-1}$ Mass (EI, m/e) 463(M$^+$)

Example 3

Methyl (4-(2-(1,1-diphenyl-2,2,2-trifluoroethylthio)ethyl)-3,4-dihydro-2H-1,4-benzoxazin-8-yloxy)acetate

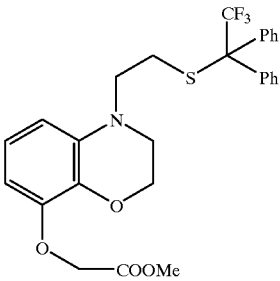

The same process as Example 1 was repeated except that methyl (4-(2-hydroxyethyl)-3,4-dihydro-2H-1,4-benzoxazin-8-yloxy)acetate (375 mg) and 1,1-diphenyl-2,2,2-trifluoroethanethiol (385 mg). were used to obtain the object compound (614 mg, yield 85%).

Pale yellow oily substance $^1$H-NMR (300 MHz, CDCl$_3$) δ2.55 (2H, t, J=7 Hz), 3.17 (4H, m), 3.78 (3H, s), 4.21 (2H, , 4.64 (2H, s), 5.94 (1H, dd, J=1, 8 Hz), 6.19 (1H, dd, J=1, 8 Hz), 6.60 (1H, t, J=8 Hz), 7.31–7.36 (6H, m), 7.42–7.46 (4H, m).

IR (liquid film method) 2934, 1765, 1611, 1580, 1487, 1448, 1350, 1251, 1212, 1160, 754, 719, 700 cm$^{-1}$ Mass (EI, m/e) 517 (M$^+$)

Example 4

Methyl (4-(2-(1,1-bis-(4-fluorophenyl)ethylthio)ethyl)-3,4-dihydro-2H-1,4-benzoxazin-8-yloxy)acetate

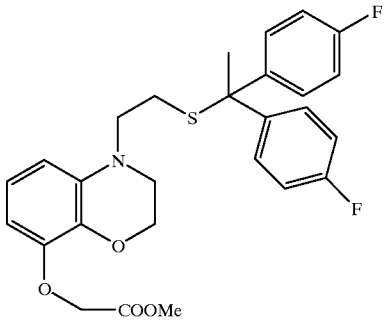

The same process as Example 1 was repeated except that methyl (4-(2-hydroxyethyl)-3,4-dihydro-2H-1,4-benzoxazin-8-yloxy)acetate (200 mg) and 1,1-bis-(4-fluorophenyl)ethanethiol (450 mg) were used to obtain the colorless oily object compound (311 mg, yield 83%).

$^1$H-NMR (300 MHz, CDCl$_3$) δ2.02 (3H, s), 2.50 (2H, t, J=7.6 Hz), 3.21–3.35 (6H, m), 3.79 (3H, s), 4.24 (2H, t, J=4.4 Hz), 4.66 (2H, s), 6.22 (1H, d, J=8.5 Hz), 6.27 (1H, d, J=8.5 Hz), 6.70 (1H, t, J=8.5 Hz), 7.17–7.32 (10H, m).

IR (liquid film method) 2956, 2932, 1763, 1605, 1578, 1487, 1460, 1439, 1377, .1350, 1328, 1288, 1214, 1162, 1133, 1077, 1062, 1013 cm$^{-1}$ Mass (EI, m/e) 499 (M$^+$)

Example 5

Methyl (4-(2-1-methyl-1-phenylethylthio)ethyl)-3,4-dihydro-2H-1,4-benzoxazin-8-yloxy)acetate

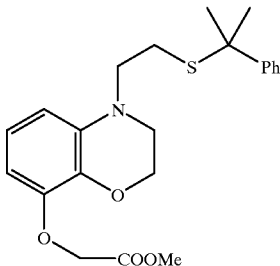

The same process as Example 1 was repeated except that methyl (4-(2-hydroxyethyl)-3,4-dihydro-2H-1,4-benzoxazin-8-yloxy)acetate (343 mg) and 2-phenylpropane-2-thiol (404 mg) were used to obtain the object compound (483 mg, yield 94%).

Pale yellow oily substance $^1$H-NMR (300 MHz, CDCl$_3$) δ1.72 (6H, s), 2.42 (2H, t, J=8 Hz), 3.09 (2H, t, J=8 Hz), 3.17 (2H, t, J=4.5 Hz), 3.78 (3H, s), 4.20 (2H, t, J=4.5 Hz), 4.64 (2H, s), 5.94(1H, dd, J=1, 8 Hz), 6.17 (1H, dd, J=1, 8 Hz), 6.60 (1H, t, J=8 Hz), 7.24 (1H, m), 7.34 (2H, m), 7.54 (2H, m).

IR (liquid film method) 2970, 2928, 2874, 1765, 1611, 1497, 1487, 1448, 1348, 1286, 1245, 1212, 1180, 1164, 1129, 1100, 1077, 768, 700 cm$^{-1}$ Mass (EI, m/e) 401 (M$^{30}$)

Example 6

Methyl (4-(2-(2,2-diphenylpropylthio)ethyl)-3,4-dihydro-2H-1,4-benzoxazin-8-yloxy)acetate

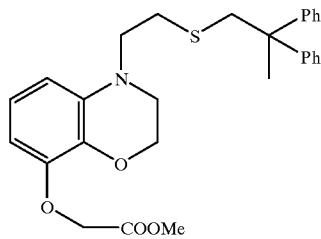

The same process as Example 1 was repeated except that methyl (4-(2-hydroxyethyl)-3,4-dihydro-2H-1,4-benzoxazin-8-yloxy)acetate (200 mg) and 2,2-diphenylpropanethiol (410 mg) were used to obtain the colorless oily object compound (134 mg, yield 37%).

$^1$H-NMR (300 MHz, CDCl$_3$) δ1.78 (3H, s), 2.36 (2H, t, J=7.6 Hz), 3.24–3.35 (6H, m), 3.79 (3H, s), 4.24 (2H, t, J=4.4 Hz), 4.66 (2H, s), 6.22(1H, d, J=8.5 Hz), 6.27 (1H, d, J=8.5 Hz), 6.70 (1H, t, J=8.5 Hz), 7.17–7.32 (10H, m).

IR (liquid film method) 3058, 2928, 2880, 1765, 1736, 1609, 1578, 1489, 1446, 1375 cm$^{-1}$ Mass (EI, m/e) 477 (M$^+$)

Example 7

Methyl (4-(2-(1,1-bis-(3-thienyl)ethylthio)ethyl-3,4-dihydro-2H-1,4-benzoxazin-8-yloxy)acetate

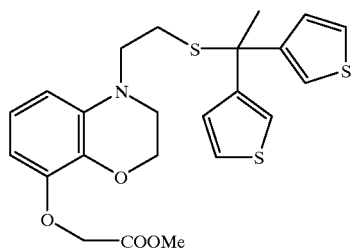

The same process as Example 1 was repeated except that methyl (4-(2-hydroxyethyl)-3,4-dihydro-2H-1,4-benzoxazin-8-yloxy)acetate (150 mg) and 1,1-bis-(3-thienyl)ethanethiol (320 mg) were used to obtain the colorless oily object compound (253 mg, yield 95%).

$^1$H-NMR (300 MHz, CDCl$_3$) δ2.05 (3H, s), 2.51–2.58 (2H, m), 3.16 (2H, t, J=7.7 Hz), 3.23 (2H, t, J=4.4 Hz), 3.79 (3H, s), 4.23 (2H, t, J=4.4 Hz), 4.65 (2H, s), 6.07(1H, dd, J=8.2, 1.1 Hz), 6.20 (1H, dd, J=8.2, 1.1 Hz), 6.66 (1H, t, J=8.2 Hz), 7.11 (2H, dd, J=3.0, 1.4 Hz), 7.14 (2H, dd, J=5.2, 1.4 Hz), 7.29 (2H, dd, J=5.2, 3.0 Hz).

IR (liquid film method) 3108, 2954, 2930, 2878, 1767, 1740, 1615, 1580, 1506, 1456, 1375, 1350, 1330, 1288, 1247, 1212, 1164, 1131, 1079, 1050, 1004, 928, 777 cm$^{-1}$ Mass (EI, m/e) 475 (M$^+$)

Example 8

Methyl (4-(2-(diphenylmethoxy)ethyl)-3,4-dihydro-2H-1,4-benzoxazin-8-yloxy)acetate

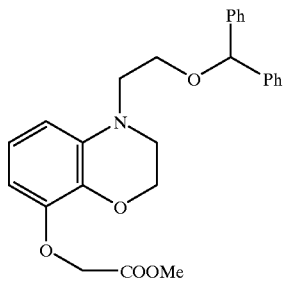

4-(2-(diphenylmethoxy)-ethyl)-8-hydroxy-3,4-dihydro-2H-1,4-benzoxazine (161 mg) was dissolved in anhydrous DMF (4 ml), and anhydrous potassium carbonate (54 mg) and methyl bromoacetate (0.04 ml) were added to the resultant solution, and the mixture was stirred at room temperature overnight. The reaction solution was poured into a saturated ammonium chloride aqueous solution, and then extracted with ethyl acetate containing 15% n-hexane. The resultant organic layer was washed with water and saturated brine, dried over sodium sulfate, and concentrated. The resultant residue was purified by medium-pressure column chromatography (solvent:ethyl acetate:cyclohexane=1/3) to obtain the colorless oily object compound (118 mg, yield 97%).

$^1$H-NMR (300 MHz, CDCl$_3$) δ3.46 (2H, t, J=4.4 Hz), 3.53 (2H, t, J=5.6 Hz), 3.65 (2H, t, J=5.6 Hz), 3.79 (3H, s), 4.26 (2H, t, J=4.4 Hz), 4.68 (2H, s), 5.34 (1H, s), 6.21 (1H, dd, J=8.2, 1.4 Hz), 6.36 (1H, dd, J=8.2, 1.4 Hz), 6.68 (1H, t, J=8.2 Hz), 7.19–7.32 (10H, m).

IR (liquid film method) 3064, 3030, 2954, 2870, 1763, 1736, 1611, 1578, 1489, 1456, 1350, 1330, 1284, 1212, 1187, 1151, 1093 cm$^{-1}$ Mass (EI, m/e) 433 (M$^+$)

Example 9

Methyl (4-(2-(1,1-diphenylethoxy)ethyl)-3,4-dihydro-2H-1,4-benzoxazin-8-yloxy)acetate

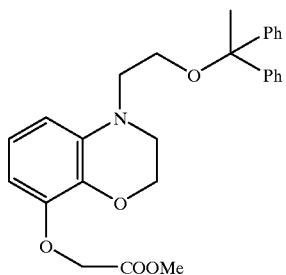

The same process as Example 8 was repeated except that 4-(2-(1,1-diphenylethoxy)ethyl)-8-hydroxy-3,4-dihydro-2H-1,4-benzoxazine (239 mg) was used to obtain the colorless oily object compound (229 mg, yield 80%).

$^1$H-NMR (300 MHz, CDCl$_3$) δ1.83 (3H, s), 3.40–3.51 (6H, m), 3.79 (3H, s), 4.27 (2H, t, J=4.4 Hz), 4.67 (2H, s), 6.19(1H, dd, J=8.2, 1.1 Hz), 6.27 (1H, dd, J=8.2, 1.1 Hz), 6.64 (1H, t, J=8.2 Hz), 7.17–7.34 (10H, m).

IR (liquid film method) 2980, 2954, 2874, 1763, 1743, 1613, 1578, 1489, 1448, 1350, 1212, 1093 cm$^{-1}$ Mass (EI, m/e) 447 (M$^+$)

Example 10

Methyl (4-(4,4-diphenylpentyl)-8-hydroxy-3-oxo-3,4-dihydro-2H-1,4-benzoxazin-8-yloxy)acetate

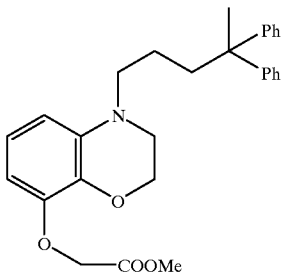

4-(4,4-diphenylpentyl)-8-hydroxy-3-oxo-3,4-dihydro-2H-1,4-benzoxazine was dissolved in anhydrous DMF (15 ml), and anhydrous potassium carbonate (180 mg) and methyl bromoacetate (0.15 ml) were added to the resultant solution, and the mixture was stirred at room temperature overnight. The reaction solution was poured into a saturated ammonium chloride aqueous solution, and then extracted with ethyl acetate containing 15% n-hexane. The resultant organic layer was washed with water and saturated brine, dried over sodium sulfate, and concentrated. The resultant residue was purified by medium-pressure column chromatography (solvent:ethyl acetate/cyclohexane=1/3) to obtain the colorless oily object compound (386 mg, yield 92%).

$^1$H-NMR (300 MHz, CDCl$_3$) δ1.35–1.47 (2H, m), 1.63 (3H, s), 2.08–2.16 (2H, m), 3.15 (2H, t, J=7.4 Hz), 3.19 (2H, t, J=4.4 Hz), 3.79 (3H, s), 4.24 (2H, t, J=4.4 Hz), 4.66 (2H, s), 6.19 (1H, dd, J=8.2, 1.4 Hz), 6.24 (1H, dd, J=8.2, 1.4 Hz), 6.66 (1H, t, J=8.2 Hz), 7.14–7.21 (6H, m), 7.23–7.30 (4H, m).

IR (liquid film method) 3060, 3030, 2954, 2876, 1763, 1740, 1613, 1578, 1485, 1460, 1444, 1375, 1350, 1328, 1288, 1245, 1210, 1174, 1135, 1108, 911 cm$^{-1}$ Mass (EI, m/e) 445 (M$^{30}$)

Example 11

Methyl (4-(2-(1,1-diphenylethylthio)ethyl)-3-oxo-3,4-dihydro-2H-1,4-benzoxazin-8-yloxy)acetate

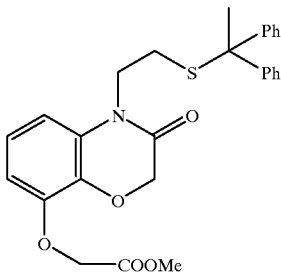

The same process as Example 1 was repeated except that methyl (4-(2-hydroxyethyl)-3-oxo-3,4-dihydro-2H-1,4-benzoxazin-8-yloxy)acetate (187 mg) and 1,1-diphenylethanethiol (270 ml) were used to obtain the object compound (172.5 mg, yield 42%).

Colorless oily substance $^1$H-NMR (300 MHz, CDCl$_3$) δ2.08 (3H, s), 2.57 (2H, m), 3.79 (3H, s), 3.81 (2H, m), 4.59 (2H, s), 4.69 (2H, s), 6.13(1H, dd, J=1, 8 Hz), 6.56 (1H, dd, J=1, 8 Hz), 6.81 (1H, t, J=8 Hz), 7.21–7.34 (6H, m), 7.40–7.45 (4H, m).

IR (liquid film method) 2920, 2332, 1763, 1686, 1611, 1485, 1444, 1402, 1317, 1282, 1214, 1195, 1151, 1058, 766, 733, 698, 667 cm$^{-1}$ Mass (EI, m/e) 477 (M$^+$)

Example 12

Methyl (4-((diphenylmethylcarbamoyl)methyl)-3-oxo-3,4-dihydro-2H-1,4-benzoxazin-8-yloxy)acetate

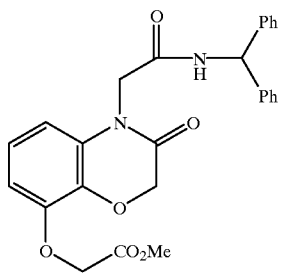

N-diphenylmethyl-2-(8-hydroxy-3-oxo-3,4-dihydro-2H-1,4-benzoxazin-4-yl)acetamide (735 mg) was dissolved in DMF (30 ml), and the resultant solution was stirred at room temperature. Potassium carbonate (785 mg) and methyl bromoacetate (0.35 ml) were added to the solution, and the mixture was stirred at room temperature for 18 hours. Water (25 ml) was added to the reaction solution, and the mixture was then extracted with ethyl acetate. The resultant organic layer was washed with saturated saline, dried over sodium sulfate, and concentrated. The resultant residue was recrystallized from ethyl acetate/n-hexane to obtain the object compound (492 mg, yield 56%)

mp. 183.0–184.0° C.

$^1$H-NMR (300 MHz, CDCl$_3$) δ3.80 (3H, s), 4.60 (2H, s), 4.72 (4H, s), 6.21 (1H, d, J=6.0 Hz), 6.65 (1H, dd, J=1.5, 8.1 Hz), 6.82 (1H, d, J=7.5 Hz), 6.87 (1H, dd; J=1.5, 8 Hz), 6.95 (1H, t, J=8.3 Hz), 7.10–7.17 (4H, m), 7.20–7.33 (6H, m).

IR (KBr method) 3301, 1752, 1693, 1662, 1612, 1541, 1484, 1401, 1282, 1228, 1192, 1161, 1106, 1056, 862, 767, 700 cm$^{-1}$ Mass (EI, m/e) 460 (M$^+$)

Example 13

Methyl 3-(4-(2-(1,1-diphenylethylthio)ethyl)-3-oxo-3,4-dihydro-2H-1,4-benzoxazin-8-yl)propionate

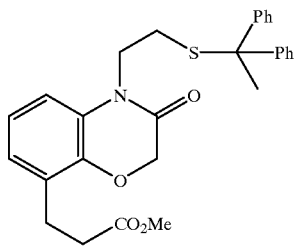

Methyl 3-(4-(2-hydroxyethyl)-3-oxo-3,4-dihydro-2H-1,4-benzoxazin-8-yl)propionate (300 mg) was dissolved in dichloromethane (5 ml), and triethylamine (0.3 ml) was added to the resultant solution, and cooled to 0° C. Methanesulfonyl chloride (0.1 ml) was stirred into the mixture at 0° C. for 1 hour. The reaction solution was poured into a %5 citric acid aqueous solution, and then extracted with ethyl acetate. The resultant organic layer was dried over magnesium sulfate and concentrated to obtain a mesyl compound. Sodium hydride (58 mg) was suspended in anhydrous DMF (3 ml), and a solution of 1,1-diphenylethanethiol (319 mg) in anhydrous DMF (4 ml) was added to the suspension at 0° C., followed by stirring at room temperature for 1 hour. A solution of the above mesyl compound in anhydrous DMF (4 ml) was added to the resultant mixture, and the mixture was stirred at room temperature for 2 hours. The solvent was distilled off under reduced pressure, and the residue was poured into a 5% citric acid aqueous solution, and then extracted with ethyl acetate. The resultant organic layer was dried over magnesium sulfate and then concentrated. The resultant residue was purified by column chromatography (silica gel:hexane/ethyl acetate=2/1) to obtain the object compound (254 mg, yield 50%).

$^1$H-NMR (300 MHz, CDCl$_3$) δ2.08 (3H, s), 2.55–2.61 (4H, m), 2.92 (2H, t, J=7.8 Hz), 3.66 (3H, s), 3.81 (2H, t, J=8.1 Hz), 4.52 (2H, s), 6.31 (1H, dd, J=2.1, 7.5 Hz), 6.79–6.87 (2H, m), 7.22–7.34 (6H, m), 7.42–7.45 (4H, m).

IR (liquid film method) 3586, 3056, 2980, 2951, 1890, 1737, 1685, 1609, 1591, 1481, 1442, 1400, 1372, 1315, 1242, 1172, 1125, 1092, 1045, 931, 823, 763, 742, 701, 661 cm$^{-1}$ Mass (EI, m/e) 475 (M$^+$)

Example 14

Methyl (4-(3-(2-naphthylmethylamino)propyl)-3,4-dihydro-2H-1,4-benzoxazin-8-yloxy)acetate

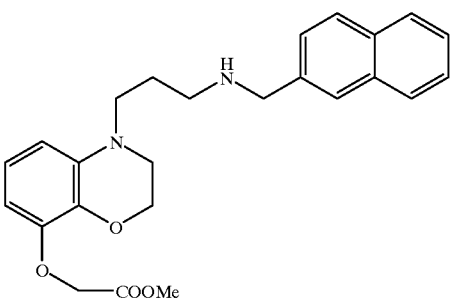

(4-(3-(2-naphthylmethylamino)propyl)-8-hydroxy-3,4-dihydro-2H-1,4-benzoxazine (166 mg) was dissolved in DMF (3 ml), and potassium carbonate (63 mg) and methyl bromoacetate (0.045 ml) were added. to the resultant solution at 0° C., followed by stirring at room temperature for 16 hours. The reaction solution was diluted with ethyl acetate, washed with saturated brine, and dried over anhydrous sodium sulfate. The solvent was then distilled off under reduced pressure, and the residue was purified by column chromatography (silica gel:ethyl acetate/n-hexane=2:3) to obtain the object compound (140 mg, yield 73%).

Colorless oily substance $^1$H-NMR (300 MHz, CDCl$_3$) δ1.76–1.92 (1H, m), 2.13–2.30 (1H, m), 2.71–2.83 (1H, m), 2.86–2.98 (1H, m), 3.00–3.22 (3H, m), 3.28 (1H, ddd, J=12.1, 4.9. 2.7 Hz), 3.71 (1H, dd, J=13.7, 9.3 Hz), 3.81 (3H, s), 4.04–4.23 (2H, m), 4.35 (1H, dd, J=13.7, 3.0 Hz), 4.46 (1H, br. s), 4.68 (2H, s), 6.12 (1H, dd, J=8.2, 1.1 Hz), 6.28 (1H, dd, J=8.2, 1.4 Hz), 6.54 (1H, t, J=8.2 Hz), 7.22 (1H, dd, J=8.4, 1.8 Hz), 7.48–7.84 (2H, m), 7.64 (1H, br. s), 7.69–7.78 (2H, m), 7.81–7.88 (1H, m).

IR (liquid film method) 3217, 2951, 2879, 1757, 1611, 1578, 1484, 1348, 1327, 1210, 1174, 1108, 910, 859, 822, 755, 730, 646 cm$^{-1}$ Mass (EI, m/e) 420 (M$^+$)

Example 15

Methyl (1-(2-(1,1-diphenylethylthio)ethyl)-1,2,3,4-tetrahydroquinolin-5-yloxy)acetate

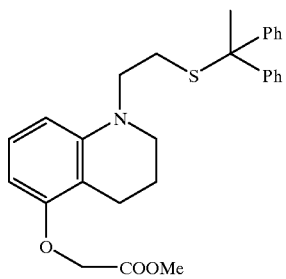

The same process as Example 8 was repeated except that 1-(2-(1,1-diphenylethylthio)ethyl)-5-hydroxy-1,2,3,4-tetrahydroquinoline (60 mg) was used to obtain the object compound (51 mg, yield 72%).

$^1$H-NMR (300 MHz, CDCl$_3$) δ1.78–1.89 (2H, m), 2.06 (3H, s), 2.47–2.55 (2H, m), 2.69 (2H, t, J=6.6 Hz), 3.04–3.18 (4H, m), 3.78 (3H, s), 4.56 (2H, s), 5.91 (1H, d, J=8.4 Hz), 6.02(1H, d, J=8.4 Hz), 6.86 (1H, t, J=1, 8.4 Hz), 7.20–7.35 (6H, m), 7.38–7.47 (4H, m).

IR (liquid film method) 2930, 1763, 1605, 1578, 1493, 1464, 1444, 1336, 1286, 1195, 1160, 1123, 1064, 1029, 760, 702 cm$^{-1}$ Mass (EI, m/e) 461 (M$^+$)

Example 16

Methyl (1-(2-(1,1-diphenylethylthio)ethyl)-2,3,4,5-tetrahydro-1H-1-benzazepin-6-yloxy)acetate

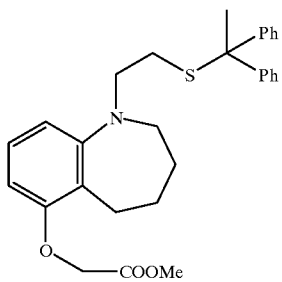

Methyl (1-(2-hydroxyethyl)-2,3,4,5-tetrahydro-1H-1-benzazepin-6-yloxy)acetate (370 mg) was dissolved in methylene chloride (15 ml), and the resultant solution was stirred at 0° C. Triphenylphosphine (1085 mg) and carbon tetrabromide (922 mg) were added to the solution, and the mixture was stirred at 0° C. After disappearance of the raw materials was confirmed, a saturated sodium bicarbonate aqueous solution (15 ml) was added to the reaction solution, and the mixture was then extracted with ethyl acetate. The resultant organic layer was washed with saturated brine, dried over anhydrous sodium sulfate and concentrated. The resultant residue was purified by column chromatography (silica gel:hexane/ethyl acetate=1/1) to obtain a crude product. 1,1-diphenylethanethiol (428 mg) was dissolved in DMF (10 ml) under an argon atmosphere, and the resultant solution was stirred at 0° C. Sodium hydride (65 mg) was added to the solution, and the mixture was stirred at 0° C. for 5 minutes. A solution of the crude product in DMF (3 ml) was added to the mixture at 0° C. After disappearance of the raw materials was confirmed, the reaction solution was added to a saturated ammonium chloride aqueous solution (30 ml), and then extracted with ethyl acetate. The resultant organic layer was washed with saturated brine, dried over anhydrous sodium sulfate and concentrated. The resultant residue was purified by column chromatography (silica gel:hexane/ethyl acetate=8/1) to obtain the object compound (532 mg, yield 84%).

$^1$H-NMR (300 MHz, CDCl$_3$) δ1.50–1.68 (4H, m), 2.05 (3H, s), 2.45–2.53 (2H, m), 2.78–2.95 (4H, m), 3.00–3.15 (2H, m), 3.78 (3H, s), 4.59 (2H, s), 6.35 (2H, d, J=8.1 Hz), 6.95(1H, t, J=8.1 Hz), 7.17–7.36 (6H, m), 7.38–7.44 (4H, m).

IR (liquid film method) 2926, 1765, 1599, 1466, 1444, 1210, 1141, 1114, 731, 698 cm$^{-1}$ Mass (EI, m/e) 475 (M$^+$)

Example 17

Methyl (3-(2-(diphenylmethylthio)ethyl)-2,3-dihydrobenzofuran-7-yloxy)acetate

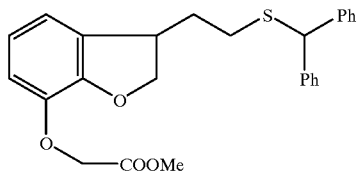

Methyl (3-(2-(methanesulfonyloxy)ethyl)benzofuran-7-yloxy)acetate (161 mg) was dissolved in ethyl acetate (3 ml), and 5% Pd/C (34 mg) and acetic acid (84 μl) were added to the resultant solution, and the mixture was stirred at room temperature under a hydrogen atmosphere for 13.5 hours. The reaction solution was filtered with Celite, and the filtrate was concentrated under reduced pressure.

Diphenylmethanethiol (128 mg) was dissolved in DMF (2 ml), and t-BuOK (66 mg) was added to the resultant solution, and the mixture was stirred at room temperature for 5 minutes. A solution of the reaction residue in DMF (1.5 ml) was added to the above solution at room temperature for 10 minutes. The reaction solution was poured into a water layer, and then extracted with ethyl acetate twice. The combined organic layers were washed with saturated brine, dried over sodium sulfate, and concentrated under reduced pressure. The resultant residue was purified by column chromatography (silica gel:n-hexane/ethyl acetate=3/1) to obtain the object compound (176 mg, yield 83%).

¹H-NMR (300 MHz, CDCl₃) δ1.87–1.76 (1H, m), 2.03–1.91 (1H, m), 2.48–2.42 (2H, m), 3.56–3.45 (1H, m), 3.79 (3H, s), 4.59 (1H, t, J=8.8 Hz), 4.13 (1H, dd, J=8.8, 6.0 Hz), 4.87 (2H, s), 5.15 (1H, s), 6.91–6.69 (3H, m), 7.61–7.20 (10H, m).

IR (KBr method) 3062, 3030, 2954, 1856, 1769, 1622, 1599, 1491, 1454, 1377, 1296, 1189, 1114, 1079, 1031, 1002, 953, 911, 830, 752, 704 cm⁻¹

Mass (EI, m/e) 434 (M⁺)

Example 18

Methyl(3-(2-(1,1-diphenylethylthio)ethyl)-2,3-dihydrobenzofuran-7-yloxy)acetate

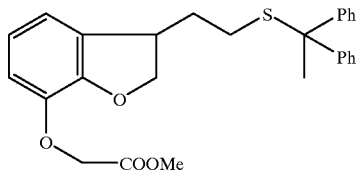

The same process as Example 17 was repeated except that methyl (3-(2-(methanesulfonyloxy)ethyl)benzofuran-7-yloxy)acetate (284 mg) and 1,1-diphenylethanethiol (240 mg) were used to obtain the object compound (310 mg, yield 95%).

¹H-NMR (300 MHz, CDCl₃) δ1.86–1.59 (2H, m), 2.06 (3H, s), 2.41–2.26 (2H, m), 3.50–3.42 (1H, m), 3.78 (3H, s), 4.07 (1H, dd, J=8.8, 6.0 Hz), 4.51 (1H, t, J=8.8 Hz), 4.69 (2H, s), 6.76–6.63 (3H, m), 7.44–7.22 (10H, m).

IR (liquid film method) 3060, 3032, 2956, 2932, 1765, 1742, 1622, 1595, 1491, 1458, 1444, 1377, 1294, 1216,, 1191, 1114, 1029, 953, 830, 764, 743, 700 cm⁻¹

Mass (EI, m/e) 448 (M⁺)

Example 19

Methyl (+)-3-(2-(3-(2hydroxyphenyl)propylthio)ethyl)-2,3-dihydrobenzofuran-7-yloxyacetate

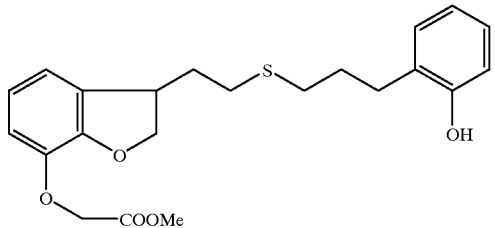

(+)-3-(2-hydroxyethyl)-2,3-dihydrobenzofuran-7-yloxyacetic acid (180 mg) was dissolved in dichloromethane (3 ml), and cooled to 0° C. Triethylamine (0.072 ml) and methanesulfonyl chloride (0.15 ml) were added to the resultant solution, and the mixture was stirred at 0° C. for 30 minutes. The reaction solution was poured into water, and then extracted with ethyl acetate twice. The combined organic layers were washed with saturated brine, and dried over sodium sulfate. Sodium sulfate was filtered off, and the filtrate was concentrated.

3-(2-methoxymethoxyphenyl)propanethiol (197 mg) was dissolved in dimethylformamide (5 ml), and potassium t-butoxide (96 mg) was added to the resultant solution, and the mixture was stirred at room temperature for 10 minutes. A solution of the previously prepared mesylate in dimethylformamide (2 ml) was added to the reaction solution, and the mixture was stirred at room temperature for 50 minutes. The reaction solution was poured into water, and the extracted with ethyl acetate twice. The combined organic layers were washed with saturated brine, and dried over sodium sulfate. Sodium sulfate was filtered off, and the filtrate was concentrated. The residue was dissolved in methanol (5 ml), and a 2N HCl/methanol solution (0.5 ml) was added to the resultant solution, and the mixture was stirred at room temperature for 19 hours. The reaction solution was concentrated, and the residue was purified by flash column chromatography using silica gel (elution solvent:hexane/ethyl acetate=2/1) to obtain the object compound (168 mg, yield 64%).

¹H-NMR (300 MHz, CDCl₃) δ1.80–2.07 (4H, m), 2.51–2.60 (4H, m), 2.73 (2H, t, J=7.1 Hz), 3.54–3.63 (1H, m), 3.80 (3H, s), 4.30 (1H, dd, J=5.8, 9.1 Hz), 4.69 (1H, t, J=9.1 Hz), 4.73 (2H, s), 5.42 (1H, s), 6.71–6.89 (5H, m), 7.12–7.06 (2H, m).

IR (KBr method) 3433, 2949, 1744, 1592, 1488, 1456, 1232, 1187, 1114, 755 cm⁻¹

Mass (EI, m/e) 402 (M⁺)

Example 20

(4-(2-(diphenylmethylthio)ethyl)-3,4-dihydro-2H-1,4-benzoxazin-8-yloxy)acetic acid

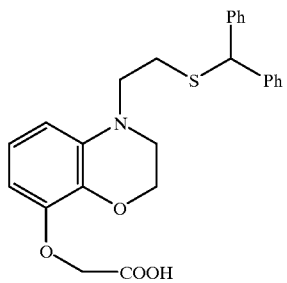

Methyl (4(2-(diphenylmethylthio)ethyl)-3,4-dihydro-2H-1,4-benzoxazin-8-yloxy)acetate (439 mg) was dissolved in methanol (8.0 ml), and a 4.89N sodium hydroxide aqueous solution (0.60 ml) was added to the resultant solution, and the mixture was stirred at room temperature for 2 hours. The solvent was distilled off under reduced pressure, and the residue was poured into a 5% citric acid aqueous solution, and then extracted with ethyl acetate. The resultant organic layer was washed with water and saturated brine, dried over magnesium sulfate, and then concentrated. The residue was recrystallized from ethyl acetate/n-hexane to obtain the object compound (381 mg, yield 90%).

Colorless needle crystal: mp. 172.5° C. (recrystallized from ethyl acetate/n-hexane)

¹H-NMR (300 MHz, CDCl₃) δ2.60 (2H, m), 3.27 (2H, t, J=4 Hz), 3.37 (2H, m), 4.24 (2H, t, J=4 Hz), 4.61 (2H, s), 5.23 (1H, s), 6.10 (1H, dd, J=1, 8 Hz), 6.31 (1H, dd, J=1, 8 Hz), 6.66 (1H, t, J=8 Hz), 7.22–7.37 (6H, m), 7.42–7.46 (4H, m).

IR (KBr method) 3030, 2989, 2590, 1743, 1610, 1576, 1487, 1451, 1431, 1348, 1259, 1240, 1214, 1186, 1160, 1131, 1102, 1081, 1048, 752, 703 cm⁻¹

Mass (EI, m/e) 435 (M⁻¹⁾

| Elemental analysis | | | | |
|---|---|---|---|---|
| Calcd | C: 68.94% | H: 5.79% | N: 3.22% | S: 7.36% |
| Found | C: 68.85% | H: 5.77% | N: 3.24% | S: 7.25% |

Example 21

(4-(2-(1,1-diphenylethylthio)ethyl)-3,4-dihydro-2H-1,4-benzoxazin-8-yloxy)acetic acid

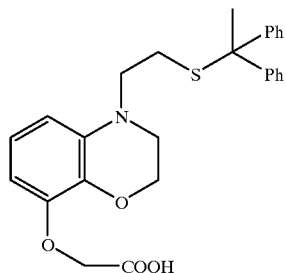

The same process as Example 20 was repeated except that methyl (4-(2-(1,1-diphenylethylthio)ethyl)-3,4-dihydro-2H-1,4-benzoxazin-8-yloxy)acetate (915 mg) was used to obtain the object compound (682 mg, yield 77%).

Colorless needle crystal: mp. 161–161.5° C. (recrystallized from ethyl acetate/n-hexane)

$^1$H-NMR (300 MHz, CDCl$_3$) δ2.06 (3H, s), 2.52 (2H, t, J=7.5 Hz), 3.14 (2H, t, J=7.5 Hz), 3.22 (2H, t, J=4.5 Hz), 4.23 (2H, t, J=4.5 Hz), 4.61 (2H, s), 6.06 (1H, dd, J=1, 8 Hz), 6.31 (1H, dd, J=1, 8 Hz), 6.68 (1H, t, J=8 Hz), 7.22–7.35 (6H, m), 7.39–7.44 (4H, m).

IR (KBr method) 3450, 3058, 2928, 1744, 1609, 1506, 1489, 1433, 1348, 1241, 1214, 1187, 1162, 1131, 754, 737, 723, 698 cm$^{-1}$ Mass (EI, m/e) 449 (M$^+$)

| Elemental analysis | | | | |
|---|---|---|---|---|
| Calcd | C: 69.46% | H: 6.05% | N: 3.12% | S: 7.13% |
| Found | C: 69.70% | H: 6.17% | N: 3.15% | S: 7.45% |

Example 22

(4-(2-(1,1-diphenyl-2,2,2-trifluoroethylthio)ethyl)-3,4-dihydro-2H-1,4-benzoxazin-8-yloxy)acetic acid

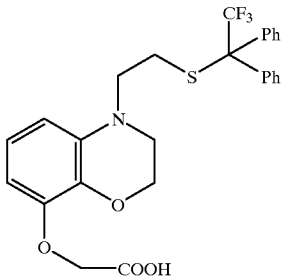

Methyl (4-(2-(1,1-diphenyl-2,2,2-trifluoroethylthio)ethyl)-3,4-dihydro-2H-1,4-benzoxazin-8-yloxy)acetate (585 mg) was dissolved in ethanol (15 ml), and a 4.89N sodium hydroxide aqueous solution (0.50 ml) was added to the resultant solution, and the mixture was stirred at room temperature for 3 hours. The solvent was distilled off under reduced pressure, and the residue was poured into a 5% citric acid aqueous solution, and then extracted with ethyl acetate. The resultant organic layer was washed with water and saturated brine, dried over magnesium sulfate, and then concentrated. The residue was recrystallized from ethyl acetate/n-hexane to obtain the object compound (472 mg, yield 83%).

Colorless plate crystal: mp. 140–140.5° C. (recrystallized from ethyl acetate/n-hexane)

$^1$H-NMR (300 MHz, CDCl$_3$) δ2.56 (2H, t, J=7.5 Hz), 3.19 (4H, m), 4.23 (2H, m), 4.61 (2H, s), 5.98 (1H, dd, J=1, 8 Hz), 6.30 (1H, dd, J=1, 8 Hz), 6.65 (1H, t, J=8 Hz), 7.32–7.36 (6H, m), 7.42–7.46 (4H, m).

IR (KBr method) 3430, 3040, 2894, 1748, 1611, 1502, 1487, 1448, 1435, 1348, 1243, 1216, 1187, 1149, 1129, 750, 716, 698 cm$^{-1}$ Mass (EI, m/e) 503 (M$^+$)

| Elemental analysis | | | | | |
|---|---|---|---|---|---|
| Calcd | C: 61.58% | H: 4.85% | N: 2.76% | S: 6.32% | F: 11.24% |
| Found | C: 61.68% | H: 4.85% | N: 2.87% | S: 6.54% | F: 11.37% |

Example 23

(4-(2-(1,1-bis-(4-fluorophenyl)ethylthio)-ethyl)-3,4-dihydro-2H-1,4-benzoxazin-8-yloxy)acetic acid

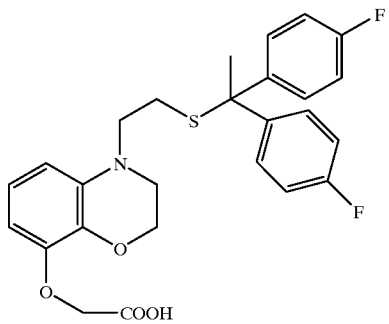

The same process as Example 20 was repeated except that methyl (4-(2-(1,1-bis-(4-fluorophenyl)ethylthio)ethyl)-3,4-dihydro-2H-1,4-benzoxazin-8-yloxy)acetate (254 mg) was used to obtain the object compound (166 mg, yield 67%).

Colorless needle crystal: mp. 142–143° C. (recrystallized from ethyl acetate/n-hexane)

$^1$H-NMR (300 MHz, CDCl$_3$) δ2.02 (3H, s), 2.50 (2H, t, J=7.6 Hz), 3.21 (2H, t, J=7.6 Hz), 3.26 (2H, t, J=7.6 Hz), 4.25 (2H, t, J=4.4 Hz), 4.62 (2H, s), 6.06 (1H, dd, J=8.2, 1.1 Hz), 6.31 (1H, dd, J=8.2, 1.1 Hz), 6.69 (1H, t, J=8.2 Hz), 6.95–7.03 (4H, m), 7.33–7.40 (4H, m).

IR (KBr method) 2926, 1744, 1715, 1611, 1504, 1454, 1431, 1346, 1238, 1214, 1187, 1162, 1131, 1108, 1064, 832, 756 cm$^{-1}$ Mass (EI, m/e) 485 (M$^+$)

| Elemental analysis | | | | |
|---|---|---|---|---|
| Calcd | C: 64.32% | H: 5.19% | N: 2.88% | S: 6.60% |
| Found | C: 64.22% | H: 5.13% | N: 2.99% | S: 6.61% |

Example 24

(4-(2-(1-methyl-1-phenylethylthio)ethyl)-3,4-dihydro-2H-1,4-benzoxazin-8-yloxy)acetic acid

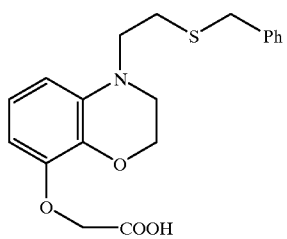

The same process as Example 20 was repeated except that methyl (4-(2-(1-methyl-1-phenylethylthio)ethyl)-3,4-dihydro-2H-1,4-benzoxazin-8-yloxy)acetate (358 mg) was used to obtain the object compound (271 mg, yield 78%).

Colorless needle crystal: mp. 114° C. (recrystallized from ethyl acetate/n-hexane)

$^1$H-NMR (300 MHz, CDCl$_3$) δ1.72 (6H, s), 2.42 (2H, m), 3.10 (2H, m), 3.19 (2H, t, J=4.5 Hz), 4.22 (2H, t, J=4.5 Hz), 4.60 (2H, s), 5.98 (1H, dd, J=1, 8 Hz), 6.29 (1H, dd, J=1, 8 Hz), 6.66 (1H, t, J=8 Hz), 7.24 (1H, m), 7.35 (2H, m), 7.56 (2H, m).

IR (KBr method) 2962, 2924, 1744, 1611, 1506, 1487, 1433, 1350, 1245, 1212, 1187, 1164; 1129, 752, 705, 698 cm$^{-1}$ Mass (EI, m/e) 387 (M$^+$)

| Elemental analysis | | | | |
|---|---|---|---|---|
| Calcd (+0.3H$_2$O) | C: 64.20% | H: 6.57% | N: 3.56% | S: 8.16% |
| Found | C: 64.12% | H: 6.51% | N: 3.57% | S: 8.03% |

Example 25

(4-(2-(benzylthio)ethyl)-3,4-dihydro-2H-1,4-benzoxazin-8-yloxy) acetic acid

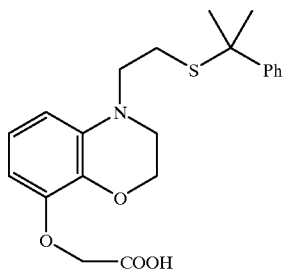

Methyl (4-(2-hydroxyethyl)-3,4-dihydro-2H-1,4-benzoxazin-8-yloxy)acetate (242 mg) was dissolved in methylene chloride (5 ml), and the resultant solution was cooled to 0° C. Triethylamine (0.38 ml) and methanesulfonyl chloride (0.10 ml) were added to the solution, and the mixture was stirred at 0° C. for 1 hour. The reaction solution was poured into a 3% citric acid aqueous solution, and then extracted with ethyl acetate. The resultant organic layer was washed with water and saturated brine, dried over sodium sulfate, and then concentrated to obtain the mesyl compound.

Anhydrous DMF (15 ml) was added to sodium hydride (72 mg) to form a suspension, and a solution of phenylmethanethiol (0.5 ml) in anhydrous DMF (1 ml) was added to the suspension at 0° C., followed by stirring at room temperature for 30 minutes. A solution of the above mesyl compound in anhydrous DMF (1 ml) was added to the resultant mixture at room temperature for 1 hour. The solvent was distilled off under reduced pressure, and the residue was poured into a 3% citric acid aqueous solution, and then extracted with ethyl acetate. The resultant organic layer was washed with water and saturated brine, dried over sodium sulfate, and then concentrated. The residue was recrystallized from ethyl acetate/n-hexane to obtain the object compound (199 mg, yield 61%).

Colorless needle crystal: mp. 127–131° C. (recrystallized from ethyl acetate/n-hexane)

$^1$H-NMR (300 MHz, CDCl$_3$) δ2.61 (2H, t, J=7.6 Hz), 3.30–3.38 (4H, m), 3.76 (2H, s), 4.27 (2H, t, J=4.4 Hz), 4.63 (2H, s), 6.25 (1H, dd, J=8.2, 1.1 Hz), 6.32 (1H, dd, J=8.2, 1.1 Hz), 6.72 (1H, t, J=8.2 Hz), 7.25–7.35 (5H, m).

IR (KBr method) 2898, 1742, 1711, 1611, 1576, 1506, 1487, 1456, 1431, 1350, 1325, 1263, 1241, 1214, 1187, 1160, 1129, 1104 cm$^{-1}$ Mass (EI, m/e) 359 (M$^+$)

| Elemental analysis | | | | |
|---|---|---|---|---|
| Calcd | C: 63.49% | H: 5.89% | N: 3.90% | S: 8.92% |
| Found | C: 63.20% | H: 5.90% | N: 3.97% | S: 8.78% |

Example 26

(4-(2-(2,2-diphenylpropylthio)ethyl)-3,4-dihydro-2H-1,4-benzoxazin-8-yloxy)acetic acid

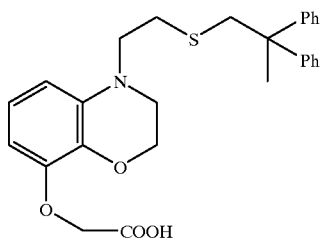

The same process as Example 20 was repeated except that methyl (4-(2-(2,2-diphenylpropylthio)ethyl)-3,4-dihydro-2H-1,4benzoxazin-8-yloxy)acetate (119 mg) was used to obtain the object compound (85 mg, yield 74%).

Colorless needle crystal: mp. 138–139° C. (recrystallized from ethyl acetate/n-hexane)

$^1$H-NMR (300 MHz, CDCl$_3$) δ1.78 (3H, s), 2.35 (2H, t, J=7.1 Hz), 3.24–3.33 (6H, m), 4.23 (2H, t, J=4.4 Hz), 4.62 (2H, s), 6.28–6.33 (2H, m), 6.76 (1H, t, J=8.2 Hz), 7.17–7.31 (10H, m).

IR (KBr method) 3514, 3428, 3392, 2926, 1742, 1611, 1576, 1508, 1487, 1460, 1435, 1350, 1245, 1212, 1187, 1164, 1129, 1046, 754, 700 cm$^{-1}$ Mass (EI, m/e) 463 (M$^+$)

Example 27

(4-(2-(1,1-bis-(3-thienyl)ethylthio)ethyl-3,4-dihydro-2H-1,4-benzoxazin-8-yloxy)acetic acid

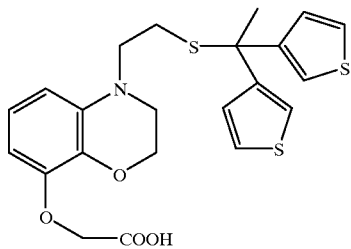

Methyl (4-(2-(1,1-bis-(3-thienyl)ethylthio)ethyl-3,4-dihydro-2H-1,4-benzoxazin-8-yloxy)acetate (183 mg) was dissolved in THF (1 ml) and methanol (2 ml), and a 2N sodium hydroxide aqueous solution (0.4 mL) was added to the resultant solution at room temperature for 20 minutes. The solvent was distilled off under reduced pressure, and the residue was poured into a 5% citric acid aqueous solution, and then extracted with ethyl acetate. The resultant organic layer was washed with water and saturated brine, dried over sodium sulfate, and then concentrated. The residue was recrystallized from ethyl acetate/n-hexane to obtain the colorless granular object compound (161 mg, yield 91%).

Colorless granular crystal: mp. 149° C. (recrystallized from ethyl acetate/n-hexane)

$^1$H-NMR (300 MHz, CDCl$_3$) δ2.05 (3H, s), 2.54 (2H, t, J=7.4 Hz), 3.17 (2H, t, J=7.4 Hz), 3.25 (2H, t, J=4.4 Hz), 4.25 (2H, t, J=4.4 Hz), 4.62 (2H, s), 6.11 (1H, dd, J=8.2, 1.1 Hz), 6.31 (1H, dd, J=8.2, 1.1 Hz), 6.72 (1H, t, J=8.2 Hz), 7.12 (2H, dd, J=3.0, 1.4 Hz), 7.14 (2H, dd, J=5.2, 1.4 Hz), 7.29 (2H, dd, J=5.2, 3.0 Hz).

IR (KBr method) 3432, 3092, 2970, 2922, 1744, 1715, 1700, 1607, 1574, 1506, 1487, 1464, 1456, 1437, 1431, 1371, 1352, 1330, 1278, 1251, 1241, 1212, 1189, 1170, 1127, 1683, 1042 cm$^{+1}$ Mass (EI, m/e) 461 (M$^+$)

| Elemental analysis | | | | |
|---|---|---|---|---|
| Calcd (+0.4H$_2$O) | C: 56.36% | H: 5.12% | N: 2.99% | S: 20.52% |
| Found | C: 56.34% | H: 5.04% | N: 3.03% | S: 20.45% |

Example 28

(4-(2-(diphenylmethoxy)ethyl)-3,4-dihydro-2H-1,4-benzoxazin-8-yloxy)acetic acid

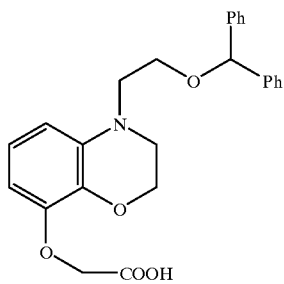

Methyl (4-(2-(diphenylmethoxy)ethyl)-3,4-dihydro-2H-1,4-benzoxazin-8-yloxy)acetate (320 mg) was dissolved in THF (1 ml) and methanol (2 ml), and a 2N sodium hydroxide aqueous solution (0.9 ml) was added to the resultant solution, and the mixture was stirred at room temperature for 1 hour. The solvent was distilled off under reduced pressure, and the residue was poured into a 5% citric acid aqueous solution, and then extracted with ethyl acetate. The resultant organic layer was washed with water and saturated brine, dried over sodium sulfate, and then concentrated. The residue was recrystallized from ethyl acetate/n-hexane to obtain colorless needle crystals of the object compound (221 mg, yield 71%).

Colorless needle crystal: mp. 112–113° C. (recrystallized from ethyl acetate/n-hexane)

$^1$H-NMR (300 MHz, CDCl$_3$) δ3.48 (2H, t, J=4.4 Hz), 3.54 (2H, t, J=5.4 Hz), 3.65 (2H, t, J=5.4 Hz), 4.26 (2H, t, J=4.4 Hz), 4.64 (2H, s), 5.34 (1H, s), 6.32 (1H, dd; J=8.2, 1.2 Hz), 6.41 (1H, dd, J=8.2, 1.2 Hz), 6.73 (1H, t, J=8.2 Hz), 7.20–7.32 (10H, m).

IR (KBr method) 2894, 2866, 2678, 1744, 1613, 1576, 1506, 1489, 1454, 1439, 1350, 1328, 1278, 1247, 1212, 1189, 1152, 1110, 1079, 754, 741, 698 cm$^{-1}$ Mass (EI, m/e) 419 (M$^+$)

| Elemental analysis | | | |
|---|---|---|---|
| Calcd | C: 71.58% | H: 6.01% | N: 3.34% |
| Found | C: 71.22% | H: 5.98% | N: 3.40% |

Example 29

(4-(2-(1,1-diphenylethoxy)ethyl)-3,4-dihydro-2H-1,4-benzoxazin-8-yloxy)acetic acid

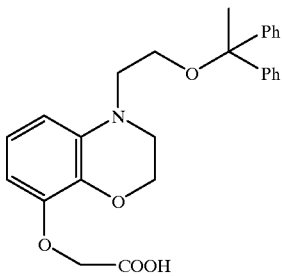

The same process as Example 28 was repeated except that methyl (4-(2-(1,1-diphenylethoxy)ethyl)-3,4-dihydro-2H-1,4-benzoxazin-8-yloxy)acetate (308 mg) was used to obtain the object compound (193 mg, yield 65%). Colorless granular crystal: mp. 108° C. (recrystallized from ethyl acetate/n-hexane)

$^1$H-NMR (300 MHz, CDCl$_3$) δ1.83 (3H, s), 3.40–3.51 (6H, m), 4.27 (2H, t, J=4.4 Hz), 4.63 (2H, s), 6.30 (1H, dd, J=8.2, 1.1 Hz), 6.33 (1H, dd, J=8.2, 1.1 Hz), 6.69 (1H, t, J=8.2 Hz), 7.17–7.33 (10H, m).

IR (KBr method) 3060, 2986, 2910, 2876, 1746, 1613, 1578, 1489, 1448, 1437, 1348, 1241, 1214, 1187, 1151, 1106, 1075, 1052, 768, 758, 700 cm$^{-1}$ Mass (EI, m/e) 433 (M$^+$)

Example 30

(4-(4,4-diphenylpentyl)-8-hydroxy-3-oxo-3,4-dihydro-2H-1,4-benzoxazin-8-yloxy)acetic acid

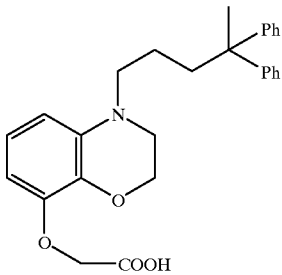

Methyl (4-(4,4-diphenylpentyl)-8-hydroxy-3-oxo-3,4-dihydro-2H-1,4-benzoxazin-8-yloxy)acetate (308 mg) was dissolved in THF (1 ml) and methanol (2 ml), and a 2N sodium hydroxide aqueous solution (0.8 ml) was added to the resultant solution, and the mixture was stirred at room temperature for 20 minutes. The solvent was distilled off under reduced pressure, and the residue was poured into a 5% citric acid aqueous solution, and then extracted with ethyl acetate. The resultant organic layer was washed with water and saturated brine, dried over sodium sulfate, and then concentrated. The residue was recrystallized from ethyl acetate/n-hexane to obtain colorless granular crystals of the object compound (249 mg, yield 79%). Colorless granular crystal: mp. 133° C. (recrystallized from ethyl acetate/n-hexane)

$^1$H-NMR (300 MHz, CDCl$_3$) δ1.36–1.48 (2H, m), 1.63 (3H, s), 2.08–2.17 (2H, m), 3.16 (2H, t, J=8.4 Hz), 3.21 (2H, t, J=4.4 Hz), 4.25 (2H, t, J=4.4 Hz), 4.62 (2H, s), 6.26 (1H, d, J=8.5 Hz), 6.30 (1H, d, J=8.0 Hz), 6.71 (1H, t, J=8.2 Hz), 7.16–7.22 (6H, m), 7.23–7.31 (4H, m).

IR (KBr method) 3424, 2932, 2876, 1744, 1613, 1576, 1489, 1462, 1435, 1371, 1350; 1325, 1245, 1209, 1187, 1164, 1137, 1110, 1042, 1029, 911, 890, 752, 708 cm$^{-1}$ Mass (EI, m/e) 431 (M$^+$)

| Elemental analysis | | | |
|---|---|---|---|
| Calcd (+0.25H$_2$O) | C: 74.37% | H: 6.82% | N: 3.21% |
| Found | C: 74.36% | H: 6.81% | N: 3.21% |

Example 31

(4-(2-(1,1-diphenylethylthio)ethyl)-3-oxo-3,4-dihydro-2H-1,4-benzoxazin-8-yloxy)acetic acid

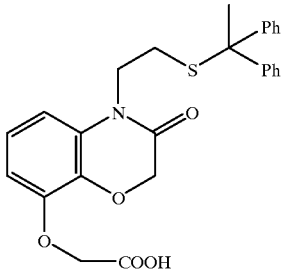

The same process as Example 26 was repeated except that methyl (4-(2-(1,1-diphenylethylthio)ethyl)-3-oxo-3,4-dihydro-2H-1,4-benzoxazin-8-yloxy)acetate (170 mg) was used to obtain the object compound (155 mg, yield 94%). Colorless powder: mp. 106° C. (recrystallized from dichloromethane/n-hexane)

$^1$H-NMR (300 MHz, CDCl$_3$) δ2.08 (3H, s), 2.57 (2H, m), 3.81 (2H, m), 4.60 (2H, s), 4.70 (2H, s), 6.16 (1H, dd, J=1, 8 Hz), 6.61 (1H, dd, J=1, 8 Hz), 6.84 (1H, t, J=8 Hz), 7.21–7.34 (6H, m), 7.40–7.45 (4H, m).

IR (KBr method) 3038, 2924, 1734, 1655, 1611, 1591, 1485, 1421, 1232, 1199, 1149, 1052, 766, 737, 700 cm$^{-1}$ Mass (EI, m/e) 463 (M$^+$)

| Elemental analysis | | | | |
|---|---|---|---|---|
| Calcd (+1.0H$_2$O) | C: 64.85% | H: 5.65% | N: 2.91% | S: 6.66% |
| Found | C: 65.02% | H: 5.46% | N: 2.76% | S: 6.49% |

Example 32

(4-((diphenylmethylcarbamoyl)methyl)-3-oxo-3,4-dihydro-2H-1,4-benzoxazin-8-yloxy)acetic acid

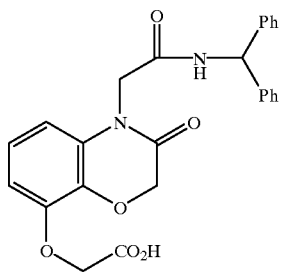

Methyl (4-((diphenylmethylcarbamoyl)methyl)-3-oxo-3,4-dihydro-2H-1,4-benzoxazin-8-yloxy)acetate (260 mg) was suspended in a solvent mixture of methanol (20 ml) and THF (10 ml), and the resultant suspension was stirred at room temperature. A 1N sodium hydroxide aqueous solution (2 ml) was added to the resultant solution, and the mixture was stirred at room temperature for 3 hours, followed by concentration. Water (60 ml) was added to the residue, and 1N hydrochloric acid was added to the mixture to adjust pH to 3, followed by extraction with ethyl acetate. The resultant organic layer was washed with saturated brine, dried over sodium sulfate, and then concentrated. The residue was recrystallized from ethyl acetate/n-hexane to obtain the object compound (194 mg, yield 77%). mp. 232.0–234.0° C.

$^1$H-NMR (300 MHz, DMSO-d$_6$) δ4.66 (4H, s), 4.69 (2H, s), 6.10 (1H, d, J=8.4 Hz), 6.60 (1H, dd, J=1.2, 8.4 Hz), 6.67 (1H, dd, J=1.2, 8.4 Hz), 6.89 (1H, t, J=8.4 Hz), 7.22–7.38 (10H, m), 9.16 (1H, d J=8.7 Hz).

IR (KBr method) 3300, 1737, 1682, 1660, 1612, 1541, 1484, 1400, 1286, 1236, 1192, 1160, 1106, 1057, 974, 862, 765, 699 cm$^{-1}$ Mass (EI, m/e) 446 (M$^+$)

| Elemental analysis | | | |
|---|---|---|---|
| Calcd | C: 67.26% | H: 4.97% | N: 6.27% |
| Found | C: 67.11% | H: 5.09% | N: 6.33% |

Example 33

3-(4-(2-(1,1-diphenylethylthio)ethyl)-3-oxo-3,4-dihydro-2H-1,4-benzoxazin-8-yl)propionic acid

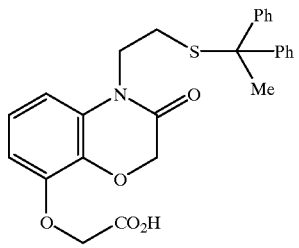

Methyl 3-(4-(2-(1,1-diphenylethylthio)ethyl)-3-oxo-3,4-dihydro-2H-1,4-benzoxazin-8-yl)propionate (245 mg) was dissolved in a solvent mixture of ethanol (2.0 ml) and THF (2.0 ml), and a 1.0N sodium hydroxide aqueous solution (1.1 ml) was added to the resultant solution, and the mixture was stirred at room temperature for 3 hours. The solvent was distilled off under reduced pressure, and a 1.0N hydrochloric acid aqueous solution (1.1 ml) was added to the residue. The mixture was diluted with water, and then extracted with ethyl acetate. The resultant organic layer was dried over magnesium sulfate, and then concentrated. The residue was recrystallized from ethyl acetate/n-hexane to obtain the object compound (169 mg, yield 70%). mp. 110.1° C. (recrystallized from ethyl acetate/n-hexane)

$^1$H-NMR (300 MHz, CD$_3$OD) δ2.03 (3H, s), 2.53–2.58 (4H, m), 2.89 (2H, t, J=7.5 Hz), 3.87 (2H, t, J=7.7 Hz), 4.54 (2H, s), 6.47 (1H, dd, J=1.7, 8.0 Hz), 6.83–6.92 (2H, m), 7.18–7.30 (6H, m), 7.36–7.40 (4H, m).

IR (KBr method) 3448, 3052, 1685, 1590, 1480, 1443, 1398, 1319, 1219, 1126, 1092, 1034, 954, 823, 743, 701, 559, 491 cm$^{-1}$ Mass (EI, m/e) 461 (M$^+$)

| Elemental analysis | | | |
|---|---|---|---|
| Calcd | C: 70.26% | H: 5.90% | N: 3.03% | S: 6.95% |
| Found | C: 70.35% | H: 5.80% | N: 2.97% | S: 7.03% |

Example 34

(1-(2-(1,1-diphenylethylthio)ethyl)-1,2,3,4-tetrahydroquinolin-5-yloxy)acetic acid

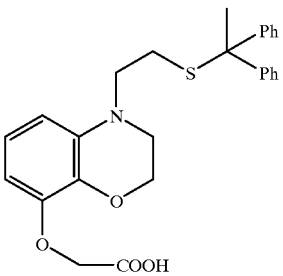

Methyl (1-(2-(1,1-diphenylethylthio)ethyl)-1,2,3,4-tetrahydroquinolin-5-yloxy)acetate (268 mg) was dissolved in methanol (10 ml) and THF (5 ml), and the resultant solution was stirred at room temperature. A 1N sodium hydroxide aqueous solution (1.00 ml) was added to the solution, and the mixture was stirred at room temperature. After disappearance of the raw materials was confirmed, the solvent was distilled off under reduced pressure. Water (20 ml) was added to the residue, and the resultant mixture was. neutralized with 1N hydrochloric acid (1.00 ml), and then extracted with ethyl acetate. The resultant organic layer was washed with saturated brine, dried over anhydrous sodium sulfate, and then concentrated. The residue was recrystallized from methylene chloride/hexane to obtain the object compound (173 mg, yield 67%).

Pale yellow needle crystal: mp. 150.5–152.0° C.

$^1$H-NMR (300 MHz, CDCl$_3$) δ1.80–190 (2H, m), 2.06 (3H, s), 2.47–2.55 (2H, m), 2.67 (2H, t, J=6.6 Hz), 3.04–3.19 (4H, m), 4.61 (2H, s), 5.93 (1H, d, J=8.1 Hz), 6.05 (1H, d, J=8.1 Hz), 6.88 (1H, t, J=8.1 Hz), 7.20–7.34 (6H, m), 7.39–7.46 (4H, m).

IR (KBr method) 1744, 1745, 1605, 1574, 1493, 1466, 1433, 1249, 1201, 1164, 1127, 1062, 1029, 913, 756, 698 cm$^{-1}$ Mass (FAB, m/e) 448 (M+H$^+$)

Example 35

(1-(2-(1,1-diphenylethylthio)ethyl)-2,3,4,5-tetrahydro-1H-benzazepin-6-yloxy)acetic acid

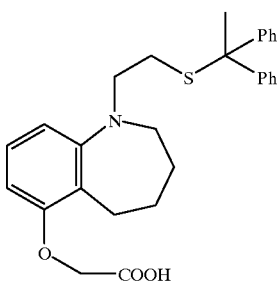

The same process as Example 34 was repeated except that methyl (1-(2-(1,1-diphenylethylthio)ethyl)-2,3,4,5-tetrahydro-1H-1-benzazepin-6-yloxy)acetate (283 mg) was used to obtain the object compound (171 mg, yield 62%).

$^1$H-NMR (300 MHz, CDCl$_3$) δ1.68–1.52 (4H, m), 2.05 (3H, s), 2.45–2.53 (2H, m), 2.80–2.91 (4H, m), 3.06–3.14 (2H, m), 4.63 (2H, s), 6.39 (2H, d, J=8.1 Hz), 6.97 (1H, t, J=8.1 Hz), 7.16–7.32 (6H, m), 7.36–7.44 (4H, m).

IR (liquid film method) 2928, 1734, 1597, 1580, 1464, 1444, 1220, 1187, 1139, 1114, 1029, 909, 731, 698 cm$^{-1}$ Mass (EI, m/e) 461 (M$^+$)

Example 36

(3-(2-(diphenylmethylthio)ethyl)-2,3-dihydrobenzofuran-7-yloxy)acetic acid

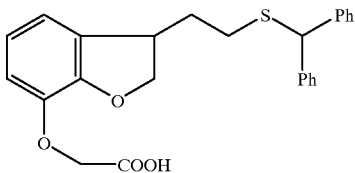

Methyl (3-(2-(diphenylmethylthio)ethyl)-2,3-dihydrobenzofuran-7-yloxy)acetate (205 mg) was dissolved in methanol/THF (4/1.5 ml), and a 2N sodium hydroxide aqueous solution (0.4 ml) was added to the resultant solution, and the mixture was stirred at room temperature for 30 minutes. The reaction solution was neutralized with 1N hydrochloric acid, poured into a water layer, and then extracted with ethyl acetate (10 ml) twice. The combined organic layers were washed with saturated brine, dried over sodium sulfate, and then concentrated under reduced pressure. The residue was purified by column chromatography (DIOL, n-hexane/diethyl ether=1/2) to obtain the object compound (105 mg, yield 53%).

mp. 88–89° C. (recrystallized from ethyl acetate/n-hexane)

$^1$H-NMR (300 MHz, CDCl$_3$) δ1.86–1.74 (1H, m), 2.02–1.90 (1H, m), 2.45 (2H, t, J=7.4 Hz), 3.57–3.47 (1H, m), 4.13 (1H, dd, J=8.8, 6.0 Hz), 4.59 (1H, t, J=8.8 Hz), 4.71 (2H, s), 5.15 (1H, s), 6.77–6.72 (3H, m), 7.44–7.20 (10H, m).

IR (KBr method) 3482, 3360, 1736, 1711, 1624, 1593, 1491, 1460, 1450, 1435, 1267, 1191, 1118, 1079, 961, 940, 770, 748, 731, 702 cm$^{-1}$ Mass (EI, m/e) 420 (M$^+$)

| Elemental analysis | | | |
|---|---|---|---|
| Calcd | C: 71.40% | H: 5.75% | S: 7.63% |
| Found | C: 71.11% | H: 5.76% | S: 7.63% |

Example 37

(3-(2-(1,1-diphenylethylthio)ethyl)-2,3-dihydrobenzofuran-7-yloxy)acetic acid

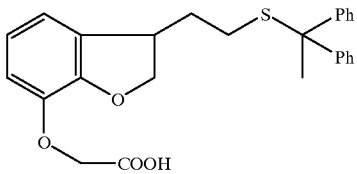

The same process as Example 36 was repeated except that methyl (3-(2-(1,1-diphenylethylthio)ethyl)-2,3-dihydrobenzofuran-7-yloxy)acetate (360 mg) was used to obtain the object compound (313 mg, yield 90%).

m.p 65–67° C. (recrystallized from n-hexane/chloroform)

$^1$H-NMR (300 MHz, CDCl$_3$) δ1.88–1.60 (2H, m), 2.06 (3H, s), 2.41–2.26 (2H, m), 3.51–3.41 (1H, m), 4.07 (1H, dd, J=8.8, 6.0 Hz), 4.51 (1H, t, J=8.8 Hz), 4.70 (2H, s), 6.78–6.66 (3H, m), 7.44–7.21 (10H, m).

IR (KBr method) 3492, 3376, 3060, 3032, 2972, 2932, 1719, 1624, 1595, 1492, 1462, 1399, 1375, 1322, 1269, 1192, 1117, 1060, 1029, 957, 828, 762, 733 cm$^{-1}$ Mass (EI, m/e) 434 (M$^+$)

| Elemental analysis | | | |
|---|---|---|---|
| Calcd | C: 69.00% | H: 6.24% | S: 7.09% |
| Found | C: 69.09% | H: 6.19% | S: 7.04% |

Example 38

(4-(2-(1,1-diphenylethylsulfinyl)ethyl)-3,4-dihydro-2H-1,4-benzoxazin-8-yloxy)acetic acid

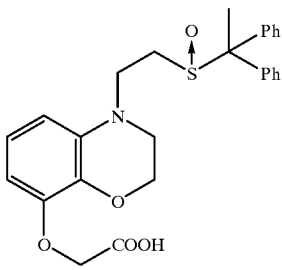

(4-(2-(1,1-diphenylethylthio)ethyl)-3,4-dihydro-2H-1,4-benzoxazin-8-yloxy)acetic acid (51 mg) was dissolved in

91 methylene chloride (5 ml), and the resultant solution was stirred at room temperature. m-CPBA (20 mg) was then added to the solution, and the mixture was stirred at room temperature for 4 hours. The reaction mixture was added to water (20 ml), and then extracted with ethyl acetate. The resultant organic layer was washed with saturated brine, dried over sodium sulfate, and concentrated. The residue was purified by Lober® column chromatography (DIOL, type A, developing solvent: n-hexane/ethyl acetate=1/2) to obtain the object compound (43 mg, yield 81%).

$^1$H-NMR (300 MHz, CDCl$_3$) δ1.97 (3H, s), 2.26–2.46 (2H, m), 3.20–3.37 (2H, m), 3.52–3.60 (2H, m), 4.22–4.27 (2H, m), 4.64 (2H, s), 6.15 (1H, dd, J=1.2, 8.4 Hz), 6.30 (1H, dd, J=1.2, 8.4 Hz, 6.65(1H, t, J=8.4 Hz), 7.27–7.46 (10H, m).

Mass (FAB, m/e) 466 (M+H)$^+$

Example 39

Sodium (4-(2-(1,1-diphenylethylthio)ethyl)-3,4-dihydro-2H-1,4-benzoxazin-8-yloxy)acetate

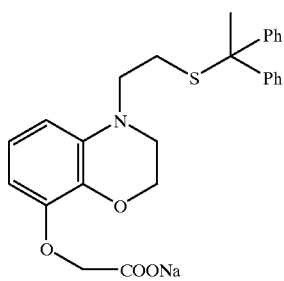

A 0.0978N sodium hydroxide aqueous solution (11.54 ml) and distilled water (10 ml) were added to (4-(2-(1,1-diphenylethylthio)ethyl)-3,4-dihydro-2H-1,4-benzooxazine-8-yloxy)acetic acid (510 mg), and the mixture was heated to form a solution. The solution was filtered with a membrane filter, and the residue was washed with 10 ml of distilled water. The filtrate was freeze-dried to obtain the object compound (535 mg, yield 100%).

Colorless amorphous mp. 110° C.

$^1$H-NMR (300 MHz, D$_2$O, 30° C.) δ1.79 (3H, s), 2.24 (2H, m), 2.75 (4H, m), 3.86 (2H, m), 4.23 (2H, s), 5.66 (1H, br), 6.08 (1H, br), 6.37 (1R, br), 7.00 (6H, m), 7.23 (4H, m).

IR (KBr method) 3400, 2926, 1742, 1620, 1585, 1475, 1433, 1272, 1212, 1108, 1062, 1017, 1007, 826 cm$^{-1}$ Mass (FAB-Pos, m/e) 472 (M+H)$^+$, 494 (M+Na)$^+$

| Elemental analysis | | | | |
|---|---|---|---|---|
| Calcd (+1.6H$_2$O) | C: 62.41% | H: 5.88% | N: 2.80% | S: 6.41% |
| Found | C: 62.35% | H: 5.77% | N: 3.02% | S: 6.59% |

92

Example 40

Megluminium (4-(2-(1,1-diphenylethylthio)ethyl)-3,4-dihydro-2H-1,4-benzoxazin-8-yloxy)acetate

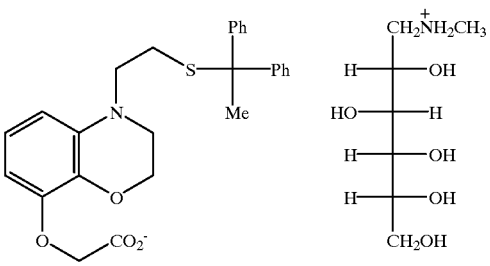

Meglumine (243 mg) was suspended in ethanol (24 ml), and then heated to form a solution. (4-(2-(1,1-diphenylethylthio)ethyl-3,4-dihydro-2H-1,4-benzooxazine-8-yloxy)acetic acid (500 mg) was dissolved in ethanol (50 ml) by heating, and the thus-obtained solution was added to the meglumine solution, and the mixture was allowed to stand at room temperature. The precipitated solid was filtered off to obtain the object compound (671 mg, yield 94%).

mp. 137.0–141.5° C.

$^1$H-NMR (500 MHz, DMSO-d$_6$) δ2.04 (3H, s), 2.45 (3H, s), 2.42–2.52 (2H, m), 2.85 (1H, dd, J=8.5, 12.5 Hz), 2.94 (1H, dd, J=3.5, 12.5 Hz), 3.13 (2H, t, J=7.8 Hz), 3.16 (2H, t, J=4.3 Hz), 3.36–3.44 (2H, m), 3.46–3.52 (1H, m), 3.58 (1H, dd, J=3.5, 11.0 Hz), 3.65 (1H, dd, J=1.5, 5.0 Hz), 3.81–3.87 (1H, m), 4.05 (2H, t, J=4.0 Hz), 4.16 (2H, s), 5.88 (1H, d, J=7.5 Hz), 6.09 (1H, dd, J=1.0, 8.5 Hz), 6.50 (1H, t, J=8.3 Hz), 7.22–7.28 (2H, m), 7.30–7.42 (8H, m).

Mass (FAB, m/e) 448 (M-H)$^-$

| Elemental analysis | | | | |
|---|---|---|---|---|
| Calcd | C: 61.47% | H: 6.88% | N: 4.34% | S: 4.97% |
| Found | C: 61.22% | H: 6.80% | N: 4.36% | S: 4.99% |

Example 41

Diethanolammonium (+)-3-(2-(3-(2-hydroxyphenyl)propylthio)ethyl)-2,3-dihydrobenzofuran-7-yloxyacetate

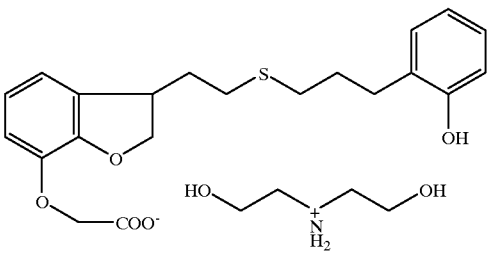

Methyl (+)-3-(2-(3-(2-hydroxyphenyl)propylthio)ethyl)-2,3-dihydrobenzofuran-7-yloxyacetate (160 mg) was dissolved in methanol (4 ml), and a 2N sodium hydroxide aqueous solution (0.4 ml) was added to the resultant solution, and the mixture was stirred at room temperature for 1.5 hours. The reaction solution was poured into water and then extracted with ethyl acetate twice. The combined organic layers were washed with saturated brine, and dried over sodium sulfate. Sodium sulfate was filtered off, and the filtrate was concentrated. The residue was purified by Lober® column DIOL (elution solvent: hexane/ethyl acetate=1/2) to obtain (+)-3-(2-(3-(2-hydroxyphenyl)propylthio)ethyl)-2,3-dihydrobenzofuran-7-yloxyacetic acid (145 mg). This product was dissolved in chloroform, and diethanolamine was added to the resultant solution. The solvent was distilled off under reduced pressure, and the residue was recrystallized from hexane/ethanol to obtain the object compound (140 mg, yield 76%).

$[\alpha]_D$ 20=+38.24 (c=0.570, MeOH)

mp. 107–109° C. (recrystallized from ethyl acetate/n-hexane)

$^1$H-NMR (300 MHz, $D_2O$) δ1.60–1.85 (4H, m), 2.33–2.48 (4H, m), 2.58 (2H, t, J=7.1 Hz), 3.19–3.23 (4H, m), 3.36–3.45 (1H, m), 3.83–3.86 (4H, m), 4.15 (1H, dd, J=6.3, 9.1 Hz), 4.54(1H, t, J=9.1 Hz), 6.64–6.84 (5H, m), 7.02–7.06 (2H, m).

IR (KBr method) 3276, 2941, 1618, 1372, 1490, 1455, 1430, 1372, 1326, 1282, 1190, 1077, 1043, 951 $cm^{-1}$ Mass (EI, m/e) 388 ($M^+$)

Example 42

Platelet Aggregation Inhibiting Action 1

The blood collected from the human medial cubital vein was centrifuged at 800 rpm for 10 minutes, and the upper portion was collected as platelet-rich plasma (PRP). PRP was dispensed to small test tubes, and $TXA_2$ agonist U-46619 was added thereto (the final concentration 1 to 4 μM) to induce platelet aggregation. The degree of platelet aggregation was measured as a change in turbidity by a platelet aggregation measuring device (Hematracer 1, Nikko Bioscience). Each compound was added 1 minute before the addition of U-46619, and a concentration at which aggregation was 50% inhibited was calculated as a IC50 value.

The activities of the compounds of the present invention were evaluated by the above method. The results are summarized in Table 1.

TABLE 1

| Example No. | Platelet aggregation inhibiting action IC50 (μM) |
|---|---|
| 20 | 1.3 |
| 21 | 0.55 |
| 28 | 5.7 |
| 29 | 5.5 |
| 34 | 0.59 |
| 36 | 0.55 |
| 37 | 0.49 |

Example 43

Platelet Aggregation Inhibiting Action 2

The blood collected from the human medial cubital vein was centrifuged 800 rpm for 10 minutes, and the upper portion was collected as platelet-rich plasma (PRP). PRP was dispensed to small test tubes, and ADP was added thereto (the final concentration 1 to 10 μM) to induce platelet aggregation. The degree of platelet aggregation was measured as a change in turbidity by a platelet aggregation measuring device (Hematracer 1, Nikko Bioscience). Each compound was added 1 minute before the addition of ADP, and a concentration at which aggregation was 50% inhibited was calculated as IC50 value.

The activities of the compounds of the present invention were evaluated by the above method. The results are summarized in Table 2.

TABLE 2

| Example No. | Platelet aggregation inhibiting action IC50 (μM) |
|---|---|
| 20 | 2.0 |
| 21 | 1.8 |
| 28 | 16 |
| 29 | 16 |
| 34 | 1.3 |
| 36 | 0.95 |
| 37 | 1.8 |

Example 44

$TXA_2$ Receptor Binding Test

The blood collected from the human antebrachial vein and 1/10 volume of ACD solution (85 mM trisodium citrate, 65 mM citric acid, 2% glucose) were mixed, and 8 ml of the mixture was dispensed to each of Spitz tubes. The platelet-rich plasma obtained by centrifugation at room temperature and 200×g for 10 minutes was further centrifuged at 1000×g for 15 minutes to obtain platelets. The thus-obtained platelets were centrifugally washed with a cleaning buffer (115 mM sodium chloride, 4.3 mM potassium dihydrogen phosphate, 5.5 mM glucose, 1 mM disodium EDTA, 10 μM indomethane, pH 6.5), and 1 ml of a dissolution buffer (10 mM tris(hydroxymethyl)aminomethane, 5 mM magnesium chloride, 2 mM disodium EDTA, pH 7.4) was added to-the platelets, followed by three times of freezing in liquid nitrogen and melting at room temperature to crush the platelets. The crushed platelets were cleaned by three times of ultracentrifugation (40000×g, 20 minutes each) using 5 mm ice-cold tris-hydrochloric acid buffer. The finally obtained sediment was used as a platelet membrane fraction.

As a $TXA_2$ receptor ligand, tritium-labeled SQ29548 ($[^3H]$SQ29548) was used. As a solvent for receptor binding reaction, a 50 mM tris-hydrochloric acid buffer (5 nM magnesium chloride, pH 7.4) was used. A saturation test was conducted by reaction of $[^3H]$SQ29548 (100 μl) at a final concentration of 3 to 100 nM and 0.1 mg protein/ml of platelet membrane fraction suspension (100 μl) at 25° C. for 30 minutes under shaking. Competitive experiment was carried out by reaction of a mixed solution (100 μl) of a test compound dissolved in an appropriate solvent and diluted and $[^3H]$SQ29548 at a final concentration of 10 nM, and 0.1 mg protein/ml of platelet membrane fraction suspension (100 μl) at 25° C. for 30 minutes under shaking. After the completion of reaction, the membrane fraction was recovered on a glass filter by a cell harvester, and washed with an ice-cold buffer. Then, radioactivity was measured by a scintillation counter. Nonspecific binding to a substance other than the receptor was determined by reaction in the presence of SQ29548 at a final concentration of 10 nM. In the competitive experiment, IC50 value and Hill coefficient of each of the test compounds were determined by pseudo-Hill plots, and the receptor dissociation constant (Ki value) was determined from the IC50 value and the receptor dissociation constant (Kd value) of $[^3H]$SQ29548, which was obtained by saturation experiment, according to the following equation:

Ki value=IC50 value/[1+(radioactive ligand concentration/Kd value)]

The activities of the compounds of the present invention were evaluated by the above method. The results summarized in Table 3.

TABLE 3

| Example No. | TXA$_2$ receptor affinity Ki ($\mu$M) |
|---|---|
| 21 | 0.050 |
| 34 | 0.12 |
| 36 | 0.070 |

Example 45

PGI$_2$ Receptor Binding Experiment

As a PGI$_2$ receptor ligand, tritium-labeled (1R, 2R, 3aS, 8bS)-2,3,3a,8b-tetrahydro-2-hydroxy-1-[(E)-(3S, 4S)-3-hydroxy-4-methyl-1-octene-6-ynyl]-1H-cyclopenta[b]benzofuran-4-butanoic acid (compound A) was used. A saturation test was conducted by reaction of compound A (100 $\mu$l) at a final concentration of 3 to 100 nM and 0.1 mg protein/ml of platelet membrane fraction suspension (100 $\mu$l) at 4° C. for 60 minutes under shaking. Competitive experiment was carried out by reaction of a mixed solution (100 $\mu$l) of a test compound dissolved in an appropriate solvent and diluted and compound A at a final concentration of 10 nM, and 0.1 mg protein/ml of platelet membrane fraction suspension (100 $\mu$l) at 4° C. for 60 minutes under shaking. After the completion of reaction, the membrane fraction was recovered on a glass filter by a cell harvester, and washed with an ice-cold buffer. Then, radioactivity was measured by a scintillation counter. Nonspecific binding to a substance other than the receptor was determined by reaction in the presence of beraprost sodium at a final concentration of 10 nM. In the competitive experiment, IC50 value and Hill coefficient of each of test compounds were determined by pseudo-Hill plots, and the receptor dissociation constant (Ki value) was determined from the IC50 value and the receptor dissociation constant (Kd value) of compound A, which was obtained by saturation experiment, according to the following equation:

Ki value=IC50 value/[1+(radioactive ligand concentration/Kd value)]

The activities of the compounds of the present invention were evaluated by the above method. The results summarized in Table 4.

TABLE 4

| Example No. | PGI$_2$ receptor affinity Ki ($\mu$M) |
|---|---|
| 21 | 0.43 |
| 34 | 0.52 |
| 36 | 0.23 |

INDUSTRIAL APPLICABILITY

The compounds of the present invention have the strong TXA$_2$ receptor antagonistic action and PGI$_2$ receptor agonistic action, and are effective as medicines for treating or preventing diseases concerning TXA$_2$.

What is claimed is:

1. A benzene fused heterocyclic derivative, represented by the following formula (II):

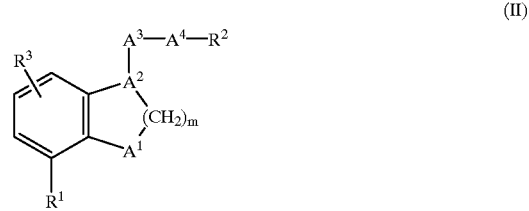

wherein A$^1$ is —O— or —S—;
A$^2$ is

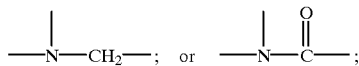

A$^3$ is alkylene having 1 to 4 carbon atoms, alkenylene having 2 to 4 carbon atoms, or alkynylene having 2 to 4 carbon atoms;

A$^4$ is —S(O)$_p$—, —O—, —CH$_2$—, —NR$^5$—, —NR$^5$CO—, or —CONR$^5$—, wherein R$^5$ is hydrogen, alkyl having 1 to 5 carbon atoms, or phenyl (which may be substituted by a group or groups selected from alkyl having 1 to 5 carbon atoms, phenyl, hydroxyl, alkoxy having 1 to 5 carbon atoms, phenoxy, halogen, trifluoromethyl, cyano, nitro, amino, and alkylamino having 1 to 5 carbon atoms), and p is an integer of 0 to 2;

m is 1;

R$^1$ is —X—(CH$_2$)$_n$—COOR$^6$, wherein X is —O—, —S—, or —CH$_2$—, R$^6$ is hydrogen, alkyl having 1 to 5 carbon atoms, or an atom or group which gives a pharmacologically acceptable salt, and n is an integer of 1 to 3;

R$^2$ is selected from the group consisting of:

(1) phenyl and naphthyl, wherein phenyl or naphthyl may be substituted by a group or groups selected from alkyl having 1 to 5 carbon atoms, phenyl hydroxyl, alkoxy having 1 to 5 carbon atoms, phenoxy, halogen, trifluoromethyl, cyano, nitro, amino, and alkylamino having 1 to 5 carbon atoms; or (2) alkyl having 1 to 5 carbon atoms, alkenyl having 2 to 5 carbon atoms, or alkynyl having 2 to 5 carbon atoms, wherein alkyl, alkenyl, or alkynyl is substituted by one or two Ar (wherein Ar is defined as the same as the above, and may be further substituted by a group or groups selected from —OH, —CF$_3$, and cycloalkyl having 3 to 8 carbon atoms);

R$^3$ is hydrogen, halogen, alkyl having 1 to 5 carbon atoms, or alkoxy having 1 to 5 carbon atoms; and either or both of A$^1$ and A$^2$ contain a hetero atom other than carbon.

2. A benzene fused heterocyclic derivative according to claim 1, wherein R$^1$ is —O—(CH$_2$)$_n$—COOR$^6$.

3. A benzene fused heterocyclic derivative according to claim 1, wherein A$^3$ is alkylene having 1 to 4 carbon atoms.

4. A benzene fused heterocyclic derivative according to claim 3, wherein A$^4$ is —S(O)$_p$— and p represents an integer of 0 to 2.

5. A pharmaceutical composition comprising a therapeutically effective amount of a benzene fused heterocyclic derivative according to any one of claims 1, 2, 3, or 4 as an active ingredient and a pharmaceutically acceptable carrier.

6. A thromboxane $A_2$ receptor antagonist comprising a benzene fused heterocyclic derivative according to any one of claims 1, 2, 3 or 4 as an active ingredient.

7. A thromboxane $A_2$ receptor antagonist having a $PGI_2$ receptor agonistic action, comprising a benzene fused heterocyclic derivative according to any of claims 1, 2, 3 or 4 as an active ingredient.

8. A pharmaceutical composition for treating humans having hypertension, thrombosis, ischemic heart diseases, cerebral circulatory disorders, peripheral circulatory disorders, arteriosclerosis, platelet functional disorders, hyperlipidemia, nephritis, asthma, or allergic diseases, comprising a benzene fused heterocyclic derivative according to any one of claims 1, 2, 3 or 4 as an active ingredient.

9. A pharmaceutical composition for preventing diseases in humans at high risk for developing one or more said disease, wherein said diseases comprise hypertension, thrombosis, ischemic heart diseases, cerebral circulatory disorders, peripheral circulatory disorders, arteriosclerosis, platelet functional disorders, hyperlipidemia, nephritis, asthma, or allergic diseases, said medicine comprising a benzene-fused heterocyclic derivative according to any one of claims 1, 2, 3 or 4 as an active ingredient.

10. A pharmaceutical composition according to claim 5, wherein said pharmaceutically acceptable carrier comprises one or more of starch, lactose, sucrose, crystalline cellulose, an excipient, a colorant, a lubricant, a binder, a disintegrant, and a coating agent.

11. A pharmaceutical composition according to claim 5, wherein said composition is in the form of a sterilized solution.

12. A pharmaceutical composition according to claim 11, further comprising one or more of a tonicity agent, glucose, a pH regulator, and solution adjuvant.

13. A pharmaceutical composition according to claim 5, wherein the form of said composition is one selected from the group consisting of tablets, powders, granules, solution, suppositories, ointments, or lotions.

14. A method for treating a disease related to high thromboxane $A_2$ activity in humans comprising administering a therapeutically effective amount of a benzene-fused heterocyclic derivative according to any one of claims 1, 2, 3 or 4.

15. A method according to claim 14, wherein said benzene-fused heterocyclic.

16. A method according to claim 15, wherein said benzene-fused heterocyclic derivative is administered 1 to 4 times per day.

17. A method according to claim 14, wherein said benzene-fused heterocyclic derivative is administered by a method selected from the group consisting of intravenous injection, intraarterial injection, intramuscular injection, percutaneous administration, subcutaneous administration, oral administration, or rectal administration.

\* \* \* \* \*

UNITED STATES PATENT AND TRADEMARK OFFICE
CERTIFICATE OF CORRECTION

PATENT NO. : 6,407,096 B1
DATED : June 18, 2002
INVENTOR(S) : Ohtake et al.

It is certified that error appears in the above-identified patent and that said Letters Patent is hereby corrected as shown below:

Column 16,
Line 67, please change "$R^2 - A^3 - A^4 - R^2$" to -- $R^{12} - A^3 - A^4 - R^2$ --.

Column 46,
Line 14, please change "$DMSOd_6$)" to -- $DMSO-d_6$) --.

Column 69,
Line 67, please change "$(M^{30})$" to -- $(M^+)$ --.

Column 72,
Line 44, please change "$M^{30}$)" to -- $M^+$) --.

Column 77,
Line 28, change "(310" to -- (370) --.

Column 84,
Line 13, please change "$cm^{+1}$" to -- $cm^{-1}$ --.

Column 90,
Line 39, please change "1060" to -- 1080 --.

Column 98,
Line 18, after "heterocyclic" please insert the following: -- derivative is administered at a dose in the range of 0.1 $\mu$/kg/day to 100 mg/kg/day --.

Signed and Sealed this

Twenty-first Day of January, 2003

JAMES E. ROGAN
*Director of the United States Patent and Trademark Office*